United States Patent
Buckler et al.

(10) Patent No.: US 11,094,058 B2
(45) Date of Patent: *Aug. 17, 2021

(54) SYSTEMS AND METHOD FOR COMPUTER-AIDED PHENOTYPING (CAP) USING RADIOLOGIC IMAGES

(71) Applicant: Elucid Bioimaging Inc., Boston, MA (US)

(72) Inventors: Andrew J. Buckler, Boston, MA (US); Kjell Johnson, Ann Arbor, MI (US); Xiaonan Ma, South Hamilton, MA (US); Keith A. Moulton, Amesbury, MA (US); Mark A. Buckler, Wenham, MA (US); Vladimir Valtchinov, Waban, MA (US); David S. Paik, Half Moon Bay, CA (US)

(73) Assignee: ELUCID BIOIMAGING INC., Boston, MA (US)

( * ) Notice: Subject to any disclaimer, the term of this patent is extended or adjusted under 35 U.S.C. 154(b) by 55 days.

This patent is subject to a terminal disclaimer.

(21) Appl. No.: 16/203,418

(22) Filed: Nov. 28, 2018

(65) Prior Publication Data
US 2019/0244347 A1    Aug. 8, 2019

Related U.S. Application Data

(63) Continuation-in-part of application No. 14/959,732, filed on Dec. 4, 2015, now Pat. No. 10,176,408.
(Continued)

(51) Int. Cl.
*G06K 9/00* (2006.01)
*G06T 7/00* (2017.01)
(Continued)

(52) U.S. Cl.
CPC ........ *G06T 7/0012* (2013.01); *G06K 9/00127* (2013.01); *G06K 9/3233* (2013.01);
(Continued)

(58) Field of Classification Search
CPC ....... A61B 5/7267; A61B 5/103; A61B 5/743; A61B 5/022; A61B 5/7275;
(Continued)

(56) References Cited

U.S. PATENT DOCUMENTS 6,108,635 A    8/2000 Herren et al.
7,127,095 B2   10/2006 Fakhri et al.
(Continued)

FOREIGN PATENT DOCUMENTS

WO    2015058151 A2    4/2015

OTHER PUBLICATIONS

Ariff et al. "Carotid Artery Hemodynamics: Observing Patient-specific Changes with Amlodipine and Lisinopril by Using MRI Imaging Computation Fluid Dynamics." Radiol. 257.3(2010):662-669.
(Continued)

*Primary Examiner* — Van D Huynh
(74) *Attorney, Agent, or Firm* — Pearl Cohen Zedek Latzer Baratz LLP

(57) ABSTRACT

Systems and methods for analyzing pathologies utilizing quantitative imaging are presented herein. Advantageously, the systems and methods of the present disclosure utilize a hierarchical analytics framework that identifies and quantify biological properties/analytes from imaging data and then identifies and characterizes one or more pathologies based on the quantified biological properties/analytes. This hierarchical approach of using imaging to examine underlying biology as an intermediary to assessing pathology provides many analytic and processing advantages over systems and
(Continued)

methods that are configured to directly determine and characterize pathology from underlying imaging data.

19 Claims, 22 Drawing Sheets

Related U.S. Application Data

(60) Provisional application No. 62/205,295, filed on Aug. 14, 2015, provisional application No. 62/205,305, filed on Aug. 14, 2015, provisional application No. 62/205,313, filed on Aug. 14, 2015, provisional application No. 62/205,322, filed on Aug. 14, 2015, provisional application No. 62/219,860, filed on Sep. 17, 2015, provisional application No. 62/676,975, filed on May 27, 2018, provisional application No. 62/771,448, filed on Nov. 26, 2018.

(51) Int. Cl.
| | | |
|---|---|---|
| *G06T 7/11* | (2017.01) | |
| *G06N 20/00* | (2019.01) | |
| *G06N 3/08* | (2006.01) | |
| *G06K 9/32* | (2006.01) | |
| *G06T 5/00* | (2006.01) | |
| *G06K 9/62* | (2006.01) | |
| *G06T 3/00* | (2006.01) | |

(52) U.S. Cl.
CPC ......... *G06K 9/6228* (2013.01); *G06K 9/6257* (2013.01); *G06K 9/6267* (2013.01); *G06N 3/08* (2013.01); *G06N 20/00* (2019.01); *G06T 3/00* (2013.01); *G06T 5/003* (2013.01); *G06T 7/11* (2017.01); *G06T 2207/10048* (2013.01); *G06T 2207/10081* (2013.01); *G06T 2207/10088* (2013.01); *G06T 2207/10101* (2013.01); *G06T 2207/10104* (2013.01); *G06T 2207/10108* (2013.01); *G06T 2207/10132* (2013.01); *G06T 2207/20081* (2013.01); *G06T 2207/30096* (2013.01); *G06T 2207/30104* (2013.01)

(58) Field of Classification Search
CPC . A61B 5/02007; A61B 6/5294; A61B 5/7485; A61B 6/504; A61B 5/0037; A61B 5/1075; A61B 5/489; A61B 6/037; A61B 6/481; A61B 2576/00; A61B 6/032; A61B 5/145; A61B 5/055; A61B 8/5223; A61B 5/0066; A61B 5/0075; G16H 50/20; G16H 50/50; G16H 10/60; G16H 30/40; G06T 5/003; G06T 5/20; G06T 11/001; G06T 11/60; G06T 7/0012; G06T 2207/10072; G06T 2207/30101; G06T 2207/20084; G06T 2207/30096; G06T 2207/20081; G06N 3/08
USPC ........................................................ 382/131
See application file for complete search history.

(56) References Cited

U.S. PATENT DOCUMENTS

| | | | |
|---|---|---|---|
| 7,519,211 | B2 | 4/2009 | Fakhri et al. |
| 8,157,742 | B2 | 4/2012 | Taylor |
| 8,175,355 | B2 | 5/2012 | Fakhri et al. |
| 8,249,815 | B2 | 8/2012 | Taylor |
| 8,311,747 | B2 | 11/2012 | Taylor |
| 8,311,748 | B2 | 11/2012 | Taylor et al. |
| 8,311,750 | B2 | 11/2012 | Taylor |
| 8,315,812 | B2 | 11/2012 | Taylor |
| 8,315,813 | B2 | 11/2012 | Taylor et al. |
| 8,315,814 | B2 | 11/2012 | Taylor et al. |
| 8,321,150 | B2 | 11/2012 | Taylor |
| 8,374,689 | B2 | 2/2013 | Gopinathan et al. |
| 8,386,188 | B2 | 2/2013 | Taylor et al. |
| 8,496,594 | B2 | 7/2013 | Taylor et al. |
| 8,523,779 | B2 | 9/2013 | Taylor et al. |
| 8,548,778 | B1 | 10/2013 | Hart et al. |
| 8,553,832 | B2 | 10/2013 | Camus et al. |
| 8,554,490 | B2 | 10/2013 | Tang et al. |
| 8,594,950 | B2 | 11/2013 | Taylor |
| 8,606,530 | B2 | 12/2013 | Taylor |
| 8,630,812 | B2 | 1/2014 | Taylor |
| 8,706,457 | B2 | 4/2014 | Hart et al. |
| 8,734,356 | B2 | 5/2014 | Taylor |
| 8,734,357 | B2 | 5/2014 | Taylor |
| 8,768,669 | B1 | 7/2014 | Hart et al. |
| 8,768,670 | B1 | 7/2014 | Hart et al. |
| 8,812,245 | B2 | 8/2014 | Taylor |
| 8,812,246 | B2 | 8/2014 | Taylor |
| 8,824,752 | B1 | 9/2014 | Fonte et al. |
| 8,825,151 | B2 | 9/2014 | Gopinathan et al. |
| 8,831,314 | B1 | 9/2014 | Fonte et al. |
| 8,831,315 | B1 | 9/2014 | Fonte et al. |
| 8,855,984 | B2 | 10/2014 | Hart et al. |
| 8,861,820 | B2 | 10/2014 | Fonte et al. |
| 8,914,264 | B1 | 12/2014 | Hart et al. |
| 8,970,578 | B2 | 3/2015 | Voros et al. |
| 8,977,339 | B1 | 3/2015 | Wu et al. |
| 9,002,690 | B2 | 4/2015 | Hart et al. |
| 9,008,405 | B2 | 4/2015 | Fonte et al. |
| 9,042,613 | B2 | 5/2015 | Spilker et al. |
| 9,043,190 | B2 | 5/2015 | Grady et al. |
| 9,063,634 | B2 | 6/2015 | Hart et al. |
| 9,063,635 | B2 | 6/2015 | Hart et al. |
| 9,078,564 | B2 | 7/2015 | Taylor |
| 9,081,882 | B2 | 7/2015 | Taylor |
| 9,087,147 | B1 | 7/2015 | Fonte |
| 9,119,540 | B2 | 9/2015 | Sharma et al. |
| 9,149,197 | B2 | 10/2015 | Taylor |
| 9,152,757 | B2 | 10/2015 | Taylor |
| 9,155,512 | B2 | 10/2015 | Choi et al. |
| 9,167,974 | B2 | 10/2015 | Taylor |
| 9,168,012 | B2 | 10/2015 | Hart et al. |
| 9,189,600 | B2 | 11/2015 | Spilker et al. |
| 9,195,801 | B1 | 11/2015 | Sankaran et al. |
| 9,202,010 | B2 | 12/2015 | Taylor et al. |
| 9,220,418 | B2 | 12/2015 | Choi et al. |
| 9,220,419 | B2 | 12/2015 | Choi et al. |
| 9,226,672 | B2 | 1/2016 | Taylor |
| 9,235,679 | B2 | 1/2016 | Taylor |
| 9,239,905 | B1 | 1/2016 | Sankaran et al. |
| 9,247,918 | B2 | 2/2016 | Sharma et al. |
| 9,262,581 | B2 | 2/2016 | Kim et al. |
| 9,265,473 | B2 | 2/2016 | Mittal et al. |
| 9,268,902 | B2 | 2/2016 | Taylor et al. |
| 9,271,657 | B2 | 3/2016 | Taylor |
| 9,280,639 | B2 | 3/2016 | Sankaran et al. |
| 9,292,659 | B1 | 3/2016 | Grady et al. |
| 9,320,487 | B2 | 4/2016 | Mittal et al. |
| 9,336,354 | B1 | 5/2016 | Sankaran et al. |
| 9,339,200 | B2 | 5/2016 | Fonte |
| 9,349,178 | B1 | 5/2016 | Itu et al. |
| 9,386,933 | B2 | 7/2016 | Grady et al. |
| 9,390,224 | B2 | 7/2016 | Choi et al. |
| 9,390,232 | B2 | 7/2016 | Taylor et al. |
| 9,405,886 | B2 | 8/2016 | Taylor et al. |
| 9,424,395 | B2 | 8/2016 | Sankaran et al. |
| 9,449,145 | B2 | 9/2016 | Sankaran et al. |
| 9,449,146 | B2 | 9/2016 | Spilker et al. |
| 9,449,147 | B2 | 9/2016 | Taylor |
| 9,471,999 | B2 | 10/2016 | Ishii et al. |
| 9,501,622 | B2 | 11/2016 | Sankaran et al. |
| 9,517,040 | B2 | 12/2016 | Hart et al. |
| 9,538,925 | B2 | 1/2017 | Sharma et al. |
| 9,572,495 | B2 | 2/2017 | Schmitt et al. |
| 9,585,623 | B2 | 3/2017 | Fonte et al. |
| 9,585,723 | B2 | 3/2017 | Taylor |
| 9,594,876 | B2 | 3/2017 | Sankaran et al. |

(56) References Cited

U.S. PATENT DOCUMENTS

| | | | |
|---|---|---|---|
| 9,595,089 B2 | 3/2017 | Itu et al. | |
| 9,607,130 B2 | 3/2017 | Grady et al. | |
| 9,607,386 B2 | 3/2017 | Grady et al. | |
| 9,613,186 B2 | 4/2017 | Fonte | |
| 9,629,563 B2 | 4/2017 | Sharma et al. | |
| 9,633,454 B2 | 4/2017 | Lauritsch et al. | |
| 9,649,171 B2 | 5/2017 | Sankaran et al. | |
| 9,668,700 B2 | 6/2017 | Taylor | |
| 9,672,615 B2 | 6/2017 | Fonte et al. | |
| 9,675,301 B2 | 6/2017 | Fonte et al. | |
| 9,679,374 B2 | 6/2017 | Choi et al. | |
| 9,697,330 B2 | 7/2017 | Taylor | |
| 9,700,219 B2 | 7/2017 | Sharma et al. | |
| 9,706,925 B2 | 7/2017 | Taylor | |
| 9,737,276 B2 | 8/2017 | Mittal et al. | |
| 9,743,835 B2 | 8/2017 | Taylor | |
| 9,747,525 B2 | 8/2017 | Sauer et al. | |
| 9,754,082 B2 | 9/2017 | Taylor et al. | |
| 9,757,073 B2 | 9/2017 | Goshen et al. | |
| 9,761,048 B2 * | 9/2017 | Igarashi | A61B 8/5207 |
| 9,770,303 B2 | 9/2017 | Choi et al. | |
| 9,773,219 B2 | 9/2017 | Sankaran et al. | |
| 9,785,746 B2 | 10/2017 | Fonte et al. | |
| 9,785,748 B2 | 10/2017 | Koo et al. | |
| 9,786,068 B2 | 10/2017 | Ishii et al. | |
| 9,788,807 B2 | 10/2017 | Schmitt et al. | |
| 9,801,689 B2 | 10/2017 | Taylor | |
| 9,805,168 B2 | 10/2017 | Sankaran et al. | |
| 9,805,463 B2 | 10/2017 | Choi et al. | |
| 9,836,840 B2 | 12/2017 | Fonte et al. | |
| 9,839,399 B2 | 12/2017 | Fonte et al. | |
| 9,839,483 B2 | 12/2017 | Sankaran et al. | |
| 9,839,484 B2 | 12/2017 | Taylor | |
| 9,842,401 B2 | 12/2017 | Prevrhal et al. | |
| 9,855,105 B2 | 1/2018 | Taylor | |
| 9,858,387 B2 | 1/2018 | Lavi et al. | |
| 9,861,284 B2 | 1/2018 | Taylor | |
| 9,864,840 B2 | 1/2018 | Grady et al. | |
| 9,867,584 B2 | 1/2018 | Grass et al. | |
| 9,877,657 B2 | 1/2018 | Igarashi | |
| 9,888,968 B2 | 2/2018 | Sauer et al. | |
| 9,888,971 B2 | 2/2018 | Taylor | |
| 9,891,044 B2 | 2/2018 | Tu et al. | |
| 9,913,616 B2 | 3/2018 | Fonte et al. | |
| 9,918,690 B2 | 3/2018 | Itu et al. | |
| 9,924,869 B2 | 3/2018 | Kim et al. | |
| 9,928,593 B2 | 3/2018 | Ooga et al. | |
| 9,940,736 B2 | 4/2018 | Ishii et al. | |
| 9,943,233 B2 | 4/2018 | Lavi et al. | |
| 9,949,650 B2 | 4/2018 | Edic et al. | |
| 9,965,891 B2 | 5/2018 | Grady et al. | |
| 9,974,454 B2 | 5/2018 | Sharma et al. | |
| 9,974,508 B2 | 5/2018 | Kassab et al. | |
| 9,974,616 B2 | 5/2018 | Grady et al. | |
| 9,977,869 B2 | 5/2018 | Lavi et al. | |
| 9,984,465 B1 | 5/2018 | Ma et al. | |
| 9,993,303 B2 | 6/2018 | Sankaran et al. | |
| 9,999,361 B2 | 6/2018 | Sharma et al. | |
| 10,002,419 B2 | 6/2018 | Rapaka et al. | |
| 10,007,762 B2 | 6/2018 | Grady et al. | |
| 10,010,255 B2 | 7/2018 | Fonte et al. | |
| 10,034,614 B2 | 7/2018 | Edic et al. | |
| 10,052,031 B2 | 8/2018 | Sharma et al. | |
| 10,052,032 B2 | 8/2018 | Grass et al. | |
| 10,052,158 B2 | 8/2018 | Taylor | |
| 10,080,613 B2 | 9/2018 | Taylor | |
| 10,080,614 B2 | 9/2018 | Taylor | |
| 10,092,247 B2 | 10/2018 | Taylor | |
| 10,092,360 B2 | 10/2018 | Taylor | |
| 10,096,104 B2 | 10/2018 | Choi et al. | |
| 2002/0103776 A1 | 8/2002 | Bella et al. | |
| 2003/0105638 A1 | 6/2003 | Taira | |
| 2005/0043614 A1 * | 2/2005 | Huizenga | C23F 11/08 600/427 |
| 2005/0118632 A1 * | 6/2005 | Chen | C12N 9/6489 435/6.16 |
| 2006/0242288 A1 | 10/2006 | Masurkar | |
| 2007/0130206 A1 | 6/2007 | Zhou et al. | |
| 2007/0208516 A1 | 9/2007 | Kutsyy et al. | |
| 2007/0260141 A1 * | 11/2007 | Margolis | A61B 8/12 600/437 |
| 2008/0027695 A1 | 1/2008 | Balgi et al. | |
| 2008/0201280 A1 | 8/2008 | Martin et al. | |
| 2009/0171871 A1 | 7/2009 | Zhang et al. | |
| 2009/0258925 A1 | 10/2009 | Wahlestedt | |
| 2009/0259459 A1 | 10/2009 | Ceusters et al. | |
| 2009/0324126 A1 | 12/2009 | Zitnick et al. | |
| 2010/0070448 A1 | 3/2010 | Omoigui | |
| 2010/0262545 A1 | 10/2010 | Herlitz | |
| 2011/0026798 A1 * | 2/2011 | Madabhushi | G06T 7/11 382/131 |
| 2011/0027181 A1 | 2/2011 | Amodei et al. | |
| 2012/0278060 A1 | 11/2012 | Cancedda et al. | |
| 2013/0275094 A1 | 10/2013 | Ortoleva | |
| 2014/0126770 A1 | 5/2014 | Odessky et al. | |
| 2014/0276121 A1 | 9/2014 | Kassab | |
| 2014/0365239 A1 | 12/2014 | Sadeghi | |
| 2015/0154275 A1 | 6/2015 | Senart et al. | |
| 2015/0234921 A1 | 8/2015 | Li | |
| 2015/0324527 A1 | 11/2015 | Siegel et al. | |
| 2016/0203599 A1 | 7/2016 | Gillies et al. | |
| 2016/0310018 A1 * | 10/2016 | Fonte | A61B 5/14535 |
| 2016/0314580 A1 * | 10/2016 | Lloyd | G06T 7/0012 |
| 2016/0326588 A1 | 11/2016 | Beier | |
| 2016/0364630 A1 | 12/2016 | Reicher et al. | |
| 2017/0358079 A1 * | 12/2017 | Gillies | A61B 6/032 |
| 2018/0253591 A1 * | 9/2018 | Madabhushi | G06K 9/00147 |
| 2019/0244347 A1 | 8/2019 | Buckler et al. | |

OTHER PUBLICATIONS

Bourque et al. "Usefulness of Cardiovascular Magnetic Resonance Imaging of the Superficial Femoral Artery for Screening Patients with Diabetes Mellitus for Artherosclerosis." Am. J. Cardiol. 110. 1(2012):50-56.

Buckler et al. "A Collaborative Enterprise for Multi-Stakeholder Participation in the Advancement of Quantitative Imaging." Radiol. 258.3(2011):906-914.

Buckler et al. "Data Sets for the Qualification of CT as a Quantitative Imaging Biomarker in Lung Cancer." Optics Exp. 18.14(2010):16.

Buckler et al. "Data Sets for the Qualification of Volumetric CT as a Quantitative Imaging Biomarker in Lung Cancer." Optics Exp. 18.14(2010):15267-15282.

Buckler et al. "Standardization of Quantitative Imaging: The Time is Right and 18F-FDG PET/CT is a Good Place to Start." J. Nuclear Med. 52.2(2011):171-172.

Buckler et al. "The Use of Volumetric CT as an Imaging Biomarker in Lung Cancer." Acadmic Radiol. 17.1 (2010):100-106.

Buckler et al. "Volumetric CT in Lung Cancer: An Example for the Qualification of Imaging as a Biomarker." Academic Radiol. 17.1(2010):107-115.

Freedman et al. "Statistical Validation of Intermediate Endpoints for Chronic Diseases." Stat. Med. 11(1992):167-178.

Fuleihan et al. "Reproducibility of DXA Absorptiometry: A Model for Bone Loss Estimates." J. Bone Miner. Res. 10.74 (1995):1004-1014.

Horie et al. "Assessment of Carotid Plaque Stability Based on Dynamic Enhancement Pattern in Plaque Components with Multidetector CT Angiography." Stroke. 43.2(2012):393-398.

Irace et al. "Human Common Carotid Wall Shear Stress as a Function of Age and Gender: A 12-year Follow-up Study." Age. 34.6(2012):1553-1562.

Jaffe, "Measures of Response: Recist, Who, and New Alternatives." J. Clin. Oncol. 24.20(2006):3245-3251.

Katz, "Biomarkers and Surrogate Markers: An FDA Perspective." NeuroRx. 1.2(2004):189-195.

Kerwin et al. "MRI of Carotid Artherosclerosis." Am. J. Roentgenol. 200.3(2013):W304-W313.

(56) References Cited

OTHER PUBLICATIONS

Kim et al. "A Curve Evolution-based variational approach to Simultaneous Image Restoration and Segmentation." IEEE Int. Conf. Image Proc. (2002):1-109.
Lathia et al. "The Value, Qualification, and Regulatory Use of Surrogate End Points in Drug Development." Clin. Pharmacol. Therapeutics. 86.1(2009):32-43.
Mozley et al. "Change in Lung Tumor Volume as a Biomarker of Treatment Response: A Critical Review of the Evidence." Ann. Oncol. 21.9(2010):1751-1755.
Phinikaridou et al. "Regions of Low Endothelial Shear Stress Colocalize with Positive Vascular Remodeling and Atherosclerotic Plaque Disruption: An in vivo Magnetic Resonance Imaging Study." Circ. Cardiovasc. Imaging. 6.2(2013):302-310.
Sui et al. "Assessment of Wall Shear Stress in the Common Carotid Artery of Healthy Subjects Using 3.0-Tesla Magentic Resonanance." Acta Radiologica. 49.4(2008):442-449.
ten Kate et al. "Noninvasive Imaging of the Vulnerable Atherosclerotic Plaque." Current Problems Cardiol. 35.11 (2010):556-591.
Van Klavern et al. "Management of Lung Nodules Detected by Volume CT Scanning." New Engl. J. Med. 361(2009):23.
Varma et al. "Coronary Vessel Wall Contrast Enhancement Imaging as a Potential Direct Marker of Coronary Involvement: Integration of Findings from CAD and SLE Patients." JACC Cardiovasc. Imaging. 7.8(2014):762-770.
Wintermark et al. "Carotid Plaque CT Imaging in Stroke and Non-Stroke Patients." Ann. Neurol. 64.2(2008):149-157.
Wintermark et al. "High-Resolution CT Imaging of Carotid Artery Atherosclerotic Plaques." Am. J. Neuroradiol. 29.5(2008):875-882.
Wong et al. "Imaging in Drug Discovery, Preclinical, and Early Clinical Development." J. Nuclear Med. 49.6(2008):26N-28N.
Woodcock et al. "The FDA Critical Path Initiative and its Influence on New Drug Development." Annu. Rev. Med. 59(2008):1-12.
Zhao et al. "Evaluating Variability in Tumor Measurements from Same-Day Repeat CT Scans of Patients with Non-Small Cell Lung Cancer." Radiol. 252.1(2009):263-272.
Aerts, H.J.W.L., et al., Decoding tumour phenotype by noninvasive imaging using a quantitative radiomics approach. Nat Commun, 2014. 5.
Ahmadi, A., et al., Association of Coronary Stenosis and Plaque Morphology With Fractional Flow Reserve and Outcomes. JAMA Cardiol, 2016. 1(3): p. 350-7.
Ahmadi, A., et al., Lesion-Specific and Vessel-Related Determinants of Fractional Flow Reserve Beyond Coronary Artery Stenosis. JACC Cardiovasc Imaging, 2018. 11(4): p. 521-530.
Albuquerque, L.C., et al., Intraplaque hemorrhage assessed by high-resolution magnetic resonance imaging and C-reactive protein in carotid atherosclerosis. Journal of Vascular Surgery, 2007. 46(6): p. 1130-1137.
Alimohammadi, M., et al., Development of a Patient-Specific Multi-Scale Model to Understand Atherosclerosis and Calcification Locations: Comparison with in vivo Data in an Aortic Dissection. Front Physiol, 2016. 7: p. 238.
Aoki, T., et al., Peripheral Lung Adenocarcinoma: Correlation of Thin-Section CT Findings with Histologic Prognostic Factors and Survival 1. Radiology, 2001. 220(3): p. 803-809.
Atkinson, A.J., et al., Biomarkers and surrogate endpoints: Preferred definitions and conceptual framework*. Clinical Pharmacology & Therapeutics, 2001. 69(3): p. 89-95.
Bittencourt, M.S., et al., Prognostic Value of Nonobstructive and Obstructive Coronary Artery Disease Detected by Coronary Computed Tomography Angiography to Identify Cardiovascular Events. Circulation: Cardiovascular Imaging, 2014. 7(2): p. 282-291.
Buckler, A., et al., A Novel Knowledge Representation Framework for the Statistical Validation of Quantitative Imaging Biomarkers. Journal of Digital Imaging, 2013. 26(4): p. 614-629.
Buckler, A.J., et al., Quantitative imaging biomarker ontology (QIBO) for knowledge representation of biomedical imaging biomarkers. Journal of digital imaging : the official journal of the Society for Computer Applications in Radiology, 2013. 26(4): p. 630-41.
Buckler, A.J., et al., Quantitative imaging test approval and biomarker qualification: interrelated but distinct activities. Radiology, 2011. 259(3): p. 875-84.
Buyse, M., et al., The validation of surrogate endpoints in meta-analyses of randomized experiments. Biostatistics, 2000. 1(1): p. 49-67.
Cai, J., et al., In vivo quantitative measurement of intact fibrous cap and lipid-rich necrotic core size in atherosclerotic carotid plaque: comparison of high-resolution, contrast-enhanced magnetic resonance imaging and histology. Circulation, 2005. 112(22): p. 3437-44.
Castellano et al. "Texture analysis of medical images," Clinical Radiology, Dec. 1, 2004 (Dec. 1, 2004) vol. 59.
Chan, T.F. and L.A. Vese, Active contours without edges. IEEE Trans Image Process, 2001. 10(2): p. 266-77.
Choi et al. "Multiscale image segmentation using wavelet-domain hidden Markov models" IEEE Trans Image Process, Sep. 1, 2001 (Sep. 1, 2001), vol. 10.
Coenen, A., et al., Diagnostic accuracy of a machine-learning approach to coronary computed tomographic angiography—based fractional flow reserve: result from the Machine consortium. Circulation: Cardiovascular Imaging, 2018. 11(6): p. e007217.
de Bono, B., et al., The Open Physiology workflow: modeling processes over physiology circuitboards of interoperable tissue units. Front Physiol, 2015. 6: p. 24.
de Graaf, M., et al., Automatic quantification and characterization of coronary atherosclerosis with computed tomography coronary angiography: cross-correlation with intravascular ultrasound virtual histology. Int J Cardiovasc Imaging, 2013. 29(5): p. 1177-1190.
de Weert, T.T., et al., In Vivo Characterization and Quantification of Atherosclerotic Carotid Plaque Components With Multidetector Computed Tomography and Histopathological Correlation. Arterioscler Thromb Vasc Biol, 2006. 26(10): p. 2366-2372.
DeMarco, J.K. and J. Huston, Imaging of high-risk carotid artery plaques: current status and future directions. Neurosurgical Focus, 2014. 36(1): p. E1.
Diaz-Zamudio, M., et al., Automated Quantitative Plaque Burden from Coronary CT Angiography Noninvasively Predicts Hemodynamic Significance by using Fractional Flow Reserve in Intermediate Coronary Lesions. Radiology, 2015. 276(2): p. 408-15.
Dong, L., et al., Carotid Artery Atherosclerosis: Effect of Intensive Lipid Therapy on the Vasa Vasorum—Evaluation by Using Dynamic Contrast-enhanced MR Imaging. Radiology, 2011. 260(1): p. 224-231.
Filardi, V., Carotid artery stenosis near a bifurcation investigated by fluid dynamic analyses. The neuroradiology journal, 2013. 26(4): p. 439-453.
Fleming, T.R. and D.L. DeMets, Surrogate end points in clinical trials: are we being misled? Ann Intern Med, 1996. 125(7): p. 605-13.
Freimuth, R.R., et al., Life sciences domain analysis model. J Am Med Inform Assoc, 2012. 19(6): p. 1095-102.
Fujimoto, S., et al., A novel method for non-invasive plaque morphology analysis by coronary computed tomography angiography. Int J Cardiovasc Imaging, 2014. 30(7): p. 1373-1382.
Gaston A. Rodriguez-Granillo, Patricia Carrascosa, Nico Bruining, and a.H.M.G.-G. RonWaksman, Defining the non-vulnerable and vulnerable patients with computed tomography coronary angiography: evaluation of atherosclerotic plaque burden and composition. European Heart Journal—Cardiovascular Imaging, 2016. 2016(17): p. 481-491.
Gevaert, O., et al., Non-small cell lung cancer: identifying prognostic imaging biomarkers by leveraging public gene expression microarray data—methods and preliminary results. Radiology, 2012. 264(2): p. 387-396.
Ghazalpour, A., et al., Thematic review series: The pathogenesis of atherosclerosis. Toward a biological network for atherosclerosis. J Lipid Res, 2004. 45(10): p. 1793-805.
Gupta, A., et al., Carotid Plaque MRI and Stroke Risk a Systematic Review and Meta-analysis. Stroke, 2013.44(11): p. 3071-3077.
Gupta, A., et al., Detection of Symptomatic Carotid Plaque Using Source Data from MR and CT Angiography: A Correlative Study. Cerebrovasc Dis, 2015. 39(3-4): p. 151-61.

(56) References Cited

OTHER PUBLICATIONS

Gupta, A., et al., Intraplaque high-intensity signal on 3D time-of-flight MR angiography is strongly associated with symptomatic carotid artery stenosis. American Journal of Neuroradiology, 2014. 35(3): p. 557-561.

Hecht, H.S., Coronary artery calcium scanning: past, present, and future. JACC Cardiovasc Imaging, 2015. 8: p. 579-596.

Hecht, H.S., J. Narula, and W.F. Fearon, Fractional Flow Reserve and Coronary Computed Tomographic Angiography: A Review and Critical Analysis. Circ Res, 2016. 119(2): p. 300-16.

Helft, G., et al., Progression and regression of atherosclerotic lesions: monitoring with serial noninvasive magnetic resonance imaging. Circulation, 2002. 105(8): p. 993-8.

Inoue, K, et al., Serial Coronary CT Angiography—Verified Changes in Plaque Characteristics as an End Point: Evaluation of Effect of Statin Intervention. JACC: Cardiovascular Imaging, 2010. 3(7): p. 691-698.

International Search Report & Written Opinion in co-pending international patent application No. PCT/US2016/065132 dated Mar. 17, 2017.

Khan et al. "Robust atlas-based brain segmentation using multi-structure confidence-weighted registration" Proceedings of the 12th International Conference on Medical Image Computing, Sep. 20, 2009.

Krizhevsky, A., I. Sutskever, and G.E. Hinton. Imagenet classification with deep convolutional neural networks. In Advances in neural information processing systems. 2012.

Lobatto, M.E., et al., Multimodal Clinical Imaging to Longitudinally Assess a Nanomedical Anti-Inflammatory Treatment in Experimental Atherosclerosis. Molecular Pharmaceutics, 2010. 7(6): p. 2020-2029.

Ma, X., et al., Volumes Learned: It Takes More Than Size to "Size Up" Pulmonary Lesions. Aced Radiol, 2016. 23(9): p. 1190-8.

Melander, O., et al., Novel and conventional biomarkers for prediction of incident cardiovascular events in the community. JAMA : the journal of the American Medical Association, 2009. 302(1): p. 49-57.

Miao, C., et al., The Association of Pericardial Fat with Coronary Artery Plaque Index at MR Imaging: The Multi-Ethnic Study of Atherosclerosis (MESA). Radiology, 2011. 261(1): p. 109-115.

Mono, M.L., et al., Plaque Characteristics of Asymptomatic Carotid Stenosis and Risk of Stroke. Cerebrovascular Diseases, 2012. 34(5-6): p. 343-350.

Narula, J., et al., Histopathologic characteristics of atherosclerotic coronary disease and implications of the findings for the invasive and noninvasive detection of vulnerable plaques. Journal of the American College of Cardiology, 2013. 61(10): p. 1041-1051.

Naylor, A.R., Identifying the high-risk carotid plaque. The Journal of Cardiovascular Surgery, 2014. 55(2): p. 11-20.

Perera, R. and P. Nand, Recent Advances in Natural Language Generation: A Survey and Classification of the Empirical Literature. vol. 36. 2017. 1-31.

Prentice, R.L., Surrogate endpoints in clinical trials: definition and operational criteria. Statistics in medicine, 1989. 8(4): p. 431-440.

International Search Report & Written Opinion in co-pending international application No. PCT/US16/67463 dated Mar. 10, 2017 (10 pages).

Reddy et al. "Confidence guided enhancing brain tumor segmentation in multi-parametric MRI" Proceedings of the 12th International Conference on Medical Image Computing and Computer-Assisted Intervention, MICCAI 2009, held in London, UK, Sep. 20, 2009.

Saba, L., et al., Carotid Artery Plaque Characterization Using CT Multienergy Imaging. American Journal of Neuroradiology, 2013. 34(4): p. 855-859.

Sadot, A., et al., Toward verified biological models. IEEE/ACM Trans Comput Biol Bioinform, 2008. 5(2): p. 223-34.

Sargent, D., et al., Validation of novel imaging methodologies for use as cancer clinical trial end-points. European Journal of Cancer, 2009. 45(2): p. 290-299.

Stary, H.C., et al., A definition of advanced types of atherosclerotic lesions and a histological classification of atherosclerosis A report from the Committee on Vascular Lesions of the Council on Arteriosclerosis, American Heart Association. Circulation, 1995. 92(5): p. 1355-1374.

Stary, H.C., Natural history and histological classification of atherosclerotic lesions: an update. Arterioscler Thromb Vasc Biol, 2000.20(5): p. 1177-8.

van 't Klooster, R., et al., Visualization of Local Changes in Vessel Wall Morphology and Plaque Progression in Serial Carotid Artery Magnetic Resonance Imaging. Stroke, 2014. 45(8): p. e160-e163.

Virmani, R., et al., Pathology of the Vulnerable Plaque. JACC, 2006. 47(8): p. C13-8.

Voros, S., et al., Coronary Atherosclerosis Imaging by Coronary CT Angiography. JACC Cardiovasc Imaging, 2011. 4(5): p. 537-48.

Zavodni, A.E.H., et al., Carotid Artery Plaque Morphology and Composition in Relation to Incident Cardiovascular—Events: The Multi-Ethnic Study of Atherosclerosis (MESA). Radiology, 2014. 271(2): p. 381-389.

William B. Kerr et al. "A Methodology and Metric for Quantitative Analysis and Parameter Optimization of Unsupervised, Multi-Region Image Segmentation", Proceeding of the 8th IASTED International Conference on Signal and Image Processing, Aug. 14, 2006, pp. 243-248.

Prescott, J., Quantitative Imaging Biomarkers: The Application of Advanced Image Processing and Analysis to Clinical and Preclinical Decision Making. Journal of Digital Imaging, 2013. 26(1): p. 97-108.

\* cited by examiner

Computing Putative Analyte Blobs
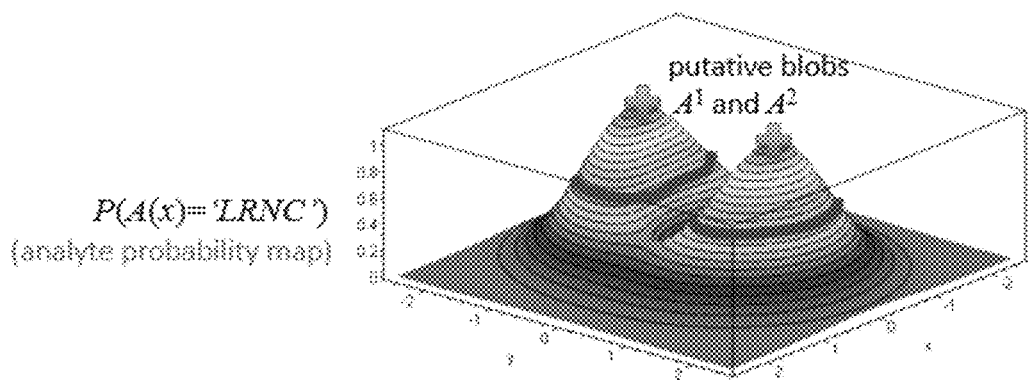
Figure 6
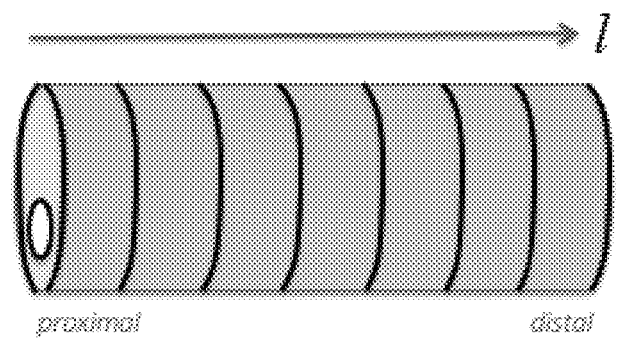
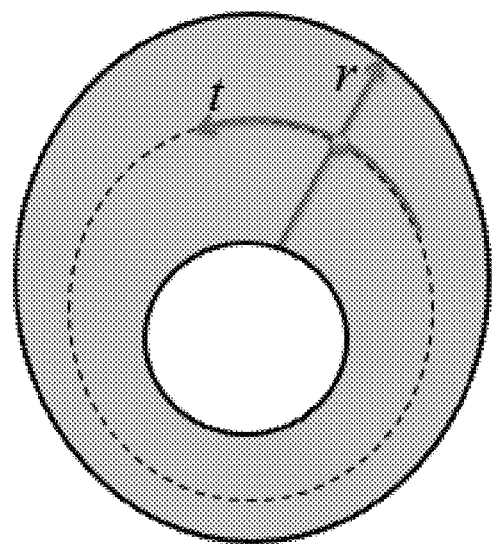
Figure 7

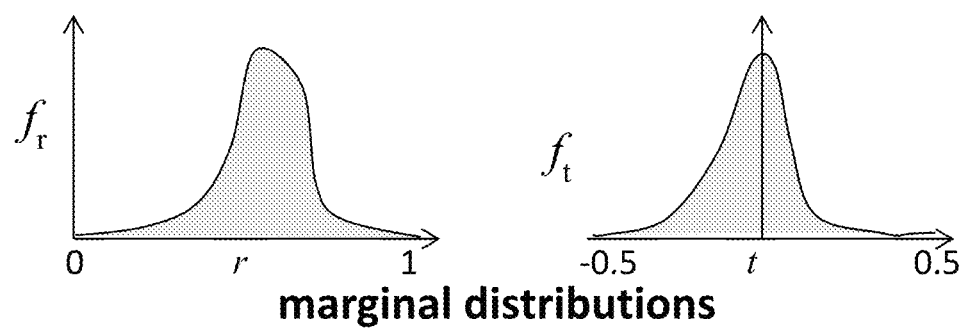
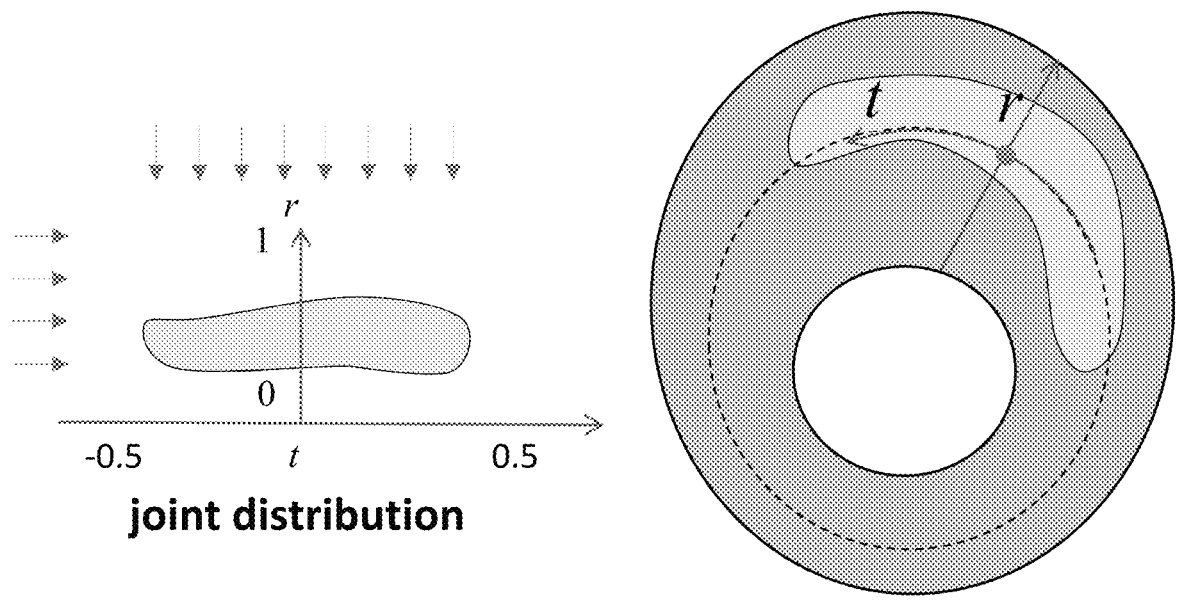
Figure 10
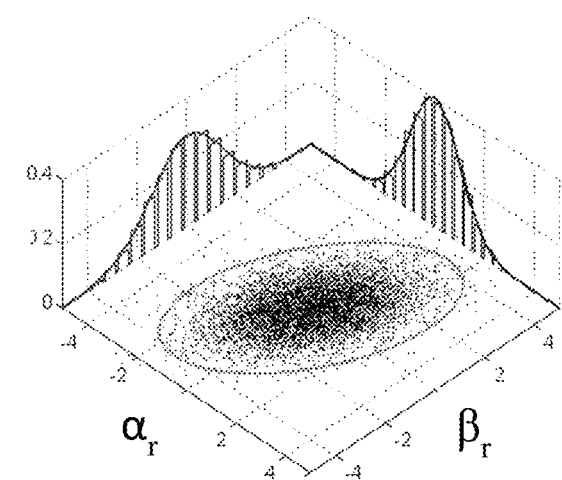
Figure 11

EAAAAAEEAAAEEAAAAAA ...    GATTTACCCAAAA ...

| Dataset Name | Unwrapped / Donut | Training/ Validation | Training Iteration | # Imgs in Dataset | Total Acc % | Unstable True Positive | Unstable False Positive | Unstable False Negative | Unstable True Negative |
|---|---|---|---|---|---|---|---|---|---|
| 2018-02_WN | Unwrapped | Training | 2000 | 5186 | 99.28 | 2609 | 36 | 1 | 2540 |
| 2018-02_WN | Unwrapped | Training | 10000 | 5186 | 99.46 | 2610 | 28 | 0 | 2548 |
| 2018-02_WN | Unwrapped | Validation | 2000 | 97 | 78.35 | 62 | 16 | 5 | 14 |
| 2018-02_WN | Unwrapped | Validation | 10000 | 97 | 78.35 | 62 | 16 | 5 | 14 |
| 2018-04_WN | Unwrapped | Training | 2000 | 5186 | 94.58 | 2466 | 137 | 144 | 2439 |
| 2018-04_WN | Unwrapped | Training | 10000 | 5186 | 93.06 | 2489 | 239 | 121 | 2337 |
| 2018-04_WN | Unwrapped | Validation | 2000 | 97 | 82.47 | 60 | 10 | 7 | 20 |
| 2018-04_WN | Unwrapped | Validation | 10000 | 97 | 83.51 | 61 | 10 | 6 | 20 |
| 2018-04_RV | Unwrapped | Training | 2000 | 2019 | 99.41 | 1028 | 11 | 1 | 979 |
| 2018-04_RV | Unwrapped | Training | 10000 | 2019 | 99.9 | 1029 | 2 | 0 | 988 |
| 2018-04_RV | Unwrapped | Validation | 2000 | 64 | 92.19 | 18 | 2 | 3 | 41 |
| 2018-04_RV | Unwrapped | Validation | 10000 | 64 | 93.75 | 19 | 2 | 2 | 41 |
| 2018-04_WN_RV | Unwrapped | Training | 2000 | 7205 | 90.63 | 3601 | 637 | 38 | 2929 |
| 2018-04_WN_RV | Unwrapped | Training | 10000 | 7205 | 90.62 | 3614 | 651 | 25 | 2915 |
| 2018-04_WN_RV | Unwrapped | Validation | 2000 | 161 | 65.22 | 77 | 45 | 11 | 28 |
| 2018-04_WN_RV | Unwrapped | Validation | 10000 | 161 | 64.59 | 80 | 49 | 8 | 24 |
| 2018-02_WN | Donut | Training | 2000 | 5186 | 98.97 | 2572 | 15 | 38 | 2561 |
| 2018-02_WN | Donut | Training | 10000 | 5186 | 99.96 | 2610 | 2 | 0 | 2574 |
| 2018-02_WN | Donut | Validation | 2000 | 97 | 71.13 | 45 | 6 | 22 | 24 |
| 2018-02_WN | Donut | Validation | 10000 | 97 | 76.28 | 50 | 6 | 17 | 24 |
| 2018-04_WN | Donut | Training | 2000 | 5186 | 92.46 | 2223 | 4 | 387 | 2572 |
| 2018-04_WN | Donut | Training | 10000 | 5186 | 98.36 | 2542 | 17 | 68 | 2559 |
| 2018-04_WN | Donut | Validation | 2000 | 97 | 64.94 | 41 | 8 | 26 | 22 |
| 2018-04_WN | Donut | Validation | 10000 | 97 | 77.32 | 53 | 8 | 14 | 22 |
| 2018-04_RV | Donut | Training | 2000 | 2019 | 100 | 1029 | 0 | 0 | 990 |
| 2018-04_RV | Donut | Training | 10000 | 2019 | 100 | 1029 | 0 | 0 | 990 |
| 2018-04_RV | Donut | Validation | 2000 | 64 | 92.19 | 19 | 3 | 2 | 40 |
| 2018-04_RV | Donut | Validation | 10000 | 64 | 92.19 | 19 | 3 | 2 | 40 |
| 2018-04_WN_RV | Donut | Training | 2000 | 7205 | 90.13 | 3468 | 540 | 171 | 3026 |
| 2018-04_WN_RV | Donut | Training | 10000 | 7205 | 98.63 | 3567 | 27 | 72 | 3539 |
| 2018-04_WN_RV | Donut | Validation | 2000 | 161 | 68.94 | 71 | 33 | 17 | 40 |
| 2018-04_WN_RV | Donut | Validation | 10000 | 161 | 78.26 | 68 | 15 | 20 | 58 |

Networks Used:
Unwrapped Network: 400x200 AlexNet style
Donut Network: 280x280 AlexNet style Augmentation Details:
Augmentation multiplier: 15
Class normalization: Yes

Figure 28

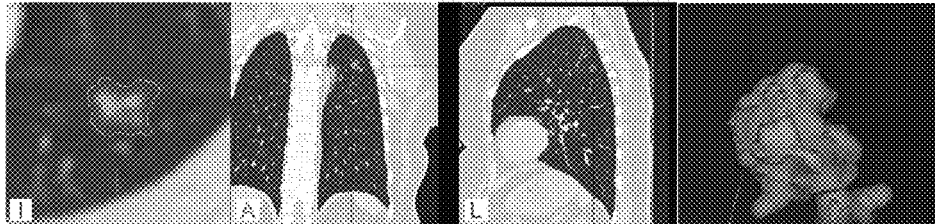

Figure 29

| | | |
|---|---|---|
| | The size of the lesion | Volume (lesion, solid portion, ground-glass portion), in mm³ |
| | | Longest diameter (lesion, solid portion, ground-glass portion), in mm |
| | Overall shape of the lesion and descriptions of its border | Shape, i.e., sphericity (unitless: round=1, oval ~0.5, line=0) / lobulated - irregular / cavitary, speculation, notch/cut |
| | | Margin, i.e., Lesion margin scale (HU), Lesion margin window (HU/mm) |
| | | Topology, i.e., Euler Number |
| | Mean development of cell types or lack thereof that make up the lesion (differentiation, organization) | Volume % solid of Lesion (C/T ratio) |
| | | Volume % ground-glass of Lesion |
| | | Solid density, in g/ml |
| | | Ground glass density, in g/ml |
| | | Mass of solid, in g |
| | | Mass of ground glass, in g |
| | Covariance and development of cell types or lack thereof that make up the lesion (differentiation, organization) | SD (variation of solid density), in g/ml |
| | | SD (variation of ground glass), in g/ml |
| | | Pattern, i.e., (pure GGN) / perifissural / part-solid (mixed GGN) / solid |
| | | Solid portion pattern, i.e., Radial intensity distribution 1st and 2nd order statistics (Central / central with ring / diffuse / peripheral) |
| | | Spatial coherence (texture, "clumpiness", localized heterogeneity), i.e., NSM (non-spatial methods); SGLM (spatial gray-level methods) e.g., Haralick; fractal analysis (FA); Lacunarity; filters & transforms (F&I) e.g., Gabor |
| | Measure of Lesion's invasive extent or potential extent | Pleural contact length (AKA arch distance), in mm |
| | | Pleural contact length-to-maximum lesion diameter (unitless) |
| | | Pleural involvement, i.e., displacement from expected location |
| | | Lobe Location, i.e., Upper / middle / lower lobe // right / left |
| | | Lobe centrality, unitless (1 = lobe center, 0 = lobe boundary) |
| | | Airway Involvement/air bronchogram |
| | | Vascular changes, i.e., Dilated / rigid / convergent / tortuous |
| | Response to injurious agent (dystrophic) or caused by deranged metabolism (metastatic) | Volume, in mm³ |
| | | Volume % of Lesion |
| | | Distribution, i.e., Central / peripheral / diffuse |
| | | Pattern, i.e., amorphous / punctuate / reticular / popcorn / laminated |
| | Change assessed between as few as 2 but arbitrarily many timepoints | Pairwise arithmetic difference |
| | | Pairwise ratio |
| | | Pairwise doubling time |
| | | Polynomial fit coefficients |
| | | Non-arithmetic change assessment with registration, e.g., vascular changes |

Figure 30

SYSTEMS AND METHOD FOR COMPUTER-AIDED PHENOTYPING (CAP) USING RADIOLOGIC IMAGES

CROSS-REFERENCE TO RELATED APPLICATIONS

The present application is a continuation-in-part of the co-pending U.S. application Ser. No. 14/959,732, filed on Dec. 4, 2015, which claims priority to U.S. Provisional Application Ser. No. 62/205,295, filed on Aug. 14, 2015; U.S. Provisional Application Ser. No. 62/205,305, filed on Aug. 14, 2015; U.S. Provisional Application Ser. No. 62/205,313, filed on Aug. 14, 2015; U.S. Provisional Application Ser. No. 62/205,322, filed on Aug. 14, 2015; and U.S. Provisional Application Ser. No. 62/219,860, filed on Sep. 17, 2018. The present application also claims priority to U.S. Provisional Application Ser. No. 62/676,975, filed on May 27, 2015 and U.S. Provisional Application Ser. No. 62/771,448, filed on Nov. 26, 2018.

BACKGROUND OF THE INVENTION

The present disclosure related to quantitative imaging and analytics. More specifically, the present disclosure relates to systems and methods for analyzing pathologies utilizing quantitative imaging.

Imaging, particularly with safe and non-invasive methods, represents the most powerful methods for locating the disease origin, capturing its detailed pathology, directing therapy, and monitoring progression to health. Imaging is also an extremely valuable and low-cost method to mitigate these human and financial costs by allowing for appropriate early interventions that are both less expensive and disruptive.

Enhanced imaging techniques have made medical imaging an essential component of patient care. Imaging is especially valuable because it provides spatially- and temporally-localized anatomic and functional information, using non- or minimally invasive methods. However, techniques to effectively utilize increasing spatial and temporal resolution are needed, both to exploit patterns or signatures in the data not readily assessed with the human eye as well as to manage the large magnitude of data in such a way as to efficiently integrate it into the clinical workflow. Without aid, the clinician has neither the time nor often the ability to effectively extract the information content which is available, and in any case generally interprets the information subjectively and qualitatively. Integrating quantitative imaging for individual patient management as well as clinical trials for therapy development requires a new class of decision support informatics tools to enable the medical community to fully exploit the capabilities possible with evolving and growing imaging modalities within the realities of existing work flows and reimbursement constraints.

Quantitative results from imaging methods have the potential to be used as biomarkers in both routine clinical care and in clinical trials, for example, in accordance with the widely accepted NIH Consensus Conference definition of a biomarker. In clinical practice, quantitative imaging is intended to (a) detect and characterize disease, before, during or after a course of therapy, and (b) predict the course of disease, with or without therapy. In clinical research, imaging biomarkers may be used in defining endpoints of clinical trials.

Quantification builds on imaging physics developments which have resulted in improvements of spatial, temporal, and contrast resolution as well as the ability to excite tissues with multiple energies/sequences, yielding diverse tissue-specific responses. These improvements thereby allow tissue discrimination and functional assessment, and are notably seen, for example, in computed tomography (CT), dual energy computed tomography (DECT), spectral computed tomography (spectral CT), computed tomography angiography (CTA), cardiac computed tomography angiography (CCTA), magnetic resonance imaging (MRI), multi-contrast magnetic resonance imaging (multi-contrast MRI), ultrasound (US), and targeted or general contrast agent approaches with various imaging modalities. Quantitative imaging measures specific biological characteristics that indicate the effectiveness of one treatment over another, how effective a current treatment is, or what risk a patient is at should they remain untreated. Viewed as a measurement device, a scanner combined with image processing of the formed images has the ability to measure characteristics of tissue based on the physical principles relevant to a given imaging approach and how differing tissues respond to them. Though the image formation process differs widely across modalities, some generalizations help frame the overall assessment, though exceptions, nuances, and subtleties drive the real conclusions and until and unless they are considered some of the greatest opportunities are missed.

Imaging in the early phases of clinical testing of novel therapeutics contributes to the understanding of underlying biological pathways and pharmacological effects. It may also reduce the cost and time needed to develop novel pharmaceuticals and therapeutics. In later phases of development, imaging biomarkers may serve as important endpoints for clinical benefit and/or as companion diagnostics to help prescribe and/or follow specific patient conditions for personalized therapy. In all phases, imaging biomarkers may be used to select or stratify patients based on disease status, in order to better demonstrate therapeutic effect.

a. Quantitative Medical Imaging:

Enhanced imaging techniques have made medical imaging an essential component of patient care. Imaging is especially valuable because it provides spatially- and temporally-localized anatomic and functional information, using non- or minimally invasive methods. However, techniques to deal with increasing resolution are needed, both to exploit patterns or signatures in the data not readily assessed with the human eye as well as to manage the large magnitude of data in such a way as to efficiently integrate it into the clinical workflow. With newer high-resolution imaging techniques, unaided, the radiologist would "drown" in data. Integrating quantitative imaging for individual patient management will require a new class of decision support informatics tools to enable the community to fully exploit the capabilities of these new tools within the realities of existing work flows and reimbursement constraints.

Additionally, quantitative imaging methods are increasingly important to (i) preclinical studies, (ii) clinical research, (iii) clinical trials, and (iv) clinical practice. Imaging in the early phases of clinical testing of novel therapeutics contributes to the understanding of underlying biological pathways and pharmacological effects. It may also reduce the cost and time needed to develop novel pharmaceuticals and therapeutics. In later phases of development, imaging biomarkers may serve as important endpoints for clinical benefit. In all phases, imaging biomarkers may be used to select or stratify patients based on disease status, in order to better demonstrate therapeutic effect.

Improved patient selection through use of quantitative imaging could reduce the required sample size for a given trial (by increasing the fraction of evaluable patients and/or decreasing the impact of nuisance variables) and help to identify the sub-population that could benefit most from the proposed treatment. This should reduce development time and cost for new drugs, but might also result in reducing the size of the 'target' population accordingly.

Disease isn't simple, and whereas it often manifests itself focally, yet it is often systemic. Multifactorial assessment of objectively relevant tissue characteristics represented as a panel or "profile" of continuous indicators, sometimes ideally proven as a "surrogate" for a future and/or hard to measure but accepted endpoint, has proven to be an effective method across medicine and will do so here. Computer-aided measurement of lesion and/or organ biology and quantification of tissue composition in first- or second-reader paradigms made possible by an interdisciplinary convergence between next generation computation methods for personalized diagnostics based on quantitative imaging assessment of phenotype implemented in an architecture which proactively optimizes interoperability with modern clinical IT systems provides power to the clinician as they manage their patients across the continuum of disease severity for improved patient classification across surgical, medical, and surveillance pathways. More timely and accurate assessments yield improved outcomes and more efficient use of health care resources, benefits that far outweigh the cost of the tool—at a level of granularity and sophistication closer to the complexity of the disease itself rather than holding the assumption that it can be simplified to a level which belies the underlying biology.

b. Phenotyping:

Radiological imaging is generally interpreted subjectively and qualitatively for medical conditions. The medical literature uses the term phenotype as the set of observable characteristics of an individual resulting from the interaction of its genotype with the environment. Phenotype generally implies objectivity, namely that the phenotype may be said as being true rather than subjective. Radiology is well known for its ability to visualize characteristics, and increasingly it may be validated to objective truth standards (U.S. application Ser. No. 14/959,732; U.S. application Ser. No. 15/237,249; U.S. application Ser. No. 15/874,474; and U.S. application Ser. No. 16/102,042). As a result, radiological images may be used to determine phenotype, but adequate means to do so are often lacking.

Advantageously, phenotyping has a truth basis and therefore can be independently and objectively evaluated. Furthermore, phenotyping is already an accepted formalism in the healthcare industry for managing patient therapeutic decisions. Thus, it has a high degree of clinical relevance. Finally, phenotyping is consumer relatable. This allows for both self-advocacy as well as serving as motivator for lifestyle changes.

Early identification of phenotype based on a comprehensive panel of continuous indicators rather than merely as the detection of a single feature would enable prompt intervention to prevent irreversible damage and death. Solutions are critical to preempt events outright or at least to improve the diagnostic accuracy on experiencing signs and/or symptoms. Efficient workflow solutions with automated measurement of structure and quantification of tissue composition and/or hemodynamics may be used to characterize patients at higher risk, who would be treated differently from those who are not. If we tie characteristics of plaque morphology to embolic potential there will be huge clinical implications.

Imaging phenotypes may be correlated gene-expression patterns in association studies. This may have a clinical impact as imaging is routinely used in clinical practice, providing an unprecedented opportunity to improve decision-support in personalized treatments at low cost. Correlating specific imaging phenotypes with large-scale genomic, proteomic, transcriptomic, and/or metabolomic analyses has potential to impact therapy strategies by creating more deterministic and patient-specific prognostics as well as measurements of response to drug or other therapy. Methods for extracting imaging phenotypes to date, however, are mostly empirical in nature, and primarily based on human, albeit expert, observations. These methods have embedded human variability, and are clearly not scalable to underpin high-throughput analysis.

At the same time the convergence of unmet needs to achieve more personalized medicine while not adding cost—indeed, to better control cost through initiatives in preventative medicine, comparative effectiveness, reimbursement approach, and/or avoiding rather than reacting to untoward events present unprecedented pressures on technological advances that not only provide capability but to deliver it in ways that simultaneously reduce cost.

In addition to the problem of phenotype classification (classifying unordered categories) is the problem of outcome prediction/risk stratification (predicting ordinal levels of risk). Both have clinical utility but being the result of different technical device characteristics. Specifically, one does not strictly depend on the other.

Without limiting generality, an example of phenotype classification included clinical relevance is provided below:

Examples manifestations of "Stable Plaque" phenotype of atherosclerosis may be described as follows:

"Healed" disease, low response to intensified anti-statin regime
Fewer balloon/stent complications
Sometimes higher stenosis >50%
Sometimes higher, Deeper Ca
Minimal or no lipid, hemorrhage, and/or ulceration
Smooth appearance
Such plaques generally have a lower adverse event rate than an "Unstable Plaque" phenotype.
Active disease, may have high response to intensified lipid lowering and/or anti-inflammatory regime
More balloon/stent complications
Sometimes lower Stenosis <50%
Low or diffuse Ca, Ca close to lumen, napkin ring sign, and/or microcalcification
Sometimes evidence of more lipid content, thin cap
Sometimes evidence of hemorrhage or intra=plaque hemorrhage (IPH), and/or ulceration Such plaques have been reported to have 3×-4× the adverse event rate compared to Stable phenotypes. These two examples may be assessed at a single patient encounter, but other phenotypes such as "Rapid Progressors" may be determined by comparing the rate of change in characteristics over time, i.e., phenotypes informed by not only what is statically present at one point in time but rather which are determined based on kinetics and/or how things are changing n time.

c. Machine and Deep Learning Techniques:

Deep Learning (DL) methods have been applied, with large success, to a number of difficult Machine Learning (ML) and classification tasks stemming from complex real-life problems. Notable recent applications include computer vision (e.g., optical character recognition, facial recognition, interpretation of satellite imagery, etc.), speech recognition, natural language processing, medical images analysis (image segmentation, feature extraction, and classification), clinical and molecular data biomarkers discovery and verification. An attractive feature of the approach is its ability to be applied to both unsupervised and supervised learning tasks.

Neural Networks (NN), and the Deep NN approach, broadly including convolutional neural networks (CNNs), recurrent convolutional neural networks (RCNNs), etc., have been shown to be based on a sound theoretical foundation, and are broadly modelled after principles believed to represent the high-level cognition functions of the human brain. For example, in the neocortex, a brain region associated with many of cognitive abilities, the sensory signals propagate thru a complex local, modular hierarchy which learns to represent observations over time—a design principle that has led to the general definition and construction of CNNs used for i.e. image classification and feature extraction. However, it has been somewhat of an undecided question what are the more fundamental reasons for the superior performance of the DL networks and approach compared to frameworks with the same number of fitting parameters but without the deep layered architecture.

Conventional ML approaches to image feature extraction and image-based learning from raw data have a multitude of limitations. Notably, spatial context is often difficult to obtain in ML approaches using feature extraction when features are at a summary level rather than at the 3D level of the original image, or when they are at the 3D level, to the extent that they are not tied to a biological truth capable of being objectively validated but just being mathematical operators. Use of raw data sets that do contain spatial context often lack objective ground truth labels for the extracted features, but use of raw image data itself include much variation that is "noise" with respect to the classification problem at hand. In applications outside of imaging, this is usually mitigated by very large training sets, such that the network training "learns" to ignore this variation and only focus on the significant information, but large training sets of this scale are not generally available in medical applications, especially data sets annotated with ground truth, due to cost, logistics, and privacy issues. The systems and methods of the present disclosure help overcomes these limitations.

d. Example Application: Cardiovascular Measures Such as Fractional Flow Reserve (FFR) and Plaque Stability or High-Risk Plaque (HRP):

New treatments have been revolutionary in improving outcomes over the last 30 years, yet cardiovascular disease still exerts a $320B annual burden on the US economy. There is a substantial patient population that could benefit from better characterization of risk of major adverse coronary or cerebral events. American Heart Association (AHA), extrapolating ACSD (atherosclerotic cardiovascular disease) risk scores to the population projects that 9.4% of all adults (age >20) have a greater than 20% risk of adverse events in the next 10 years and 26% have between 7.5% and 20% risk. Applying this to the population yields 23M high risk patients and 57M moderate risk patients. The 80M at risk can be compared to the 30M U.S. patients are currently on statin therapy in an attempt to avoid new or recurrent events and the 16.5M with a CVD diagnosis. Of those on statins, some will develop occlusive disease and acute coronary syndrome (ACS). The vast majority of patients are unaware of their disease progression until onset chest pain. Further outcome and cost improvements in coronary artery disease will flow from improved noninvasive diagnostics to identify which patients have progressing disease under first line treatments.

Heart health can be significantly impacted by the degradation of arteries surrounding the heart. A variety of factors (tissue characteristics such as angiogenesis, neovascularization, inflammation, calcification, lipid-deposits, necrosis, hemorrhage, rigidity, density, stenosis, dilation, remodeling ratio, ulceration, flow (e.g., of blood in channel), pressure (e.g., of blood in channel or one tissue pressing against another), cell types (e.g., macrophages), cell alignment (e.g., of smooth muscle cells), or shear stress (e.g., of blood in channel), cap thickness, and/or tortuosity (e.g., entrance and exit angles) by way of example) may cause these arteries to reduce their effectiveness in transmitting oxygen filled blood to the surrounding tissue (FIG. 35).

Functional testing of the coronary arteries, mainly stress-echocardiography and single photon emission computed tomography myocardial perfusion testing (SPECT MPI), is currently the dominant noninvasive method for diagnosing obstructive coronary artery disease. Over ten million functional tests are performed each year in the United States with positive results driving 2.6M visits to the catheter lab for invasive angiography to confirm the finding of coronary artery disease.

Another approach to assessing perfusion is to determine the vasculature's ability to transmit oxygen. Specifically, reduced ability can be quantified as fractional flow reserve, or FFR. FFR is not a direct measure of ischemia, but rather is a surrogate that measures a ratio in pressure drop across the lesion. Changes in luminal diameter relative to other segments of the same vessel, caused by local vasodilatory impairment at the time of maximal hyperemia, produces a marked hemodynamic effect, leading to abnormal FFR measurement. During physical FFR measurement, the infusion of adenosine decreases downstream resistance to allow increased flow in the hyperemic state. Physically measuring FFR requires an invasive surgical procedure involving a physical pressure sensor within the arteries. Because this level of invasiveness lends itself to risk and inconvenience there is a demand for methods that estimate FFR with high accuracy without the need for physical measurement. The ability to perform this measurement non-invasively also decreases a noted "treatment bias": once a patient is in the cath lab, stenting is relatively easy to do so many have noted that overtreatment occurs whereas if the flow reserve could be assessed non-invasively, improved decisions on whether to stent or not stent could be possible. Likewise, flow reserve applies to perfusion of brain tissues as well (e.g., as related to hyperemia in the brain).

Functional testing has known issues with sensitivity and specificity. It is estimated that some 30-50% of cardiovascular disease patients are misclassified and are over-treated or under-treated with significant monetary and quality of life costs. Functional testing is also expensive, time consuming and of limited use with patients that have pre-obstructive disease. False positives from non-invasive function tests are a large factor in the overuse of both invasive coronary angiography and percutaneous coronary interventions in stable patients that are a major policy issue in the U.S., Great Britain and China. Studies of the impact of false negatives estimate that of 3.8M annual MPI tests given to U.S. patients with suspected coronary artery disease (CAD), close to 600,000 will report false negative findings leading to 13,700 acute coronary events, many of which would be preventable just through introduction of appropriate drug therapies. Another deficiency of functional testing is temporal in nature: Ischemia is a lagging indicator that follows the anatomical changes brought on by disease progression. Patients at high risk for ACS would also be better served if future culprit lesions can be detected and reduced with intensive drug therapy prior to the onset of ischemia.

Coronary computed tomography angiography (CCTA), especially when utilized in tandem with quantitative analysis software is evolving into an ideal testing modality to fill this gap in understanding the extent and rate of progression coronary artery disease. Over the last 10 years the CT scanner fleet in most countries has been upgraded to higher-speed, higher detector count machines capable of excellent spatial resolution without slowing of the heart or extensive breath-holds. Radiation dose has been greatly lowered, to the point where it is equivalent or lower than SPECT MPI and invasive angiography.

Recent analyses of data from landmark trials like SCOT-HEART, PREDICT, and PROMISE and others have demonstrated the value of detecting non-obstructive disease, sometimes referred to as high-risk plaque (HRP) or vulnerable plaque, using CCTA, by identifying patients who are at increased risk for future adverse events. Study designs were varied and included nested case-controlled cohorts comparing CCTA registry patients with cardiovascular (CV) events to controls with similar risk factors/demographics, comparisons to FFR and multi-year follow-ups to large "test and treat" studies. The recent favorable determination from NICE positioning CCTA as a front-line diagnostic is based on a significant reduction in CV events in the CCTA arm of the SCOT-HEART study that was attributed to drug treatment initiation or changes on discovery of plaques with CCTA.

An important target patient group are those with stable chest pain and no prior history of CAD with typical or atypical anginal symptoms (based on SCOT-HEART data), and those with those with non-obstructive disease (<70% stenosis) and in younger patients (e.g., 50-65 years group), based on the PROMISE findings that suggest that assessment of plaque is most needed. Patients with non-obstructive CAD found with high-risk plaque profile based on CCTA analysis can be assigned to most appropriate high intensity statin therapy (particularly when a decision on new lipid-lowing therapies that are very expensive such as PCSK9 inhibitors, or anti-inflammatory drugs such as canakinumab are considered), or add a new antiplatelet agent to mitigate the risk of coronary thrombosis, and/or longitudinal follow-up for possible intensification or downgrading of the therapies. CCTA is an ideal diagnostic tool as it is noninvasive and requires less radiation than cardiac catheterization.

The pathology literature regarding culprit lesions implicated in fatal heart attacks note that clinically non-obstructive CAD is much more likely to be home to most high-risk plaque than more occlusive plaques which tend to be more stable. These findings were corroborated by a recent study which noted culprit lesions from ACS patients undergoing invasive angiography and compared them to precursor plaques in the baseline CCTA. In one cohort receiving clinically indicated CCTA, patients found to have non-obstructive CAD, 38% of those so tested, still have significant risk of medium to long-term major adverse cardio and/or cerebrovascular events (MACCE). The hazard ratio based on the number of diseased segments, independent of obstruction was found to be a significant long-term predictor of MACCE in this group. One contributing factor to the predictive value of clinically non-obstructive CAD is that these lesions much more likely to be home to most high-risk plaque than more occlusive plaques which tend to be more stable.

Further demonstration of the potential utility of CCTA in detecting and managing obstructive and pre-obstructive atherosclerotic lesions is seen in several recently-published longitudinal studies of statin and anti-inflammatory drug treatment effects, where plaque remodeling to more stable presentations and plaque regression were observed in the treatment arms. This corroborates the body of earlier intravascular ultrasound (IVUS, sometimes with "virtual histology" VH), near-infra red spectroscopy (NIRS), optical coherence tomography (OCT), etc., studies that explored disease progression and treatment effect under a variety of lipid reducing drug protocols. Recent drug trials provide potential plaque biomarkers to demonstrate efficacy of new medical therapies. The Integrated Biomarkers and Imaging Study-4 (IBIS-4) found progression of calcification as a potentially protective effect of statins. Other studies found reduction in lipid-rich necrotic core (LRNC) under statin treatment. In these studies, clinical variables had poor discrimination of identifying high-risk plaque characteristics when used alone. The studies stress the importance of complete characterization and assessment of the entire coronary tree, instead of just the culprit lesion, to allow more accurate risk stratification, which suitably analyzed CCTA can do. In a meta-analysis, CCTA had good diagnostic accuracy to detect coronary plaques compared to IVUS with small differences in assessment of plaque area and volume, percent area stenosis, and slight overestimation of lumen area. Adding rate of change of lipid rich necrotic core and its distance from the lumen was also found to have high prognostic value. Additionally, results from the ROMICAT II Trial show that identifying high-risk plaque on CCTA for stable CAD patients with acute chest pain but negative initial ECG and troponin increases the likelihood of ACS independent of significant CAD and clinical risk assessment. Examination by CCTA has been established for evaluation of the coronary atherosclerotic plaques. For patients where the necessity of invasive procedures is uncertain, predicting MACCE non-invasively would be beneficial and feasible with CCTA which gives an overall estimate of disease burden and risk of future events.

The prevalence of carotid artery disease and CAD are closely related. Carotid atherosclerosis has been shown to be an independent predictor for MACCE, even in patients without pre-existing CAD. Such findings suggest a common underlying pathogenesis shared in both conditions, which is further supported by the Multi-Ethnic Study of Atherosclerosis (MESA). Atherosclerosis develops progressively through evolution of arterial wall lesions resulting from the accumulation of cholesterol-rich lipids and inflammatory response. These changes similar (even if not identical) in the coronary arteries, the carotid arteries, aorta, and peripheral arteries. Certain plaque characteristics such as large atheromatous core with lipid-rich content, thin cap, outward remodeling, infiltration of the plaque with macrophages and lymphocytes and thinning of the media are predisposing to vulnerability and rupture.

e. Non-Invasive Determination of HRP and/or FFR:

Non-invasive assessment of the functional significance of stenosis using CCTA is of clinical and financial interest. The combination of a lesion or vessel's geometry or anatomic structure together with the characteristics or composition of the tissue comprising the walls and/or plaque in the walls, collectively referred to as plaque morphology, may explain outcomes in lesions with higher or lower risk plaque (HRP) and or the orthogonal consideration of normal and abnormal flow reserve (FFR). Lesions with a large necrotic core may develop dynamic stenosis due to outward remodeling during plaque formation resulting in more tissue to stretch, the tissue being stiffer, or the smooth muscle layer being already stretched to the limits of Glagov phenomenon, after which the lesions encroach on the lumen itself. Likewise, inflammatory insult and/or oxidative stress could result in local endothelial dysfunction, manifest as impaired vasodilative capacity.

If the tissue making up the plaque is mostly matrix or "fatty streaks" that are not organized into a necrotic core, the plaque dilates sufficiently to keep up with the demand. However, if the plaque has a more substantial necrotic core, it won't be able to dilate. Blood supply will not be able to keep up with the demand. Plaque morphology increases accuracy by evaluating complex factors such as LRNC, calcification, hemorrhage, and ulceration with an objective truth that may be used to validate the underlying information, in a manner that other approaches cannot due to the lack of an intermediate measurement objective validation.

But that isn't all a plaque can do. Too often, plaques actually rupture, suddenly causing a clot which then may result in infarction of heart or brain tissue. Plaque morphology also identifies and quantifies these high-risk plaques. For example, plaque morphology may be used to determine how close the necrotic core is to the lumen: a key determinant of infarction risk. Knowing whether a lesion limits flow under stress doesn't indicate the risk of rupture or vice versa. Other methods such as computational fluid dynamics (CFD), without objectively validated plaque morphology, can simulate flow limitation but not infarction risk. The fundamental advantage of plaque morphology is that its accuracy lies in both the determination of vessel structure and tissue characteristics, together allowing determination of phenotype.

Clinical guidelines are increasingly available regarding the optimal management of patients with differing assessments of flow reserve. It is known that obstructive lesions with high-risk features (large necrotic core and thin cap) portend a maximum likelihood of future events and importantly, the converse holds true as well.

Without accurate assessments of plaque morphology, approaches to determine FFR using CFD have been published. But CFD-based flow reserve considers the lumen only, or at best, how the luminal surface changes at different parts of the cardiac cycle. Considering only the luminal surface at best requires processing both systolic and diastolic to get motion vector (which isn't even done by most available methods), but even that does not consider what occurs at stress, because these analyses are done with computer simulations of what may happen under stress rather than measuring actual stress, and not based on the actual characteristics that originate vasodilatory capacity but rather just the blood channel. Some methods attempt to simulate forces and apply biomechanical models, but with assumptions rather than validated measurements of wall tissues. Consequently, these methods have no ability to anticipate what can occur if stress in fact causes rupture beyond rudimentary assumptions. Rather, characterizing the tissue solves these problems. Wall characteristics, including its effect on vasodilatory capacity of the vessel due to the distensibility of its walls is considered superior in that lesion makeup determines pliability and energy absorption, stable lesions are still over treated, and incomplete assessment of MACCE risk. The advantages of using morphology to assess FFR include the fact that morphology is a leading indicator, FFR lags, and that presence and degree of HRP better informs treatment for borderline subjects. The importance of solving accurate assessment by morphology is strengthened by the studies increasingly show that morphology can predict FFR but that FFR does not predict morphology. That is, effectively assessed morphology has not only the ability to determine FFR but as well as the likelihood of discontinuous changes in the plaque that move the patient from ischemia to infarction or HRP.

SUMMARY

Systems and methods are provided herein which utilize a hierarchical analytics framework to identify and quantify biological properties/analytes from imaging data and then identify and characterize one or more medical conditions based on the quantified biological properties/analytes. In some embodiments, the systems and methods incorporate computerized image analysis and data fusion algorithms with patient clinical chemistry and blood biomarker data to provide a multi-factorial panel that may be used to distinguish between different subtypes of disease. Thus, the systems and methods of the present disclosure may advantageously implement biological and clinical insights in advanced computational models. These models may then interface with sophisticated image processing through rich ontologies that specify factors associated with the growing understanding of pathogenesis and takes the form of rigorous definitions of what is being measured, how it is measured and assessed, and how it is relates to clinically-relevant subtypes and stages of disease that may be validated.

Human disease exhibits strong phenotypic differences that can be appreciated by applying sophisticated classifiers on extracted features that capture spatial, temporal, and spectral results measurable by imaging but difficult to appreciate unaided. Traditional Computer-Aided Diagnostics make inferences in a single step from image features. In contrast, the systems and methods of the present disclosure employ a hierarchical inference scheme including intermediary steps of determining spatially-resolved image features and time-resolved kinetics at multiple levels of biologically-objective components of morphology, composition and structure which are subsequently utilized to draw clinical inferences. Advantageously, the hierarchical inference scheme ensures the clinical inferences can be understood, validated, and explained at each level in the hierarchy.

Thus, in example embodiments, systems and methods of the present disclosure utilize a hierarchical analytics framework comprised of a first level of algorithms which measure biological properties capable of being objectively validated against a truth standard independent of imaging, followed by a second set of algorithms to determine medical or clinical conditions based on the measured biological properties. This framework is applicable to a number of distinct biological properties in an "and/or" fashion, i.e., singly or in combination, such as angiogenesis, neovascularization, inflammation, calcification, lipid-deposits, necrosis, hemorrhage, rigidity, density, stenosis, dilation, remodeling ratio, ulceration, flow (e.g., of blood in channel), pressure (e.g., of blood in channel or one tissue pressing against another), cell types (e.g., macrophages), cell alignment (e.g., of smooth muscle cells), or shear stress (e.g., of blood in channel), cap thickness, and/or tortuosity (e.g., entrance and exit angles) by way of examples. Measurands for each of these may be measured, such as quantity and/or degree and/or character, of the property. Example conditions include perfusion/ischemia (e.g., as limited) (e.g., of brain or heart tissue), perfusion/infarction (as cut off completely) (e.g., of brain or heart tissue), oxygenation, metabolism, flow reserve (ability to perfuse), malignancy, encroachment, and/or risk stratification (whether as probability of event, or time to event (TTE)) e.g., major adverse cardio- or cerebrovascular events (MACCE). Truth bases may include, for example, biopsy, expert tissue annotations form excised tissue (e.g., endarterectomy or autopsy), expert phenotype annotations on excised tissue (e.g., endarterectomy or autopsy), physical pressure wire, other imaging modalities, physiological monitoring (e.g., ECG, SaO2, etc.), genomic and/or proteomic and/or metabolomics and/or transcriptomic assay, and/or clinical outcomes. These properties and/or conditions may be assessed at a given point in time and/or change across time (longitudinal).

In example embodiments, the systems and methods of the subject application, advantageously relate to computer-aided phenotyping (CAP) of disease. CAP is a new and exciting complement to the field of computer-aided diagnosis (CAD). As disclosed herein, CAP may apply a hierarchical inference incorporating computerized image analysis and data fusion algorithms to patient clinical chemistry and blood biomarker data to provide a multi-factorial panel or "profile" of measurements that may be used to distinguish between different subtypes of disease that would be treated differently. Thus, CAP implements new approaches to robust feature extraction, data integration, and scalable computational strategies to implement clinical decision support. For example, spatio-temporal texture (SpTeT) method captures relevant statistical features for characterizing tissue spatially as well as kinetically. Spatial features map, for example, to characteristic patterns of lipid intermixed with extracellular matrix fibers, necrotic tissue, and/or inflammatory cells. Kinetic features map, for example, to endothelial permeability, neovascularization, necrosis, and/or collagen breakdown.

In contrast to current CAD approaches, which make clinical inferences in a single step of machine classification from image features, the systems and methods of the subject application may advantageously utilize a hierarchical inference scheme may be applied beginning with not only spatially-resolved image features but also time-resolved kinetics at multiple levels of biologically-objective components of morphology and structural composition in the middle, and then clinical inference at the end. This results in a system that can be understood, validated, and explained at each level in the hierarchy from low-level image features at the bottom to biological and clinical features at the top.

The systems and methods of the present disclosure improve upon both phenotype classification and outcome prediction. Phenotype classification may occur at two levels, individual anatomic locations on the one hand and more generally described body sites on the other. The input data for the former may be 2D data sets, and the input data for the latter may be 3D data sets. Whereas for phenotype classification objective truth may be at either level, for outcome prediction/risk stratification generally occurs at the patient level, but can be more specific in certain instances (e.g., which side did stroke symptoms manifest on). The implication here is that the same input data may be used for both purposes, but the models will differ substantially because of the level at which the input data will be used as well as the basis of the truth annotations.

While it is possible to perform model building readings vector as input data, performance is often limited by the implemented measurands. The subject application advantageously utilizes unique measurands (e.g., cap thickness, calcium depth, and ulceration) to improve performance. Thus, a readings vector-only approach may be applied where the vector is inclusive of these measurands (e.g., in combination with conventional measurands). The systems and methods of the present disclosure, however, may advantageously utilize a Deep Learning (DL) approach, however, which can provide an even richer data set. The systems and methods of the subject application may also advantageously utilize an unsupervised learning application, thereby providing for better scalability across data domains (a very highly desirable feature having in mind the pace at which new biomedical data is generated).

In example embodiments, presented herein, Convolutional neural networks (CNNs) may be utilized for building a classifier in an approach that can be characterized as transfer-learning with fine-tuning approach. CNNs trained on a large compendium of imaging data on a powerful computational platform can be used, with a good success, to classify images that have not been annotated in the network training. This is intuitively understandable, as many common classes of features help identify images of vastly different objects (i.e. shapes, boundaries, orientation in space, etc.). It is then conceivable that CNNs trained to recognize thousands of different objects using pre-annotated datasets of tens of millions of images would perform basic image recognition tasks much better than chance, and would have a comparable performance to CNNs trained from scratch after a relatively minor tweaking of the last classification layer, sometimes referred to as the softmax layer. Since these models are very large and have been trained on a huge number of pre-annotated images, they tend 'to learn' very distinctive, discriminative imaging features. Thus, the convolutional layers can be used as a feature extractor or the already trained convolutional layers can be tweaked to suit the problem at hand. The first approach is referred to as transfer learning and the latter as fine-tuning.

CNNs are excellent at performing many different computer vision tasks. CNNs have a few drawbacks however. Two important drawbacks of importance to medical systems are 1) the need for vast training and validation datasets, and 2) intermediate CNN computations are not representative of any measurable property (sometimes criticized as being a "black box" with undescribed rationale). The approaches disclosed herein may advantageously utilize a pipeline consisting of one or more stages which are separately biologically measurable and capable of independent validation, followed by a convolutional neural network starting from these rather than only raw imagery. Moreover, certain transforms may be applied to reduce variation that does not relate to the problem at hand, such as for example unwrapping a donut-shaped vessel cross section to become a rectangular representation with a normalized coordinate system prior to feeding the network. These front-end pipeline stages simultaneously alleviate both of the two drawbacks of using CNNs for medical imaging.

Generally, the early convolutional layers act as feature extractor of increasing specificity, and the fully connected one or two last layers act as classifiers (e.g., "softmax layers"). Schematic representations of layers sequence and their function in a typical CNN is available from many sources.

Advantageously, the systems and methods of the present disclosure utilize enriched data sets to enable non-invasive phenotyping of tissues assayed by radiological data sets. One type of enrichment is to pre-process the data to perform tissue classification and use "false color" overlays to provide a data set that can be objective validated (as opposed to only using raw imagery, which does not have this possibility). Another type of enrichment is to use transformations on the coordinate system, to accentuate biologically-plausible spatial context while removing noise variation to either improve the classification accuracy, allow for smaller training sets, or both.

In example embodiments, the systems and methods of the subject application may employ a multi-stage pipeline: (i) semantic segmentation to identify and classify regions of interest (e.g., which may be representative of quantitative biological analytes) (ii) spatial unwrapping to convert cross-sections of a tubular structure (e.g., a vein/artery cross section) into rectangles, and (iii) application of a trained CNN to read the annotated rectangles and identify which phenotype (e.g., stable or unstable plaque and/or normal or abnormal FFR) it pertains to, and/or predicted time to event (TTE). Note that by training and testing a CNN with an unwrapped dataset (with unwrapping) vs a donut dataset (without unwrapping) it can be demonstrated that unwrapping improves validation accuracy for each particular implementation. Thus, various implementations imaging of tubular structures (e.g., plaque phenotyping) or other structures (e.g., lung cancer mass subtyping), or other applications, may similarly, benefit from performing similar steps (e.g., semantic segmentation followed by spatial transformations such as unwrapping (prior to applying a CNN). However, it is contemplated that in some alternative embodiments, that untransformed datasets (e.g., datasets that are not spatially unwrapped, for example) may be used in determining phenotype (e.g., either in conjunction with or independent of untransformed datasets).

In example embodiments, semantic segmentation and spatial transformation may involve the following: The image volume may be preprocessed including target initialization, normalization, and any other desired pre-pressing such as deblurring or restoring to form a region of interest containing a physiological target that is to be phenotyped. Notably, said region of interest may be a volume composed of cross sections through that volume. is the body site may be either automatically determined or is provided explicitly by user. Targets for body sites that are tubular in nature may be accompanied with a centerline. Centerlines, when present, can branch. Branches can be labelled either automatically or by user. Note that generalizations on the centerline concept may be represented for anatomy that is not tubular but which benefit by some structural directionality, e.g., regions of a tumor. In any case, a centroid may be determined for each cross section in the volume. For tubular structures this may be the center of the channel, e.g., the lumen of a vessel. For lesions this may be the center of mass of the tumor. The (optionally deblurred or restored) image may be represented in a Cartesian data set where x is used to represent how far from centroid, y represents a rotational theta, and z represents the cross section. One such Cartesian set will be formed per branch or region. When multiple sets are used, a "null" value may be used for overlapping regions, that is, each physical voxel may be represented only once across the sets, in such a way as to geometrically fit together. Each data set can be paired with an additional data set with sub-regions labelled by objectively verifiable tissue composition. Example labels for vascular tissue can be lumen, calcification, LRNC, IPH, etc. Example labels for lesions could be necrotic, neovascularized, etc. These labels can be validated objectively, e.g. by histology. Paired data sets may can used as input to a training step to build a convolutional neural network. In example embodiments, two levels of analysis can be supported, one at an individual cross-section level, and a second at the volume level. Output labels represent phenotype or risk stratification.

Exemplary image pre-processing may include deblurring or restoring using, for example, a patient-specific point spread determination algorithm to mitigate artifacts or image limitations that result from the image formation process. These artifacts and image limitations may decrease the ability to determine characteristics predictive of the phenotype. Deblurring or restoring may be achieved as a result of, for example, iteratively fitting a physical model of the scanner point spread function with regularizing assumptions about the true latent density of different regions of the image.

In example embodiments, the CNN may be AlexNet, Inception, CaffeNet, or other networks. In some embodiments, refactoring may be done to the CNN, e.g., where a same number and type of layers are used, but the input and output dimensions are changed (such as to change the aspect ratio). Example implementations of various example CNNs are provided as open source on, for example, TensorFlow, and/or in other frameworks, available as open source and/or licensed configurations.

In example embodiments, the dataset may be augmented. For example, in some embodiments, 2D or 3D rotations may be applied to the dataset. Thus, in the case of a untransformed (e.g., donut) dataset, augmentation may involve, e.g., randomly horizontally flipping the dataset in conjunction with randomly rotating the data set (such as by a random angle between 0 and 360 degrees). Similarly, in the case of an transformed (e.g., unwrapped) dataset, augmentation may involve e.g., randomly horizontally flipping in conjunction with a random "scrolling" of the image such as by a random number of pixels in the range from 0 to the width of the image (where scrolling akin to rotating around theta).

In example embodiments, the dataset may be enriched by using different colors to represent different tissue analyte types. These colors may be selected to visually contrast relative to each other, as well as relative to a non-analyte surface (e.g., normal wall). In some embodiments, a non-analyte surface may be depicted in grey. In example embodiments, dataset enrichment may result in ground truth annotation of tissue characteristics (e.g., tissue characteristics that are indicative of plaque phenotype) as well as provide a spatial context of how such tissue characteristics present in cross section (e.g., such as taken orthogonal to an axis of the vessel). Such spatial context may include a coordinate system (e.g., based on polar coordinates relative to a centroid of the cross-section) which provides a common basis for analysis of dataset relative to histological cross sections. Thus, enriched datasets may be advantageously overlaid on top of color-coded pathologist annotations (or vice versa). Advantageously, a histology based annotated dataset may then be used for training (e.g., training of the CNN) in conjunction with or independent of image feature analysis of a radiological dataset. Notably, a histology based annotated dataset, may improve efficiency in DL approaches since the histology based annotated dataset uses a relatively simpler false color image in place of a higher-resolution full image without losing spatial context. In example embodiments, coordinate directions may be internally represented using unit phasors and phasor angle. In some embodiments, the coordinate system may be normalized, e.g., by normalizing the radial coordinate with respect to wall thickness (such as to provide a common basis for comparing tubular structures/cross-sections of different diameters/thicknesses). For example, a normalized radial distance may have a value of 0 at an inner (inner wall luminal boundary) and value of 1 at an outer boundary (outer wall boundary). Notably, this may be applied to tubular structures relevant to vascular or other pathophysiology (e.g., the gastro-intestinal tract).

Advantageously, the enriched datasets of the subject application provide for in vivo non-invasive image-based classification (e.g., where a tissue classification scheme can be used to determine phenotype non-invasively) which is based on a known ground truth. In some embodiments, the known ground truth may be non-radiological (such as histology or another ex vivo based tissue analysis). Thus, for example, radiology datasets annotated to include ex vivo ground truth data (such as histology information) may be advantageously used as input data for the classifier. In some embodiments, a plurality of different known ground truths may be used in conjunction with one another or independent of one another in annotating an enriched dataset.

As noted herein, in some embodiments, an enriched dataset may utilize a normalized coordinate system to avoid non-relevant variation associated with, for example, the wall thickness and radial presentation. Furthermore, as noted herein, in example embodiments, a "donut" shaped dataset may be "unwrapped," e.g., prior to classification training (e.g., using a CNN) and/or prior to running a training classifier on the dataset. Notably, in such embodiments, analyte annotation of the training dataset may be prior to transformation, e.g., after unwrapping or a combination of both. For example, in some embodiments, an untransformed dataset may be annotated (e.g., using ex vivo classification data such as histology information) and then transformed for classifier training. In such embodiments, a finer granularity of ex vivo based classification may be collapsed to match a lower intended granularity for in vivo radiology analysis to not only decrease computational complexity but simulataneously address what would otherwise be open to criticism of being a "black box".

In some embodiments, colors and/or axes for visualizing the annotated radiological dataset may be selected to correspond to the same colors/axes as typically presented in ex vivo ground truth-based classifications (e.g., same colors/axes as used in histology). In example embodiments, a transformed enriched dataset (e.g., which may be normalized for wall thickness) may be presented where each analyte is visually represented by a different contrasting color and relative to a background region (e.g., black or grey) for all non analyte regions. Notably, depending on the embodiment the common background may or may not be annotated and therefore may or may not visually differentiate between non-analyte regions in and out of the vessel wall or between background features (such as luminal surface irregularity, varying wall thickness, etc.). Thus, in some embodiments, annotated analyte regions (e.g., color coded and normalized for wall thickness) may be visually depicted relative to a uniform (e.g., completely black, completely gray, completely white, etc.) background. In other embodiments, annotated analyte regions (e.g., color coded but not normalized for wall thickness) may be visually depicted relative to an annotated background (e.g., where different shades (grey, black and/or white) may be used to distinguish between (i) a center lumen region inside the inner lumen of the tubular structure, (ii) non-analyte regions inside the wall and/or (iii) a region outside the outer wall. This may enable analysis of variations of wall thickness (e.g., due to ulceration or thrombus). In further example embodiments, the annotated dataset may include, e.g., identification of (and visualization of) regions of intra-plaque hemorrhage and/or other morphology aspects. For example, regions of intra-plaque hemorrhage may be visualized in red, LRNC in yellow, etc.

One specific implementation of the systems and methods of the subject application may be in directing vascular therapy. Classifications may be established according to a likely dynamic behavior of a plaque lesion (based on its physical characteristics or specific mechanisms e.g. inflammatory or cholesterol metabolism based) and/or based on a progression of the disease (e.g., early vs late in its natural history). Such classifications may be used for directing patient treatment. In example embodiments, the Stary plaque typing system adopted by the AHA may be utilized as an underlay with in vivo determined types shown in color overlays. An example mapping is ['I', 'II', 'III', 'IV', 'V', 'VI', 'VII', 'VIII'] yielding class_map=[Subclinical, Subclinical, Subclinical, Subclinical, Unstable, Unstable, Stable, Stable]. The systems and methods of the present disclosure are not, however, tied to Stary. as another example, the Virmani system ['Calcified nodule', 'CTO', 'FA', 'FCP', 'Healed Plaque Rupture', 'PIT', 'IPH', 'Rupture', 'TCFA', 'ULC'] has been used with class_map= [Stable, Stable, Stable, Stable, Stable, Stable, Unstable, Unstable, Unstable, Unstable], and other typing systems may yield similarly high performance. In example embodiments, the systems and methods of the present disclosure may merge disparate typing systems, the class map may be changed, or other variations. For FFR phenotypes, values such as normal or abnormal may be used, and/or numbers may be used, to facilitate comparison with physical FFR for example.

Thus, in example embodiments, the systems and methods of the present disclosure may provide for phenotype classification of a plaque based on an enriched radiological data set. In particular, the phenotype classification(s) may include distinguishing stable plaque from unstable plaque, e.g., where the ground truth basis for the classification is based on factors such as (i) luminal narrowing (possibly augmented by additional measures such as tortuosity and/or ulceration), (ii) calcium content (possibly augmented by depth, shape, and/or other complex presentations), (iii) lipid content (possibly augmented by measures of cap thickness and/or other complex presentations), (iv) anatomic structure or geometry, and/or (v) IPH or other content. Notably, this classification has been demonstrated to have high overall accuracy, sensitivity and specificity as well as a high degree of clinical relevance (with potential to change existing standard of care of patients who are undergoing catheterization and cardiovascular care).

Another example implementation is lung cancer where the subtypes of masses may be determined so as to direct the most likely beneficial treatment for the patient based on the manifest phenotype. In particular, pre-processing and dataset enrichment may be used to separate out into solid vs. semi-solid ("ground glass") sub regions, which differ both in degree of malignancy as well as suggesting differing optimal treatments.

In further example embodiments, the systems and methods of the present disclosure may provide for image pre-processing, image de-noise and novel geometric representation (e.g., an affine transformation) of CT angiography (CTA) diagnostic images to facilitate and maximize performance of Deep Learning Algorithms based on CNNs for developing best-of-class classifier and a marker of risk of adverse cardiovascular effects during representation procedures. Thus, as disclosed herein, image deblurring or restoring may be used to identify lesions of interest and extract plaque composition quantitatively. Furthermore, transformation of cross-sectional (along the main axis blood vessel) segmented images into, for example, an 'unwrapped' rectangular reference frame which follows the established lumen along the X axis may be applied to provide a normalized frame to allow DL approaches to best learn representative features.

While example embodiments herein utilize 2-D annotated cross-sections for analysis and phenotyping it is noted that the subject application is not limited to such embodiments. In particular, some embodiments may utilize enriched 3-D datasets, e.g., instead of or in addition to processing 2-D cross-sections separately. Thus, in example embodiments, video interpretation from computer vision may be applied for the classifier input data set. Note that processing multiple cross-sections sequentially, as if in a "movie" sequence along a centerline, can generalize these methods for tubular structures, e.g., moving up and down a center-line, and/or other 3D manifestations depending on the aspects most suited to the anatomy.

In further example embodiments false color representations in the enriched data set may have continuous values across pixel or voxel locations. This can be used for, "radiomics" features, with or without explicit validation, or validated tissue types, independently calculated for each voxel. Such a set of values may exist in an arbitrary number of pre-processed overlays and may be fed into the phenotype classifier. Notably, in some embodiments, each pixel/voxel can have values for any number of different features (e.g., can be represented in any number of different overlays for different analytes, sometimes referred to as "multiple occupancy"). Alternatively, each pixel/voxel may only be assigned to one analyte (e.g., assigned to only a single analyte overlay). Furthermore, in some embodiments, the pixel/voxel value for a given analyte (e.g., a given analyte) can be based on an all or nothing classification scheme (e.g., either the pixel is calcium or it isn't). Alternatively, the pixel/voxel value for a given analyte can be a relative value, e.g., a probability score). In some embodiments, the relative values for a pixel/voxel are normalized across a set of analytes (e.g., so that the total probability adds up to 100%).

In example embodiments, classification models may be trained in whole or in part by application of multi-scale modeling techniques, such as for example partial differential equations, e.g., to represent likely cell signaling pathways or plausible biologically-motivated presentations.

Other alternative embodiments include using change data, for example as collected from multiple timepoints, rather than (only) data from a single timepoint. For example, if the amount or nature of a negative cell type increased, it may be said to be a "progressor" phenotype, vs. a "regressor" phenotype for decreases. The regressor might be, for example, due to response to a drug. Alternatively, if the rate of change for, say, LRNC is rapid, this may imply a different phenotype, e.g., a "rapid progressor".

In some embodiments, non-spatial information, such as which are derived from other assays (e.g., lab results), or demographics/risk factors, or other measurements taken from the radiological image, may be fed into the final layers of the CNN to combine the spatial information with non-spatial information.

Notably while the systems and methods focus on phenotype classification, similar approaches may be applied with respect to outcome prediction. Such classifications may be based on ground truth historical outcomes assigned to training data sets. For example, life expectancy, quality of life, treatment efficacy (including comparing different treatment methods), and other outcome predictions can be determined using the systems and methods of the subject application.

Examples of the systems and methods of the subject application are further illustrated in the plurality of drawings and the detailed description which follows.

In further example embodiments, the systems and methods of the present disclosure provide for the determination of fractional flow reserve in myocardial and/or brain tissue by measurement of plaque morphology. Systems and methods of the present disclosure may use sophisticated methods to characterize the vasodilatory capacity of vessels via objectively validated determination of tissue type and character which impact its distensibility. In particular, plaque morphology may be used as input to analysis of dynamic behavior of the vasculature from a flow reserve point of view (training the models with flow reserve truth data). Thus, it is possible to determine the dynamic behavior of the system rather than (only) a static description. Stenosis itself is well known as being of low predictive power in that it only provides a static description; addition of accurate plaque morphology is necessary, for the highest accuracy imaging-based assessment of dynamic function. The present disclosure provides systems and methods which determine accurate plaque morphology and then processes such to determine the dynamic function.

In example embodiments deep learning is utilized to retain the spatial context of tissue characteristics and vessel anatomy (collectively referred to as plaque morphology) at an optimal level of granularity, avoiding excessive non-material variability in the training sets while retaining that which is needed to exceed other more simplistic use of machine learning. Alternative methods by others use only measurements of vessel structure rather than a more complete processing of tissue characteristics. Such methods may capture lesion length, stenosis, and possibly entrance and exit angles, but they neglect the determinants of vasodilative capacity. High level assumptions about the flexibility of the artery tree as a whole must be made to use these models, but plaques and other tissue properties cause the distensibility of the coronary tree to be distensible in a heterogeneous way. Different portions of the tree are more or less distensible. Because distensibility is a key element in determining FFR, the methods are insufficient. Other methods which attempt to do tissue characteristics do so without objective validation as to their accuracy and/or without the data enrichment methods needed to retain spatial context optimally for medical image deep learning (e.g., transformation such as unwrapping and the validated false color tissue type overlays) necessary to provide the effectiveness of deep learning methods. Some methods try to increase training set size by use of synthetic data, but this is ultimately limited to the limited data on which the synthetic generation as based and amounts more to a data augmentation scheme rather than a real expansion of the input training set. Additionally, the systems and methods of the present disclosure are able to create continuous assessments across vessel lengths.

The systems and methods of the present disclosure effectively leverage objective tissue characterization validated by histology across multiple arterial beds. Of relevance to the example application in atherosclerosis, plaque composition is similar in coronary and carotid arteries, irrespective of its age, and this will largely determine relative stability, suggesting similar presentation at CCTA as at CTA. Minor differences in the extent of the various plaque features may include a thicker cap and a higher prevalence of intraplaque hemorrhage and calcified nodules in the carotid arteries, however, without difference in the nature of plaque components. In addition, the carotid and coronary arteries have many similarities in the physiology of vascular tone regulation that has effect on plaque evolution. Myocardial blood perfusion is regulated by the vasodilation of epicardial coronary arteries in response to a variety of stimuli such as NO, causing dynamic changes in coronary arterial tone that can lead to multifold changes in blood flow. In a similar fashion, carotid arteries are more than simple conduits supporting the brain circulation; they demonstrate vasoreactive properties in response to stimuli, including shear stress changes. Endothelial shear stress contributes to endothelial health and a favorable vascular wall transcriptomic profile. Clinical studies have demonstrated that areas of low endothelial shear stress are associated with atherosclerosis development and high-risk plaque features. Similarly, in the carotid arteries lower wall shear stress is associated with plaque development and localization. (Endothelial shear stress by itself is a useful measurement but not to replace plaque morphology.) It is important to acknowledge that technical challenges are different across beds (e.g. use of gating, vessel size, amount and nature of motion)—but these effects are mitigated by scan protocol, which result in approximate in-plane voxel sizes in the 0.5-0.75 mm range, and the through-plane resolution of coronary (the smaller vessels) is actually better than, rather than inferior to, that of carotids (with the voxels being isotropic in coronary and not so in the neck and peripheral extremities).

The present disclosure achieves an effective resolution with routinely acquired CTA in the same ballpark as IVUS VH, based on solid mathematics principles that respect the Nyquist-Shannon sampling theorem. IVUS imaging has excellent spatial resolution for gross structure (i.e., lumen) but generally lacks the ability to characterize plaque components with high accuracy. Literature estimates of IVUS resolution to be 70-200 µm axially and 200-400 µm laterally using typical transducers in the 20-40 MHz range. IVUS VH is a method of spectral backscatter analysis that enables plaque composition analysis (and thus measurements). For IVUS VH methodology using large (e.g., 480 µm) moving windows in the axial direction, the relatively large size of this moving window (and thus, the accuracy of the composition analysis) is fundamentally limited by the bandwidth requirements of the spectral analysis. Where IVUS VH images are displayed at smaller moving windows, e.g., 250 µm, this limits the accuracy of this analysis since each IVUS pixel is classified into a discrete category. 64-slice multi-detector CCTA scans have been described to be in the range of 300-400 µm resolution. While this already puts CCTA resolution very close to that of IVUS VH, there are additional factors specific to the present invention analysis to consider. Thus, rather than discretely classifying CCTA pixels, the systems and methods of the present disclosure perform an iterative deblurring or restoring modeling step with sub-voxel precision, e.g., using a tessellated surface of triangles to represent the true surface of lipid core. Lipid core areas are in the range of 6.5-14.3 mm2 in 393 patients (corresponding radius of curvature of 1.4-2.1 mm). Using the formula for chord length where the chord spans a single voxel diagonally, this represents an upper limit on the error of the tessellated surface representation of lipid cores at 44 µm. There are additional factors associated with the deblurring or restoring analysis that may cause errors on the order of half a pixel for a total range of accuracy of 194-244 µm, generally equivalent to the accuracy of IVUS VH for measuring cap thickness.

The present disclosure is also innovative in dealing with fundamental limitations of the application of artificial intelligence and deep learning to the analysis of atherosclerosis imaging data. Conventional competitive approaches that lack a validated and objective basis such as are fundamentally limited in multiple ways. First, arbitrary thresholds are used, resulting in an inability to assess accuracy except in a weak form of correlation to other markers that themselves lack objective validation. Second, this lack of objectivity increases the demands for large volumes of data on which to circumstantially base correlations. This imposes infeasible demands for manual annotation of the radiological images which are themselves the subject of analysis (that is, as opposed to being validated from an independent modality). Thirdly, due to the interpretability of the resulting model, these models must be presented to regulatory agencies such as FDA as a "black box" which lacks a scientifically rigorous elucidation on mechanisms of action that can be tied to traditional biological hypothesis testing. Specifically, whereas CNNs have proven to be excellent at performing many different computer vision tasks, they have substantial drawbacks when applied to radiology data sets: 1) the need for vast training and validation datasets, and 2) intermediate CNN computations are generally not representative of any measurable property, which makes regulatory approval difficult. To address these challenges, we utilize a pipeline approach consisting of stages with outputs which are individually objectively capable of validation at the biological level to feed the CNN. The present invention overcomes these drawbacks by using a pipeline consisting of one or more stages which are biologically measurable (that is, capable of being objectively validated), followed by smaller scope convolutional neural network processing on these validated biological properties to output the desired output conditions not based on subjective or qualitative "imaging features" but rather. These architectural capabilities mitigate drawbacks by increasing the efficiency of available training data and make the intermediate steps capable of being objectively validated. The systems and methods of the present disclosure simultaneously alleviate drawbacks of using CNNs for medical imaging by 1) reducing the complexity of the vision task to within levels that are acceptable when training a CNN with a moderately sized dataset, and 2) producing intermediate outputs which are both objectively validated and easily interpretable by users or regulating bodies. Intermediate CNN computations are not generally representative of any measurable property, spatial context is often difficult to obtain in ML approaches using feature extraction, and use of raw data sets that do contain spatial context often lack objective ground truth labels for the extracted features, whether they are processed using traditional machine learning or deep learning approaches. Likewise, raw data sets include much variation that is "noise" with respect to the classification problem at hand, which is overcome in computer vision applications outside of medical by having very large training sets of a scale not generally available in medical applications, especially data sets annotated with ground truth.

The quantitative ability of the systems and methods of the present disclosure makes such ideal for analysis of more advanced imaging protocols (protocols such as early/delayed phase contrast, dual-energy, and multi-spectral techniques are being investigated for tissue characterization).

While the systems and methods of the present disclosure have been particularly shown and described with reference to example embodiments thereof, it will be understood by those skilled in the art that various changes in form and details may be made therein without departing from the scope of the present disclosure.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments of the present disclosure.

FIG. 6 illustrates a technique for computing putative analyte blobs, according to the present disclosure.

FIG. 7 depicts normalized vessel wall coordinates for an exemplary vessel wall composition model, according to the present disclosure.

FIG. 10 depicts representing an exemplary analyte blob with a distribution of normalized vessel wall coordinates, according to the present disclosure.

FIG. 11 depicts an exemplary distribution of blog descriptors, according to the present disclosure.

FIG. 28 represents validation results for algorithms trained and validated with different variations of data enriched imaging, according to the present disclosure.

FIG. 29 provides an example application of phenotyping lung lesions, according to the present disclosure.

FIG. 30 provides an example of biological properties (including e.g., tissue characteristics, morphology, etc.) for phenotyping lung lesions, according to the present disclosure. Note that in example embodiments, false colors may be represented as continuous values rather than discrete values with respect to one or more of these biological properties.

DETAILED DESCRIPTION

Figure 1:
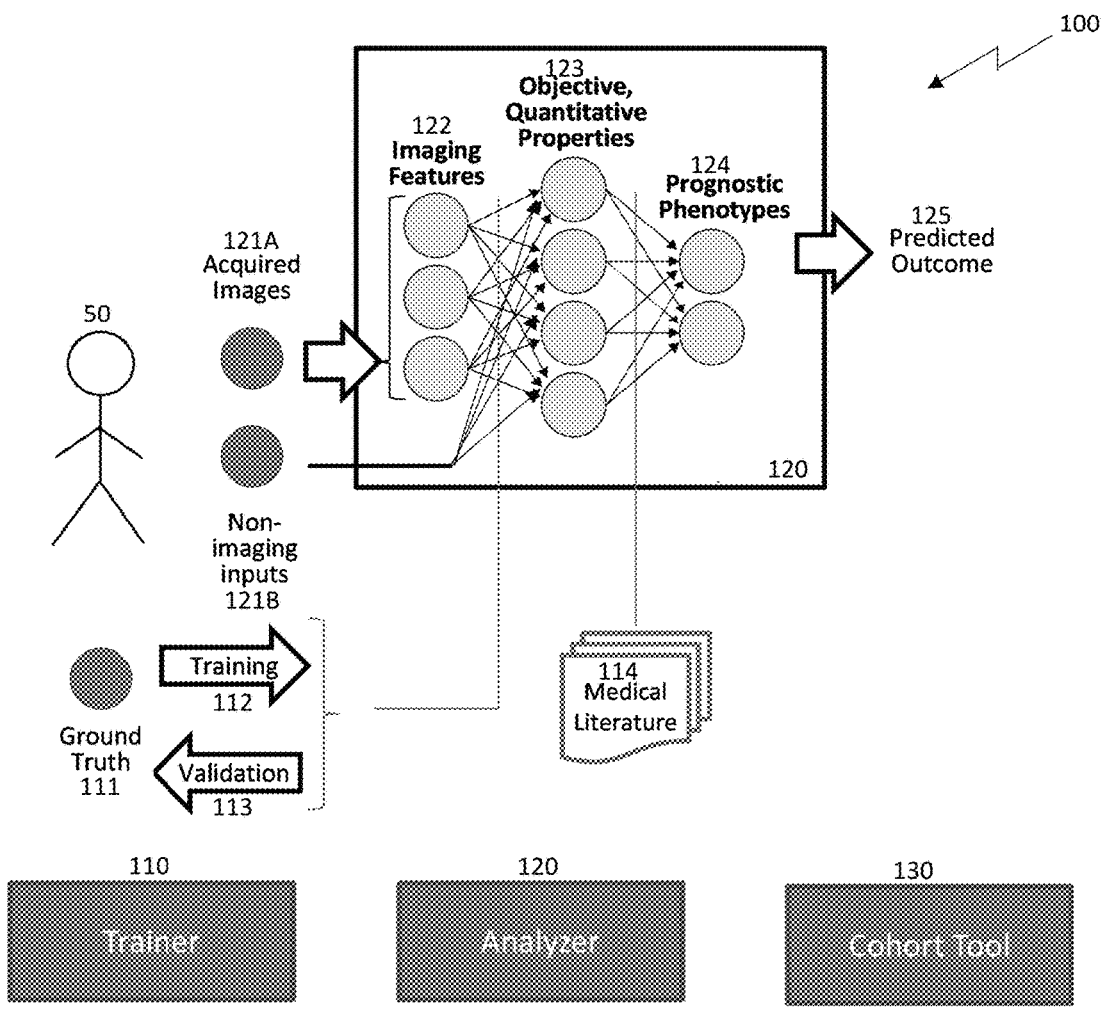
FIG. 1 depicts a schematic of an exemplary system for determining and characterizing a medical condition by implementing a hierarchical analytics framework, according to the present disclosure.

Systems and methods for analyzing pathologies utilizing quantitative imaging are presented herein. Advantageously, the systems and methods of the present disclosure utilize a hierarchical analytics framework that identifies and quantify biological properties/analytes from imaging data and then identifies and characterizes one or more pathologies based on the quantified biological properties/analytes. This hierarchical approach of using imaging to examine underlying biology as an intermediary to assessing pathology provides many analytic and processing advantages over systems and methods that are configured to directly determine and characterize pathology from raw imaging data without the validation steps and/or without advantageous processing described herein.

One advantage, for example, is the ability to utilize training sets from non-radiological sources, e.g., from tissue sample sources such as histological information, in conjunction with or independent of training sets for radiological sources, to correlate radiological imaging features to biological properties/analytes to pathologies. For example, in some embodiments, histology information may be used in training algorithms for identifying and characterizing one or more pathologies based on quantified biological properties/analytes. More specifically, biological properties/analytes which are identifiable/quantifiable in non-radiological data (such as in an invasively obtained histology data set or obtainable via gene expression profiling) may also be identified and quantified in radiological data (which is advantageously non-invasive). These biological properties/analytes may then be correlated to clinical findings on pathology using information the from non-radiological sources, for example, utilizing histological information, gene expression profiling, or other clinically rich data sets. This set of clinically correlated data may then serve as a training set or part of a training set for determining/tuning (e.g., utilizing machine learning) algorithms correlating biological properties/analytes to pathologies with a known relationship to clinical outcome. These algorithms correlating biological properties/analytes to pathologies derived utilizing non-radiological source training sets may then be applied in evaluating biological properties/analytes derived from radiological data. Thus, the systems and methods of the present disclosure may advantageously enable utilizing radiological imaging (which may advantageously be cost-effective and non-invasive) to provide surrogate measures for predicting clinical outcome or guiding treatment.

Notably, in some instances training data for non-radiological sources (such as histology information) may be more accurate/reliable than training data for radiological sources. Moreover, in some embodiments, training data from non-radiological sources may be used to augment training data from radiological sources. Thus, since better data in is likely to yield better data out, the hierarchical analytics framework disclosed advantageously improves the trainability and resulting reliability of the algorithms disclosed herein. As noted above, one key advantage is that, once trained the systems and methods of the present disclosure may enable deriving comparable clinical information to existing histological and other non-radiological diagnostic-type testing without the need not undergo invasive and/or costly procedures.

Alternatively, in some embodiments, training sets for non-radiological sources (such as non-radiological imaging sources, e.g., histological sources, and/or non-imaging sources) may be utilized in conjunction with or independent of training sets for radiological sources, e.g., in correlating image features to biological properties/analytes. For example, in some embodiments one or more biological models may be extrapolated and fitted to correlate radiological and non-radiological data. For example, histology information may be correlated with radiological information based on an underlying biological model. This correlation may advantageously enable training recognition of biological properties/analytes in radiological data utilizing non-radiological, e.g., histological information.

In some embodiments, data drawn from complementary modalities may be used, e.g., in correlating image features to biological properties/analytes from blood panels, physical FFR, and/or other sources of data.

In example embodiments one or more biological models may be extrapolated and fitted utilizing imaging data drawn from one imaging modality either correlated with and/or fused with another imaging modality or non-imaging source such as bloodwork. These biological models may advantageously correlate across and between imaging and non-imaging data sets based on the biological models. Thus, these biological models may enable the hierarchical analytics framework to utilize data from one imaging modality with another imaging modality or with a non-imaging source in identifying/quantifying one or more biological properties/analytes or identifying/characterizing one or more medical conditions.

Another advantage to the hierarchical analytics framework disclosed herein, is the ability to incorporate data from multiple same or different type data sources into the process of identifying and characterizing pathology based on imaging data. For example, in some embodiments, one or more non-imaging data sources may be used in conjunction with one or more imaging data sources in identifying and quantifying a set of biological properties/analytes. Thus, in particular, the set of biological properties/analytes may include one or more biological properties/analytes identified and/or quantified based on one or more imaging data sources, one or more biological properties/analytes identified and/or quantified based on one or more non-imaging data sources, and/or one or more biological properties/ analytes identified and/or quantified based on a combination of imaging and non-imaging data sources (note that, for the purposes of the present disclosure the set of biological properties/analytes may generally include at least one or more biological properties/analytes identified and/or quantified based at least in part on an imaging data). The ability to augment information from an imaging data source with information from other imaging and/or non-imaging data sources in identifying and quantifying a set of biological properties/analytes adds to the robustness of the systems and methods presented herein and enables utilization of any and all relevant information in identifying and characterizing pathology.

Yet another advantage of the hierarchical analytics framework involves the ability to adjust/fine-tune data at each level, e.g., prior or subsequent to utilizing that data to assess the subsequent level (note that in some embodiments this may be an iterative process). For example, in some embodiments, information related to a set of identified and quantified biological properties/analytes may be adjusted in an a posteriori manner (e.g., after an initial identification and/or quantification thereof). Similarly, in some embodiments, information related to a set of identified and characterized pathologies may be adjusted in an a posteriori manner (e.g., after an initial identification and/or characterization thereof). These adjustments may be automatic or user based and may objective or subjective. The ability to adjust/fine-tune data at each level may advantageously improve data accountability and reliability.

In example embodiments, adjustments may be based on contextual information, which may be used to update one or more probabilities impacting a determination or quantification of a biological property/analyte. In example embodiments, contextual information for adjusting information related to a set of identified and quantified biological properties/analytes in an a posteriori manner may include patient demographics, correlations between biological properties/analytes or correlations between identified/characterized pathologies and biological properties/analytes. For example, in some instances the biological properties/analytes may be related in the sense that the identification/quantification of a first biological property/analyte may impact a probability relating the identification/quantification of a second biological property/analyte. In other instances, identification/characterization of a first pathology, e.g., based on an initial set of identified/quantified biological properties/analytes may impact a probability relating to the identification/quantification of a biological property/analyte in the initial set or even a biological property/analyte that wasn't in the first set. In further instances, pathologies may be related, e.g., wherein identification/characterization of a first pathology may impact a probability relating the identification/characterization of a first pathology. As noted above, information related to identification and quantification of biological properties/analytes and/or information related to the identification and characterization of pathologies may be updated in an iterative manner, e.g., until data convergence or thresholds/benchmarks are achieved or for a selected number of cycles.

A further advantage of the hierarchical analytics framework involves the ability to provide a user, e.g., a physician, with information relating both to a pathology as well as the underlying biology. This added context may facilitate clinical diagnosis/evaluation as well as assessing/determining next steps, e.g., therapeutic/treatment options or further diagnostics. For example, the systems and methods may be configured to determine which biological parameters/analytes relevant to the identification/quantification of one or more pathologies are most indeterminate/have the highest degree of uncertainty (e.g., by reason of lack of data or conflicting data). In such instances, specific further diagnostics may be recommended. The added context of providing a user with information relating both to a pathology as well as the underlying biology may further help the user evaluate/error check various the clinical conclusions and recommendations reached by the analytics.

A hierarchical analytics framework, as used herein, refers to an analytic framework wherein a one or more intermediary sets of data points are utilized as an intermediary processing layer or an intermediary transformation between initial set of data points and an end set of data points. This is similar to the concept of deep learning or hierarchical learning wherein algorithms are used to model higher level abstractions using multiple processing layers or otherwise utilizing multiple transformations such as multiple non-linear transformations. In general, the hierarchical analytics framework of the systems and methods of the present disclosure includes data points relating to biological properties/analytes as an intermediary processing layer or intermediary transformation between imaging data points and pathology data points, in example, embodiments, multiple processing layers or multiple transformation (e.g., as embodied by multiple levels of data points) may be included for determining each of imaging information, underlying biological information and pathology information. While example hierarchical analytic framework structures are introduced herein (e.g., with specific processing layers, transforms and datapoints), the systems and methods of the present disclosure are not limited to such implementations. Rather, any number of different types of analytic framework structures may be utilized without departing from the scope and spirit of the present disclosure.

In example embodiments, the hierarchical analytics frameworks of the subject application may be conceptualized as including a logical data layer as an intermediary between an empirical data layer (including imaging data) and a results layer (including pathology information). Whereas the empirical data layer represents directly sourced data the logical data layer advantageously adds a degree of logic and reasoning which distills this raw data into a set of useful analytes for the results layer in question. Thus, for example, empirical information from diagnostics such as raw imaging information may be advantageously distilled down to a logical information relating to a particular set of biological features which is relevant for assessing a selected pathology or group of pathologies (for example, pathologies related to an imaged region of the patient's body). In this way the biological features/analytes of the subject application can also be thought of as pathology symptoms/indicators.

The biological features/analytes of the subject application may at times be referred to herein a biomarkers. While the term "biological" or prefix "bio" is used in characterizing biological features or biomarkers this in only intended to signify that the features or markers have a degree of relevance with respect to the patient's body. For example, biological features may be anatomical, morphological, compositional, functional, chemical, biochemical, physiological, histological, genetic or any number of other types of features related to the patient's body. Example, biological features utilized by specific implementations of the systems and methods of the present disclosure (e.g., as relating to particular anatomical regions of a patient such as the vascular system, the respiratory system, organs such as the lungs, heart or kidneys, or other anatomical regions) are disclosed herein.

While example systems and methods of the present disclosure may be geared toward detecting, characterizing and treating pathologies/diseases, the application of the systems and methods of the present disclosure are not limited to pathologies/diseases but rather may more generally applicable with respect to any clinically relevant medical conditions of a patient including, e.g., syndromes, disorders, traumas, allergic reactions, etc.

In exemplary embodiments, the systems and methods of the present disclosure relate to Computer-Aided Phenotyping, e.g., by using knowledge about biology to analyze medical images to measure the differences between disease types that have been determined through research to indicate phenotypes which in turn predict outcomes. Thus, in some embodiments, characterizing pathologies may include determining phenotypes for the pathologies which may in turn determine a predictive outcome.

With initial reference to FIG. 1, a schematic of an exemplary system 100 is depicted. There are three basic functionalities which may be provided by the system 100 as represented by the trainer module 110, the analyzer module 120 and the cohort tool module 130. As depicted, the analyzer module 120 advantageously implements a hierarchical analytics framework which first identifies and quantifies biological properties/analytes 130 utilizing a combination of (i) imaging features 122 from one or more acquired images 121A of a patient 50 and (ii) non-imaging input data 121B for a patient 50 and then identifies and characterizes one or more pathologies (e.g., prognostic phenotypes) 124 based on the quantified biological properties/analytes 123. Advantageously, the analyzer module 120 may operate independent of ground truth or validation references by implementing one or more pre-trained, e.g., machine learned algorithms for drawing its inferences.

In example embodiments, the analyzer may include algorithms for calculating imaging features 122 from the acquired images 121A of the patient 50. Advantageously, some of the image features 122 may be computed on a per-voxel basis while others may be computed on a region-of-interest basis. Example non-imaging inputs 121B which may be utilized along with acquired images 121A may include data from laboratory systems, patient-reported symptoms, or patient history.

As noted above, the image features 122 and non-imaging inputs may be utilized by the analyzer module 120 to calculate the biological properties/analytes 123. Notably, the biological properties/analytes are typically quantitative, objective properties (e.g., objectively verifiable rather than being stated as impression or appearances) that may represent e.g., a presence and degree of a marker (such as a chemical substance) or other measurements such as structure, size, or anatomic characteristics of region of interest. In example embodiments, the quantified biological properties/analytes 123 may be displayed or exported for direct consumption by the user, e.g., by a clinician, in addition to or independent of further processing by the analyzer module.

In example embodiments, one or more of the quantified biological properties/analytes 123 may be used as inputs for determining phenotype. Phenotypes are typically defined in a disease-specific manner independent of imaging, often being drawn from ex vivo pathophysiological samples for which there is documented relationship to outcome expected. In example embodiments, the analyzer module 120 may also provide predicted outcomes 125 for determined phenotypes.

It should be appreciated that example implementations of the analyzer module 120 are further described herein with respect to specific embodiments which follow the general description of the system 100. In particular, specific imaging features, biological properties/analytes and pathologies/phenotypes are described with respect to specific medical applications such as with respect to the vascular system or with respect to the respiratory system.

With reference still to FIG. 1, the cohort tool module 130 enables defining a cohort of patients for group analyses thereof, e.g., based on a selected set of criteria related to the cohort study in question. An example cohort analysis may be for a group of patients enrolled in a clinical trial, e.g., with the patient's further being grouped based on one or more arms of the trial for example a treatment vs. control arm. Another type of cohort analysis may be for a set of subjects for which ground truth or references exist, and this type of cohort may be further decomposed into a training set or "development" set and a test or "holdout" set. Development sets may be supported so as to train 112 the algorithms and models within analyzer module 120, and holdout sets may be supported so as to evaluate/validate 113 the performance of the algorithms or models within analyzer module 120.

With continued reference to FIG. 1, the trainer module 110 may be utilized to train 112 the algorithms and models within analyzer module 120. In particular, the trainer module 110, may rely on ground truth 111 and/or reference annotations 114 so as to derive weights or models, e.g., according to established machine learning paradigms or by informing algorithm developers. In example embodiments, classification and regression models are employed which may be highly adaptable, e.g., capable of uncovering complex relationships among the predictors and the response. However, their ability to adapt to the underlying structure within the existing data can enable the models to find patterns that are not reproducible for another sample of subjects. Adapting to irreproducible structures within the existing data is commonly known as model over-fitting. To avoid building an over-fit model, a systematic approach may be applied that prevents a model from finding spurious structure and enable the end-user to have confidence that the final model will predict new samples with a similar degree of accuracy on the set of data for which the model was evaluated.

Successive training sets may be utilized to determine optimal tuning parameter(s), and a test set may be utilized to estimate an algorithm's or model's predictive performance. Training sets may be used for training each of the classifiers via randomized cross-validation. Datasets may be repeatedly split into training and testing sets and may be used to determine classification performance and model parameters. The splitting of the datasets into training and test sets occurs using a stratified or maximum dissimilarity approaches. In example embodiments a re-sampling approach (e.g. bootstrapping) may be utilized within the training set in order to obtain confidence intervals for (i) the optimal parameter estimate values, and (ii) the predictive performance of the models.

Figure 2:
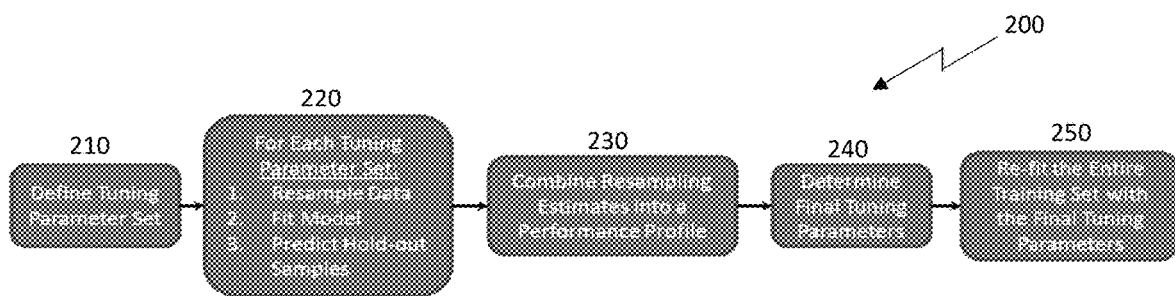
FIG. 2 outlines a re-sampling based model building approach, according to the present disclosure which may be implemented by the systems and methods described herein.

FIG. 2 outlines a re-sampling based model building approach 200 which may be utilized by the systems and methods of the present disclosure. First, at step 210, a tuning parameter set may be defined. Next, at step 220, for each tuning parameter set data is resampled the model is fitted and hold-out samples are predicted. At step 230, Resampling estimates are combined into a performance profile. Next, at step 240, final tuning parameters may be determined. Finally, at step 250, the entire training set is re-fitted with the final tuning parameters. After each model has been tuned from the training set, each may be evaluated for predictive performance on the test set. Test set evaluation occur once for each model to ensure that the model building process does not over-fit the test set. For each model that is constructed, the optimal tuning parameter estimates, the re-sampled training set performance, as well as the test set performance may be reported. The values of the model parameters over randomized splits are then be compared to evaluate model stability and robustness to training data.

According to the systems and methods of the present disclosure, a number of models may be tuned for each of the biological properties/analytes (e.g., tissue types) represented in ground truth maps. Model responses may include, for example, covariance-based techniques, non-covariance based techniques, and tree based models. Depending on their construction, endpoints may have continuous and categorical responses; some of the techniques in the above categories are used for both categorical and continuous responses, while others are specific to either categorical or continuous responses. Optimal tuning parameter estimates, the re-sampled training set performance, as well as the test set performance may be reported for each model.

TABLE 1

| | |
|---|---|
| Delineate Field | Register multiple data streams across a field |
| | Segment organs, vessels, lesions, and other application-specific objects |
| | Reformat anatomy for specific analyses |
| Delineate Target | Register multiple data streams at a locale |
| | Fine-grained segmentation |
| | Measure size and/or other relevant anatomic structure |
| | Extract whole-target features |
| Delineate Sub-target regions | Split target into sub-targets according to application |
| | Sub-target specific calculations |
| Delineate Components | (Re–) Segment Component |
| | Calculate Readings |
| | Visualize Probability Map |
| Determine Disease Severity | Determine Phenotype |
| | Predict Outcome |
| Compare Multiple Timepoints | (Optional) Compare Multiple Timepoints |
| Assess multi-focal disease | Aggregate across target lesions over a wide scan field. |
| Generate Patient Report | Generate Patient Report |

Table 1, above, provides a summary of some of the example functionalities of the analyzer module 120 of system 100. Namely, the analyzer module 120 may be configured to delineate fields, for example, to register multiple data streams across a field; to segment organs, vessels, lesions and other application-specific objects; and/or to reformat/reconfigure anatomy for specific analyses. The analyzer module 120 may further be configured for delineating a target, for example, a lesion, in a delineated field. Delineating a target may, for example, include registering multiple data streams at a locale; conducting fine-grained segmentation; measuring size and/or other characteristics of relevant anatomic structures; and/or extracting whole-target features (e.g., biological properties/analytes characteristic of the entire target region). In some embodiments, one or more sub-target regions may also be delineated, for example, a target region may be split into sub-targets according to a particular application with sub-target specific calculations (e.g., biological properties/analytes characteristic of a sub-target region). The analyzer module 120 may also delineate components or relevant features (such as composition), for example, in a particular field, target or sub-target region. This may include segmenting or re-segmenting the components/features, calculating values for the segmented components/features (e.g., biological properties/analytes characteristic of the component/feature) and assigning a probability map to the readings. Next pathologies may be determined, based on the biological quantified properties/analytes, and characterized, e.g., by determining phenotype and/or predictive outcomes for the pathologies. In some embodiments, the analyzer module 120 may be configured to compare data across multiple timepoints, e.g., one or more of the biological components/analytes may involve a time-based quantification. In further embodiments, a wide scan field may be utilized to assess multi-focal pathologies, e.g., based on aggregate quantifications of biological properties/analytes across a plurality of targets in the delineated field. Finally, based on the forgoing analytics, the analyzer module 120 may be configured to generate a patient report.

Figure 3:
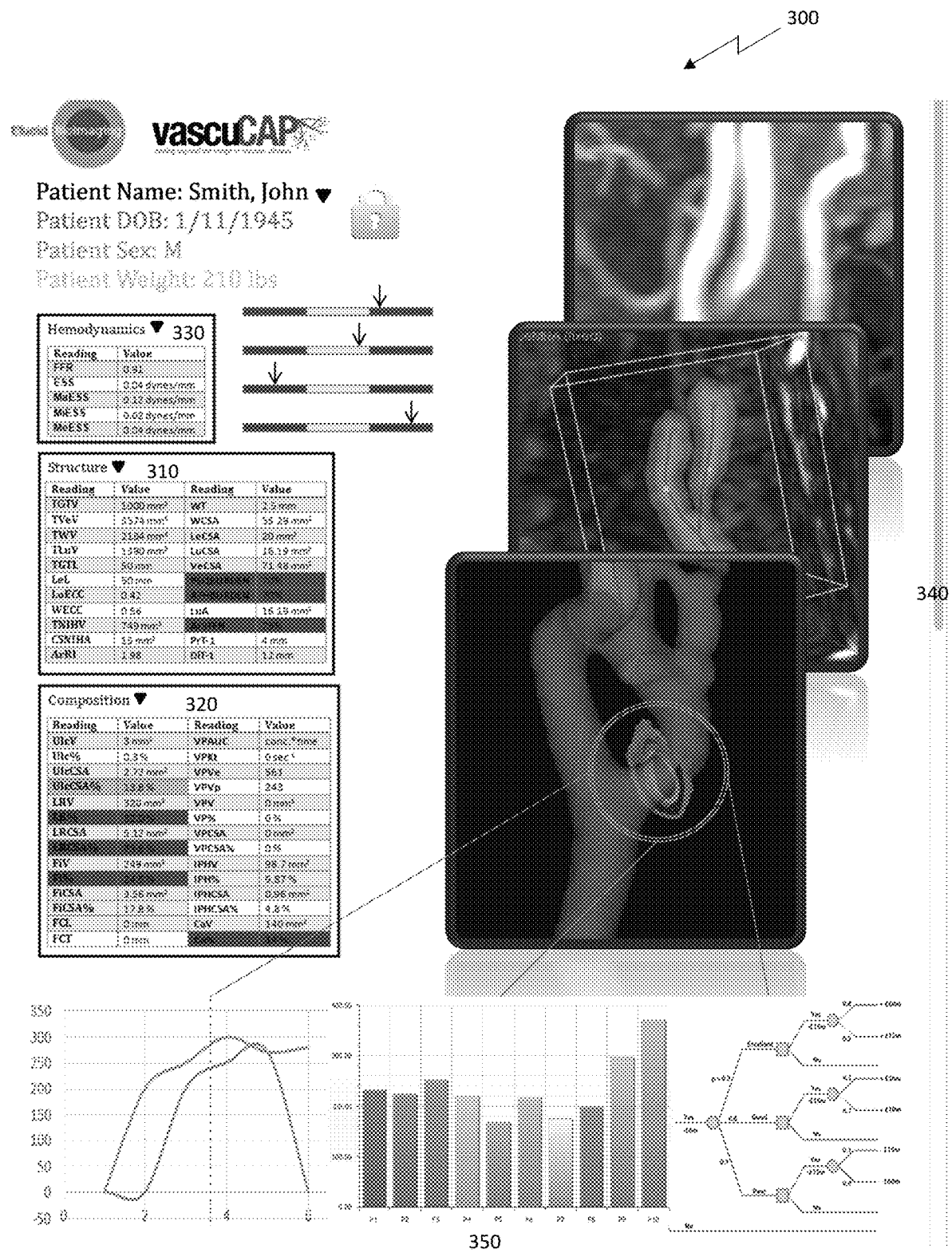
FIG. 3 depicts a sample patient report, according to the present disclosure which may be outputted by the systems and methods described herein.

A sample patient report 300 is depicted in FIG. 3. As shown, the sample patient report 300 may include quantifications of biological parameters/analytes such as relating to structure 310 and composition 320 as well as data from non-imaging sources such as hemodynamics 330. The sample patient report may further include visualizations 340, e.g., 2D and/or 3D visualizations of imaging data as well as combined visualizations of non-imaging data such as hemodynamic data overlaid onto imaging data. Various analytics 350 may be displayed for assessing the biological parameters/analytes including, e.g., a visualization of one or more model(s) (e.g., a decision tree model) for determining/characterizing pathology. Patient background and identifying information may further be included. Thus, the analyzer module 120 of system 100 may advantageously provide a user, e.g., a clinician with comprehensive feedback for assessing the patient.

Advantageously the systems and methods of the present disclosure may be adapted for specific applications. Example vascular and lung applications are described in greater detail in the sections which follow (although it will be appreciated that the specific application described have general implications and interoperability with respect to numerous other applications). Table 2 provides an overview of vascular and lung related applications utilizing a hierarchical analytics framework as described herein.

TABLE 2

| | Vascular Application | Lung Application |
|---|---|---|
| Modality | CT or MR | CT |
| Indication | Asymptomatic CAS | Lung Cancer Screening |
| | Cryptogenic stroke | Drug therapy response assessment |
| | NSTEMI, CABG Patency Evaluation | Companion-diagnostic for expensive or targeted drugs |
| | Companion-diagnostic for expensive or targeted drugs | |
| Diseases | Peripheral and coronary artery vasculopathy | Lung cancer first, then other pulmonary disease |
| Biological Properties | Structure | Size, Shape/Margin |
| | Composition | Solidity, Heterogeneity |
| | Hemodynamics | Invasive Potential |
| | Gene Expression Correlates | Gene Expression Correlates |
| Extension | Ultrasound and/or multi-energy CT | PET and/or multi-energy CT |

The following sections provide specific examples of quantitative biological properties/analytes that may be utilized by the systems and methods of the present disclosure with respect to vascular applications:

Anatomic Structure: Vessel structural measurements, specifically those that lead to the determination of % stenosis, have long been and remain the single most used measurements in patient care. These were initially limited to inner lumen measurements, rather than wall measurements involving both the inner and outer surfaces of the vessel wall. However, all of the major non-invasive modalities, unlike X-ray angiography, can resolve the vessel wall and with this come expanded measurements that may be achieved. The category is broad and the measurements are of objects of varying sizes, so generalizations should be made with care. A primary consideration is the limit of spatial sampling or resolution. The minimally detectable changes in wall thickness may, however, be lower than the spatial sampling by taking advantage of subtle variations in intensity levels due to partial volume effect. Additionally, stated resolutions generally refer to grid size and field of view of post-acquisition reconstructions rather than the actual resolving power of the imaging protocol, which determines the minimum feature size that can be resolved. Likewise, in-plane vs. through-plane resolutions may or may not be the same and not only the size of a given feature but as well its proportions and shape will drive the measurement accuracy. Last but not least, in some cases categorical conclusions are drawn from applying thresholds to the measurements, which may then be interpreted according to signal detection theory with the ability to optimize the trade-off between sensitivity and specificity, terms that don't otherwise refer to measurements in the normal sense.

Tissue Characteristics: The quantitative assessment of the individual constituent components of the atherosclerotic plaques, including for example lipid rich necrotic core (LRNC), fibrosis, intraplaque hemorrhage (IPH), permeability, and calcification, can provide crucial information concerning the relative structural integrity of the plaque that could aid the physician's decisions on course of medical or surgical therapy. From the imaging technology point of view, the ability to do this lies less with spatial resolution as with contrast resolution and tissue discrimination made possible by differing tissues responding to incident energy differently so as to produce a differing receive signal. Each imaging modality does this to some extent; terms in ultrasound such as "echolucency", the CT number in Hounsfield Units, and differentiated MR intensities as a function of various sequences such as (but not limited to) T1, T2 and T2*.

Dynamic tissue behavior (e.g., Permeability): In addition to morphological features of the vessel wall/plaque, there is increasing recognition that dynamic features are valuable quantitative indicators of vessel pathology. Dynamic sequences where the acquisition is taken at multiple closely-spaced times (known as phases) expand the repertoire beyond spatially-resolved values t include temporally-resolved values which may be used for compartment modeling or other techniques to determine the tissues' dynamic response to stimulus (such as but not limited to wash-in and wash-out of contrast agent). Through the use of dynamic contrast enhanced imaging with ultrasound or MR in the carotid arteries or delayed contrast enhancement in the coronary arteries, sensitive assessments of the relative permeability (e.g., Ktrans and Vp parameters from kinetic analysis) of the microvascular networks of neoangiogenesis within the plaques of interest can be determined. In addition, these dynamic series can also aid in the differentiation between increased vascular permeability versus intraplaque hemorrhage.

Hemodynamics: The basic hemodynamic parameters of the circulation have a direct effect on the vasculopathy. Blood pressures, blood flow velocity, and vessel wall shear stress may be measured by techniques ranging from very simple oscillometry to sophisticated imaging analysis. Using common principles of fluid dynamics, calculations of vessel wall shear stress can be ascertained for different regions of the wall. In similar fashion MRI, with or without the combination of US, has been used to calculate the wall shear stress (WSS) and correlate the results with structural changes in the vessel of interest. In addition, the effects of antihypertensive drugs on hemodynamics have been followed for short and long-term studies.

Thus, in example embodiments, key aspects of applying the systems and methods of the present disclosure in a vascular setting may include evaluating plaque structure and plaque composition. Evaluating plaque structure may advantageously include, e.g., lumen measurements (which improves stenosis measurement by providing area rather than only diameter measures) as well as wall measurements (e.g., wall thickness and vascular remodeling). Evaluating plaque composition may advantageously involve quantification of tissue characteristics (e.g., lipid core, fibrosis, calcification, permeability, etc.) rather than just "soft" or "hard" designations as typically found in the prior art. Tables 3 and 4, below, describe example structural calculations and tissue characteristic calculations, respectively which may be utilized by the vascular applications of the systems and methods of the present disclosure.

TABLE 3

Structural calculations of vessel anatomy supported by vascular applications of the systems and methods disclosed herein.

| Measurand | Description | Type and Units |
| --- | --- | --- |
| Remodeling Ratio | Calculated as the ratio of vessel area with plaque to reference vessel wall area without plaque | Expressed with value less than 1 for inward remodeling and greater than 1 for outward remodeling |
| % Stenosis | Calculated as the (1 − ratio of minimum lumen with plaque to reference lumen without plaque) × 100 both by area and by diameter | Expressed as percentage >0% |
| % Dilation | Calculated as the (ratio of maximum lumen with plaque to reference lumen without plaque − 1) × 100 both by area and diameter | Expressed as percentage >0% |
| Wall Thickness | Calculated by measuring the largest thickness of wall | Expressed in units of mm |

TABLE 4

Calculations of tissue characteristics supported by vascular applications of the systems and methods disclosed herein

| Measurand | Description | Type and Units |
|---|---|---|
| Lipid Core | The pathologic retention of lipids, particularly lipoproteins, by intimal/medial cells leading to progressive cell loss, cell death, degeneration, and necrosis. It is a mixture of lipid, cellular debris, blood and water in various concentrations. | Burden in $mm^2$ by cross section and $mm^3$ by target and vessel |
| Fibrosis | The pathologic and sometimes physiologic defensive production of fibrous tissue by fibroblasts and activated smooth muscle cells. | Burden in $mm^2$ by cross section and $mm^3$ by target and vessel |
| Calcification | The physiologic defensive biological process of attempting to stabilize plaque, which has a mechanism akin to bone formation. | Agatston score and burden in $mm^2$ by cross section and $mm^3$ by target and vessel |
| Hemorrhage | A pathologic component that may contribute to the vulnerability of a plaque. Its role is not fully understood, but it is believed to be a driving force in plaque progression through lipid accumulation from red blood cells. | Burden in $mm^2$ by cross section and $mm^3$ by target and vessel |
| Permeability | Described as endothelial and intimal permeability due to neovascularization, necrosis, collagen breakdown, and inflammation | Burden in $mm^2$ by cross section and $mm^3$ by target and vessel |
| Thrombosis | Local coagulation or clotting of the blood in a part of the circulatory system. | Degree |
| Ulceration | Disintegration and necrosis of epithelial tissue | Burden in $mm^2$ by cross section and $mm^3$ by target and vessel |

Example systems relating to evaluating the vascular system may advantageously include/employ algorithms for evaluating vascular structure. Thus, the systems may employ, e.g., a target/vessel segment/cross-section model for segmenting the underlying structure of an imaged vessel. Advantageously a fast-marching competition filter may be applied to separate vessel segments. The systems may further be configured to handle vessel bifurcations. Image registrations may be applied utilizing Mattes mutual information (MR) or mean square error (CT) metric, rigid versor transform, LBFGSB optimizer, or the like. As noted herein, vessel segmentation may advantageously include lumen segmentation. An initial lumen segmentation may utilize a confidence connected filter (e.g., carotid, vertebral, femoral, etc.) to distinguish the lumen. Lumen segmentation may utilize MR imaging (such as a combination of normalized, e.g., inverted for dark contrast, images) or CT imaging (such as use of registered pre-contrast, post-contrast CT and 2D Gaussian distributions) to define a vessel-ness function. Various connected components may be analyzed and thresholding may be applied. Vessel segmentation may further entail outer wall segmentation (e.g., utilizing a minimum curvature (k2) flow to account for lumen irregularities). In some embodiments, an edge potential map is calculated as outward-downward gradients in both contrast and non-contrast. In example embodiments, outer wall segmentation may utilize cumulative distribution functions (incorporating prior distributions of wall thickness, e.g., from 1-2 adjoining levels) in a speed function to allow for median thickness in the absence of any other edge information. In example embodiments, ferret diameters may be employed for vessel characterization. In further embodiments, wall thickness may be calculated as the sum of the distance to lumen plus the distance to the outer wall. In further embodiments, lumen and/or wall segmentations may be done using semantic segmentation using, for example, CNNs.

Example systems relating to evaluating the vascular system may further advantageously analyze vascular composition. For example, in some embodiments, composition may be determined based on image intensity and other image features. In some embodiments, the lumen shape may be utilized, e.g., as relating to determining thrombosis. Advantageously, an analyte blob model may be employed for better analyzing composition of particular sub-regions of the vessel. We define an analyte blob to be a spatially contiguous region, in 2D, 3D, or 4D images, of one class of biological analyte. The blob model may utilize an anatomically aligned coordinate system using isocontours, e.g., in normalized radial distance from the lumen surface to the adventitial surface of the vessel wall. The model may advantageously identify one or more blobs and analyze each blobs location e.g., with respect to the overall vessel structure as well as relative to other blobs. In example embodiments, a hybrid Bayesian/Markovian network may be utilized to model a relative location of a blob. The model may advantageously account for the observed image intensity at a pixel or voxel being influenced by a local neighborhood of hidden analyte category nodes thereby accounting for partial volume and scanner point spread function (PSF). The model may further allow for dynamically delineating analyte blob boundaries from analyte probability maps during inference by the analyzer module. This is a key distinction from typical machine vision approaches, such as with superpixel approaches, that pre-compute small regions to be analyzed but are unable to dynamically adjust these regions. An iterative inference procedure may be applied that utilizes uses the current estimate of both analyte probability and blob boundaries. In some embodiments parametric modeling assumptions or kernel density estimation methods may be used to enable probability density estimates between the sparse data used to train the model.

Introduced herein is a novel model for classification of composition of vascular plaque components that removes the requirements for histology-to-radiology registration. This model still utilizes expert-annotated histology as a reference standard but the training of the model does not require registration to radiological imaging. The multi-scale model computes the statistics of each contiguous region of a given analyte type, which may be referred to as a 'blob'. Within a cross-section through the vessel, the wall is defined by two boundaries, the inner boundary with the lumen and the outer boundary of the vessel wall, creating a donut shape in cross section. Within the donut shaped wall region, there are a discrete number of blobs (different than the default background class of normal wall tissue which is not considered to be a blob). The number of blobs is modeled as a discrete random variable. Then, each blob is assigned a label of analyte type and various shape descriptors are computed. Additionally, blobs are considered pairwise. Finally, within each blob, each pixel can produce a radiological imaging intensity value, which are modeled as independent and identically distributed (i.i.d.) samples that come from a continuously valued distribution specific to each analyte type. Note that in this last step, the parameters of the imaging intensity distributions are not part of the training process.

One key feature of this model is that it accounts for the spatial relationship of analyte blobs within the vessel and also to each other, recognizing that point-wise image features (whether from histology and/or radiology) is not the only source of information for experts to determine plaque composition. While the model allows for the ability to train without explicit histology-to-radiology registration, it could also be applied in situations where that registration is known. It is believed that statistically modeling the spatial layout of atherosclerotic plaque components for classifying unseen plaques is a novel concept.

Example techniques for estimating vessel wall composition from CT or MR images are further elaborated on in the following section. In particular, the methods may employ a multi-scale Bayesian analytic model. The basic Bayesian formulation is as follows:

$$P(A \mid I) = \frac{P(I \mid A) \cdot P(A)}{P(I)} \quad \text{posterior} = \frac{\text{likelihood} \cdot \text{prior}}{\text{evidence}}$$

In the context of the present disclosure, the hypothesis may be based on a multi-scale vessel wall analyte map, A, with observation combing from CT or MR image intensity information I.

Figure 4:
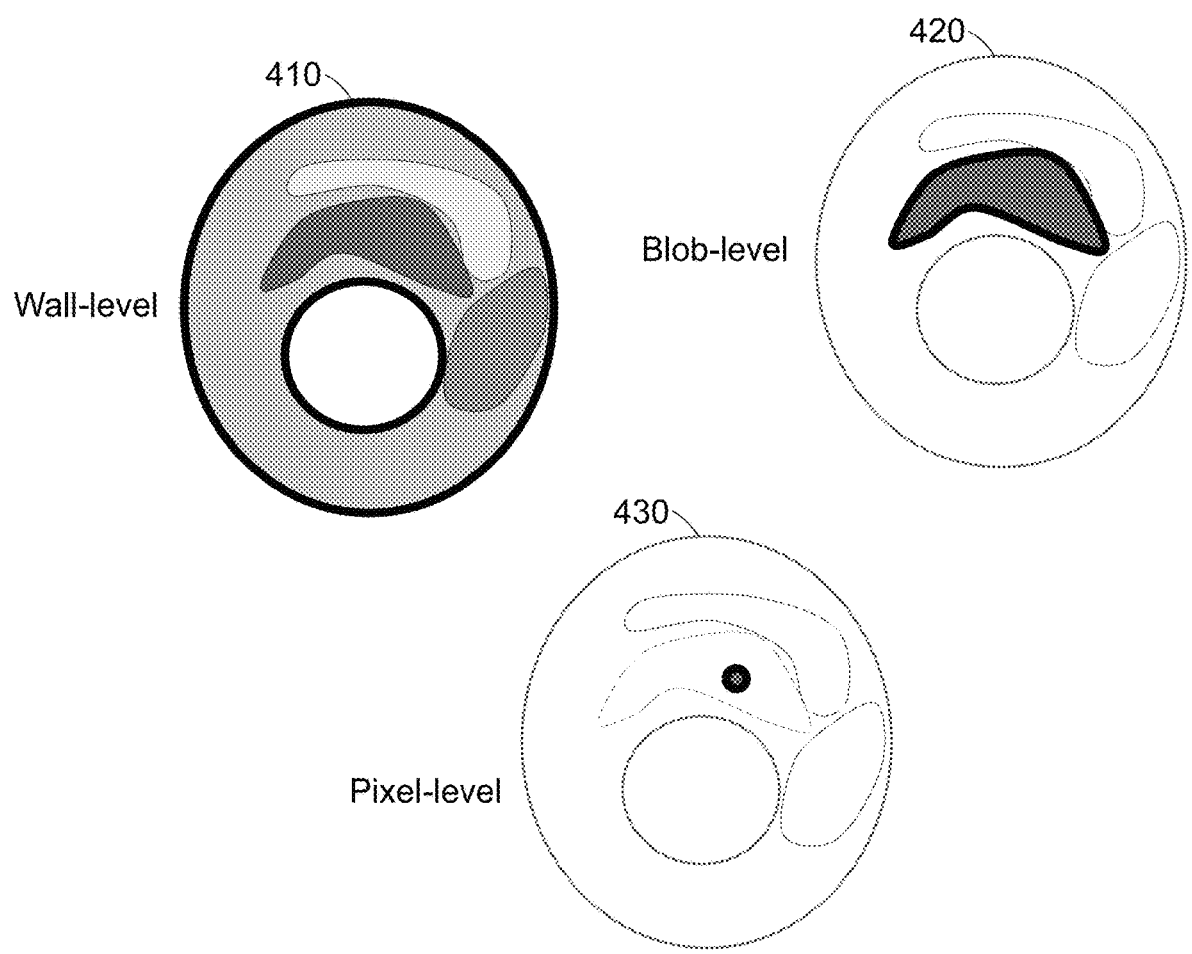
FIG. 4 depicts example segmentation levels for a multi-scale vessel wall analyte map, according to the present disclosure.

As depicted in FIG. 4, the multi-scale vessel wall analyte map may advantageously include wall-level segmentation 410 (e.g., a cross-sectional slice of the vessel), blob-level segmentation and pixel-level segmentation 430 (e.g., based on individual image pixels. E.g., A=(B,C) may be defined as a map of vessel wall class labels (similar to a graph with vertices B and edges C), wherein B is a set of blobs (cross-sectionally contiguous regions of non-background wall sharing a label) and C is a set of blob couples or pairs. $B_b$ may be defined as a generic single blob where $b \in [1 \ldots n_B]$ is an index of all blobs in A. $B_b^a$ is a blob with label a. For statistical purposes, the individual blob descriptor operator $D_B\{\}$ is in an low-dimensional space. $C_c$ may be defined as a blob pair where $c \in [1 \ldots n_B(n_B-1)/2]$ is an index of all blob pairs in A. $C_c^{f,g}$ is a blob pair with labels f and g. For statistical purposes, the blob pair descriptor operator $D_C\{\}$ is in a low-dimensional space. A(x)=a may be defined as the class label of pixel x where $a \in \{\text{'CALC', 'LRNC', 'FIBR', 'IPH', 'background'}\}$ (compositional characteristics). In exemplary embodiments, I(x) is the continuous valued pixel intensity at pixel x. Within each blob, I(x) are modeled as independent. Note that because the model is used to classify wall composition in 3D radiological images, the word "pixel" is used to generically denote both 2D pixels and 3D voxels Characteristics of blob regions of like composition/structure may advantageously provide insights regarding the disease process. Each slice (e.g., cross-sectional slice) of a vessel may advantageously include a plurality of blobs. Relationships between blobs may be evaluated in a pairwise manner. The number of blobs within a cross-section is modeled as a discrete random variable and may also be of quantifiable significance. At the slice-level of segmentation, relevant characteristics (e.g., biological properties/analytes) may include a quantification of a total number of blobs and/or a number of blobs of a particular structure/composition classification; relationships between the blobs, e.g., spatial relationships such as being closer to the interior. At the blob level of segmentation, characteristics of each blob, such as structural characteristics, e.g., size and shape, as well as compositional characteristics, etc., may be evaluated serving as a biological properties/analytes. Finally, at a pixel-level of segmentation, individual pixel level analysis may be performed, e.g., based image intensity distribution.

Probability mapping of characteristics may be applied with respect to the multi-scale vessel wall analyte map depicted in FIG. 4. The probability mapping may advantageously establish a vector of probabilities for every pixel with components of the vector for the probability of each class of analyte and one component for the probability of background tissue. In example embodiments, sets of probability vectors may represent mutually exclusive characteristics. Thus, each set of probability vectors representing mutually exclusive characteristics will sum to 1. For example, in some embodiments, it may be known that a pixel should fall into one and only one compositional category (e.g., a single coordinate of a vessel cannot be both fibrous and calcified). Of particular note, the probability mapping does not assume independence of analyte class between pixels. This, is because neighboring pixels or pixels within a same blob may typically have same or similar characteristics. Thus, the probability mapping accounts, as described in greater detail herein, advantageously accounts for dependence between pixels.

f(A=α) may be defined as the probability density of map α. f(A) is the probability distribution function over all vessel walls. $f(D_B\{B^a\}=\beta)$ is the probability density of descriptor vector β with label a. $f(D_B\{B^a\})$ is the probability density function (pdf) of blob descriptors with label a. There is a probability distribution function for each value of a. $f(B) = \Pi f(D_B\{B^a\})$ $f(D_c\{C^{f,g}\}=\gamma)$ is the probability density of pairwise descriptor vector γ with labels f and g. $f(D_c\{C^{f,g}\})$ is the probability density function (pdf) of pairwise blob descriptors. There is a probability distribution function for each ordered pair f,g. Thus:

$$f(C) = \Pi f(D_c\{C^a\})$$

$$f(A) = f(B)f(C) = \Pi f(D_b\{B^a\})\Pi f(D_c\{C^a\})$$

P(A(x)=α) is the probability of pixel x having label a. P(A(x)) is the probability mass function (pmf) of analytes (prevalence). It can be considered a vector of probabilities at a specific pixel x or as a probability map for a specific class label value. Note that:

$$f(A) = P(N) \cdot f(C) \cdot f(B) = P(N) \Pi f(C_c) \Pi f(B_b)$$

$f(C_c=\gamma)$ is the probability density of pairwise descriptor vector γ. $f(C_c)$ is the probability density function (pdf) of pairwise blob descriptors. $f(B_b=\beta)$ is the probability density of descriptor vector β. $f(B_b)$ is the probability density function (pdf) of blob descriptors. P(A(x)=α) is the probability of pixel x having label a. P(A(x)) is the probability mass function (pmf) of analytes (prevalence in a given map). It can be considered a vector of probabilities at a specific pixel x or as a spatial probability map for a specific analyte type. P(A(x)=a|I(x)=i) is the probability of analyte given the image intensity that is our main goal to compute. P(I(x)=i|A(x)=a) is the distribution of image intensities for a given analyte.

Figure 5:
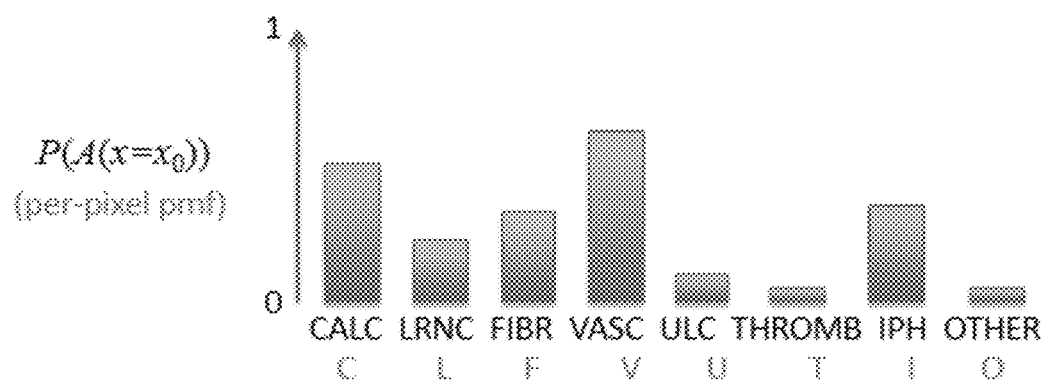
FIG. 5 depicts an exemplary pixel-level probability mass function as a set of analyte probability vectors, according to the present disclosure.

FIG. 5 depicts an exemplary pixel-level probability mass function as a set of analyte probability vectors. As noted above, the following assumptions may inform the probability mass function: Completeness: in example embodiments one may assume a sufficiently small pixel must fall into at least one of the analyte classes (including a catch-all 'background' category) and thus the sum of probabilities sums to 1. Mutual exclusivity: a sufficiently small pixel may be assumed to belong to only one class of analyte; if there are combinations (i.e., spiculated calcium on LRNC background), then a new combination class can be created in order to retain mutual exclusivity. Non-independence: each pixel may be assumed to be highly dependent on its neighbors and the overall structure of A.

An alternative view of the analyte map is as a spatial map of probability for a given analyte. At any given point during inference, analyte blobs can be defined using the full width half max rule. Using this rule, for each local maxima of probability for that analyte a region is grown outward to a lower threshold of half the local maxima value. Note that this 50% value is a tunable parameter. Spatial regularization of blobs can be done here by performing some curvature evolution on probability maps in order to keep boundaries more realistic (smooth with few topological holes). Note that different possible putative blobs of different analyte classes may in general have spatial overlap because until one collapses the probabilities these represent alternative hypotheses for the same pixel and hence the modifier 'putative'.

When iterative inference is terminated, there are several options for presentation of the results. First, the continuously valued probability maps can be presented directly to the user in one of several forms including but not limited to surface plots, iso-contour plots, or using image fusion similar to visualizing PET values as variation in hue and saturation on top of CT. A second alternative is to collapse the probability map at each pixel by choosing a single analyte label for each pixel. This can be done most straightforwardly by choosing the maximum a posteriori value at each pixel independently, thus creating a categorical map which could be visualized by assigning a distinct color to each analyte label and assigning either full or partial opacity on top of the radiological image. Under this second alternative, the label values might be assigned non-independently by resolving overlapping putative blobs based on a priority the probability of each blob. Hence, at a given pixel a lower priority analyte probability might be used for the label if it belongs to a higher probability blob.

FIG. 6 illustrates a technique for computing putative analyte blobs. In example embodiments putative blobs may have overlapping regions. Thus, it may be advantageous to apply analytical techniques to segmenting pixels by putative blobs. For a probability of a given analyte the local maxima in probability is determined. The full width half max rule may then be applied to determine discrete blobs. At any given iteration of inference, analyte blobs can be defined using the full width half max rule. Find local maxima, then region grow with a lower threshold of 0.5*max. (The 50% value could be a tunable parameter.) In some embodiments, spatial regularization of blobs may also be applied, e.g., by performing some curvature evolution on probability maps in order to keep boundaries smooth and avoid holes. Note that at this stage different possible putative blobs of different analyte classes may, in general, have spatial overlap because until probabilities are collapsed these represent alternative hypotheses. Thus, an image-level analyte map be computed, e.g., based on a collapse of the probability map function. Notably, this collapse can be determined based on either the pixel-level analyte probability map, the putative blobs or a combination of both. With respect to the pixel-level analyte probability map, collapse can be determined by for each pixel, by choosing the label with maximum probability A(x):=arg maxa P(A(x)=α). This is similar to implementation Viterbi algorithm. Basically, the highest probability for each set of mutually exclusive probabilities vectors is locked in (e.g. with analyte priorities breaking possible ties). All other probabilities in the set may then be set to zero. In some embodiments, probabilities for neighboring pixels/regions may be taken into account when collapsing data on a pixel level. With respect to putative blob level collapse, overlapping putative blobs may be resolved. In some embodiments, prioritization can be based on blob probability density $f(D_1\{A_a^b\}=d_1)$. Since higher probability blobs may change shape of overlapped lower probability blob this may impact analysis of blob level characteristics. In example embodiments, the full range of probabilities may be maintained rather than collapsing the data.

In order to model the relative spatial positioning of blobs within the vessel wall, an appropriate coordinate system can be chosen in order to provide rotational-, translational-, and scale-invariance between different images. These invariances are important to the model because they allow the ability to train on one type of vessel (e.g., carotids where endarterectomy specimens are easily available) and apply the model to other vessel beds (e.g., coronary where plaque specimens are generally not available) under the assumption that the atherosclerotic process is similar across different vessel beds. For tubular objects, a natural coordinate system follows from the vessel centerline where distance along the centerline provides a longitudinal coordinate and each plane perpendicular to the centerline has polar coordinates of radial distance and angle. However, due to the variability of vessel wall geometry, especially in the diseased patients, which one may aim to analyze, an improved coordinate system may be utilized. The longitudinal distance is computed in a way so that each 3D radiological image pixel is given a value, not just along the centerline or along interpolated perpendicular planes. For a given plaque, the proximal and distal planes perpendicular to the centerline are each used to create an unsigned distance map on the original image grid, denoted P(x) and D(x), respectively where x represents the 3D coordinates. The distance map l(x)=P(x)/(P(x)+D(x)) represents the relative distance along the plaque with a value of 0 at the proximal plane and 1 at the distal plane. The direction of the 1-axis is determined by $\nabla l(x)$.

Because the geometry of the wall may be significantly non-circular, the radial distance may be defined based on the shortest distance to the inner luminal surface and the shortest distance to the outer adventitial surface. The expert-annotation of the histology images includes regions that define the lumen and the vessel (defined as the union of the lumen and vessel wall). A signed distance function can be created for each of these, L(x) and V(x), respectively. The convention is that the interior of these regions is negative so that in the wall L is positive and V is negative. The relative radial distance is computed as r(x)=L(x)/(L(x)−V(x)). It has a value of 0 at the luminal surface and 1 at the adventitial surface. The direction of the r-axis is determined by $\nabla r(x)$.

Because of the non-circular wall geometry, the normalized tangential distance may be defined as lying along iso-contours of r (and of l if processing in 3D). The direction of the t-axis is determined by $\nabla r \times \nabla l$. The convention is that histology slices are assumed to be viewed looking from the proximal to the distal direction so that positive l points into the image. Note that unlike the others, t does not have a natural origin since it wraps onto itself around the vessel. Thus, one can define the origin of this coordinate differently for each blob relative to the centroid of the blob.

Another wall coordinate that is used is normalized wall thickness. In some sense, this is a proxy for disease progression. Thicker wall is assumed to be due to more advanced disease. Assumption that statistical relationship of analytes changes with more advanced disease. The absolute wall thickness is easily calculated as $w_{abs}(L(x)-V(x)$. In order to normalize it to the range of [0-1], one may determine that maximum possible wall thickness when the lumen approaches zero size and is completely eccentric and near the outer surface. In this case the maximum diameter is the maximum Feret diameter of the vessel, $D_{max}$. Thus, the relative wall thickness is computed as $w(x)=w_{abs}(x)/D_{max}$.

The degree to which the aforementioned coordinates may or may not be used in the model is in part dependent on the amount of training data available. When training data is limited, several options are available. The relative longitudinal distance may be ignored treating different sections through each plaque as though they come from the same statistical distribution. It has been observed that plaque composition changes along the longitudinal axis with more severe plaque appearance in the middle. However, instead of parameterizing the distributions by l(x), this dimension can be collapsed. Similarly, the relative wall thickness may also be collapsed. Observations have been made that certain analytes occur in "shoulder" regions of plaques where w(x) would have a middle value. However, this dimension can also be collapsed until enough training data is available.

As noted above, a vessel wall composition model may be utilized as the initial hypothesis (e.g., at the prior P(A)). FIG. 7 depicts normalized vessel wall coordinates for an exemplary vessel wall composition model. In the depicted model, l is relative longitudinal distance along vessel target from proximal to distal, which may be calculated, e.g., on a normalized the interval [0,1]. The longitudinal distance may be computed with 2 fast marching propagations starting from proximal and from distal planes to compute unsigned distance fields P and D wherein l=P/(P+D). l-axis direction is $\nabla l$. As depicted, r is normalized radial distance which may also be calculated on a normalized interval [0,1] from luminal to adventitial surface. Thus, $r=L/(L+(-V))$ where L is lumen signed distance field (SDF) and V is vessel SDF. r-axis direction is $\nabla r$. Finally, t is normalized tangential distance which may be computed, e.g., on a normalized interval [−0.5,0.5]. Notably, in example embodiments there is may be no meaningful origin for the entire wall, only for individual analyte blobs (thus, t origin may be at blob centroid). The tangential distance is computed along isocontour curves of l and of r. t-axis direction is $\nabla r \times \nabla l$.

Figure 9:
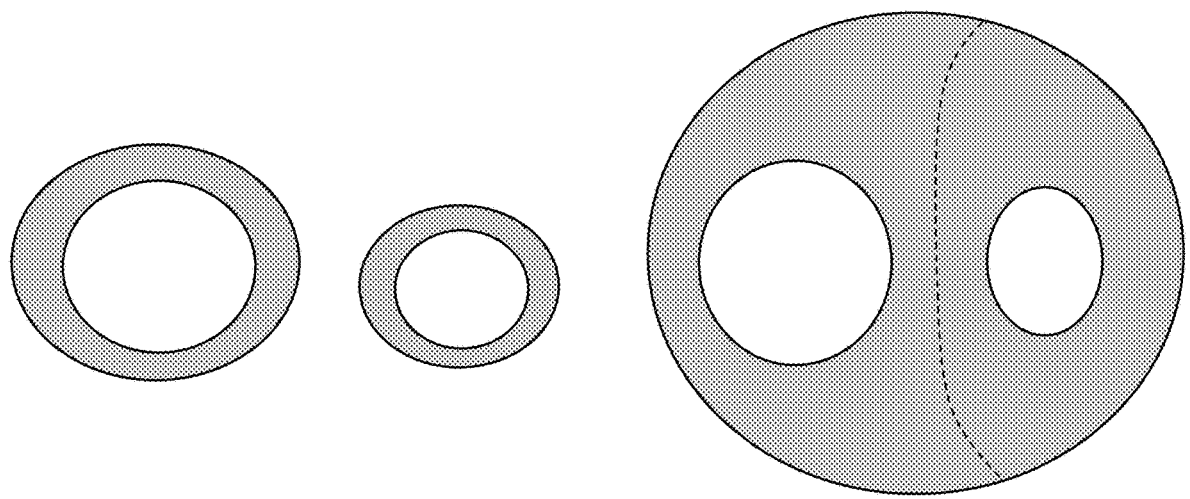
FIG. 9 illustrates some complex vessel topologies which can be accounted for using the techniques described herein, according to the present disclosure.

FIG. 9 illustrates some complex vessel topologies which can be accounted for using the techniques described herein. In particular, when processing CT or MR in 3D, different branches may be advantageously analyzed separately so that the relationship between analyte blobs in separate branches are properly ignored. Thus, if a segmented view (cross-sectional slice) If includes more than one lumen, one can account for this by performing a watershed transform on r in order to split up wall into domains belonging to each lumen after which each domain may be separately considered/analyzed.

As noted above, many of the coordinates and probability measurements described herein may be represented utilizing normalized scales thereby preserving scale invariance, e.g., between different sized vessels. Thus, the proposed model may advantageously be independent of absolute vessel size, under the assumption that a disease process is similar and proportional for different caliber vessels.

In some embodiments, the model may be configured to characterize concentric vs. eccentric plaque. Notably, a normalized all thickness close to 1 may indicate highly eccentric place. In further embodiments, inward vs. outward plaque characterization may be implemented. Notably, histological information on this characteristic is hindered by deformation. Thus, in some embodiments, CT and training data may be utilized to establish an algorithm for determining inward vs. outward plaque characterization.

Figure 8:
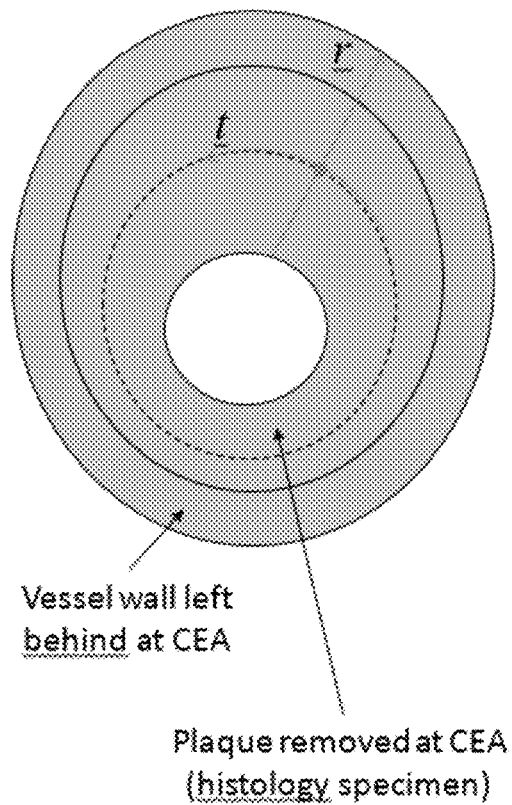
FIG. 8 depicts an example margin between plaque removed for a histology specimen and the outer vessel wall, according to the present disclosure.

As noted above, in example embodiments, non-imaging data, such as histology data, may be utilized as a training set for establishing algorithms linking image features to biological properties/analytes. There are however, some differences between the data types that need to be addressed in ensuring a proper correlation. For example, the following differences between histology and imaging may impact proper correlation: Carotid endarterectomy (CEA) leaves adventitia and some media behind in patient CT or MR image analysis presumed to find outer adventitial surface. (See e.g., FIG. 8 depicting the margin between the plaque removed for the histology specimen relative to the outer vessel wall). Notably, scientific literature shows uncertainty of whether calcification can occur in adventitia. The following techniques may be employed to account for this difference. Histology can be dilated outward, e.g., based on an assumption that little to no analyte in the wall is left behind. Alternatively, Image segmentation can be eroded inward, e.g., based on knowledge of typical or particular margins left. For example, an average margin may be utilized. In some embodiment an average margin may be normalized a percentage of the overall diameter of the vessel. In further embodiments, histology may be used to mask the imaging (e.g., overlay, based on alignment criteria). In such embodiments it may be necessary to apply one or more transformations to the histology data to match proper alignment. Finally, in some embodiments, the difference may be ignored (which is equivalent to uniform scaling of removed plaque to entire wall). While this may induce some small error, presumably the wall left behind may be thin compared to plaque in CEA patients.

Longitudinal differences may also exist between histological data (e.g., a training set) and the imaging data as represented by the vessel wall composition model. In example embodiments, longitudinal distance may be modeled/correlated explicitly. Thus, e.g., histology slice numbering (A-G for example) can be used to roughly determine position within excised portion of plaque. This approach, however, limits analysis with respect to other slices without corresponding histology data. Thus, alternatively, in some embodiments, all histology slices may be treated as arising from the same distribution. In example embodiments, some limited regularization may still be employed along the longitudinal direction.

As noted above, normalized wall thickness, in some sense is an imperfect proxy for disease progression. In particular, a thicker wall is assumed to be due to more advanced disease, e.g. based on an assumption that statistical relationship of analytes changes with more advanced disease. Normalized wall thickness may be calculated as follows: An absolute wall thickness $T_a$ may be determined (in mm), e.g., computed as $T_a=L+(-V)$ where L is lumen SDF, V is vessel SDF and $D_{max}$ is maximum Feret diameter of vessel (in mm). A relative wall thickness T may then be computed based on $T=T_a/D_{max}$, e.g., on an interval [0,1], where 1 indicates thickest part of small lumen indicative of completely eccentric plaque. In example embodiments, probabilities may be conditioned based on wall thickness, e.g., so that the distribution of analyte blobs would depend on wall thickness. This advantageously may model differences in analyte composition over the course of disease progression.

FIG. 10 depicts representing an exemplary analyte blob with a distribution of normalized vessel wall coordinates. In particular, the origin of t is placed at blob centroid. (r,t) coordinates are a random vector where the location/shape is fully represented by the joint distribution of points within. This can be simplified by considering the marginal distributions (since radial and tangential shape characteristics seem relatively independent). Marginal distributions may be calculated as projections along r and t (note that l and T coordinates can also be considered). Notably, the marginal distribution in the radial direction may advantageously represent/characterize the plaque growth in concentric layers (e.g., medial layer, adventitial layer and intima layer.) Similarly, the marginal distribution in the tangential direction may advantageously represent a growth factor which may be indicative of the staging of the disease. In example embodiments, analyte blob descriptors can be computed based on the marginal distributions. For example, on can take low order statistics on the marginal distributions (or use histograms or fit parametric probability distribution functions). In example embodiments, the following analyte blob descriptors may be used, e.g., to capture location, shape or other structural characteristics of individual blobs:

Location in normalized vessel coordinates
  Mostly with respect to r
    e.g., in order to distinguish between shallow/deep calcification
    t-direction ignored; [optionally model 1-direction]
Extent in normalized vessel coordinates
  Intentionally avoiding the word 'size' which implies an absolute measurement, whereas extent is a normalized value
Lopsidedness to represent degree of asymmetry in distribution
  Clinical significance is unclear but it may help to regularize shapes against implausible lopsided shapes
Alignment to represent confinement to parallel tissue layers
  Analyte blobs seem to stay within radial layers (iso-contours of r) quite well so this will help select image processed shapes that are similar
Wall thickness where the blob is located
  Thick (i.e., advanced) plaques assumed to have different statistics than thin plaques
In some embodiments, pair-wise blob descriptors may also be utilized. For example:
Relative location
  e.g., if fibrosis is on the lumen side of LRNC
Relative extent
  e.g., how thick/wide is fibrosis relative to LRNC Surroundedness
  How much one marginal projection falls close to the middle of the other
  e.g., napkin ring sign or fibrosis around LRNC
Relative wall thickness
  To represent degree of shoulderness' (shoulder would be relatively less thick than central plaque body)

It is noted that higher order interactions (e.g., between three blobs or between two blobs and another feature), may also be implemented. However, consideration may be given to diminishing returns and training limitations.

The following are example quantifications of blob descriptors:
Individual blob descriptors

| Location | $\alpha_r = E[r]$ | |
| Extent | $\beta_r = Var[r]$ | $\beta_t = Var[t]$ |
| Lopsidedness | $\gamma_r = |Skewness[r]|$ | $\gamma_t = |Skewness[t]|$ |
| Alignment | $\delta_r = Kurtosis[r]$ | $\delta_t = Kurtosis[t]$ |
| Thickness | $\tau_T = E[T]$ | |

Pairwise blob descriptors

| Relative location | $\alpha_{rr} = E[r_2] - E[r_1]$ | $\alpha_{tt} = E[t_2] - E[t_1]$ |
| Relative extent | $\beta_{rr} = Var[r_2]/Var[r_1]$ | $\beta_{tt} = Var[t_2]/Var[t_1]$ |
| Surroundedness | $\varepsilon_{rr} = |\alpha_{rr}| \beta_{rr}$ | $\varepsilon_{tt} = |\alpha_{tt}| \beta_{tt}$ |
| Relative thickness | $\tau_{TT} = E[T_2]/E[T_1]$ | |

Notably, the set of descriptors (e.g., 8-12 descriptors) form a finite shape space that a blob lives in. One can then look at the distribution of a population of blobs as a distribution in this finite space. FIG. 11 depicts an exemplary distribution of blog descriptors. In example embodiments the distribution of blob descriptors may be computed over the whole training set. In some embodiments, lower order statistics may be utilized on individual blob descriptors (assuming independence), e.g., Location: $E[\alpha_r]$, $Var[\alpha_r]$. In other embodiments, a multi-dimensional Gaussian (mean vector+covariance matrix) analysis may be used to model the descriptors (e.g., wherein independence is not assumed). In further embodiments, if the distribution is non-normal it may be modeled with density estimation techniques.

Figure 14:
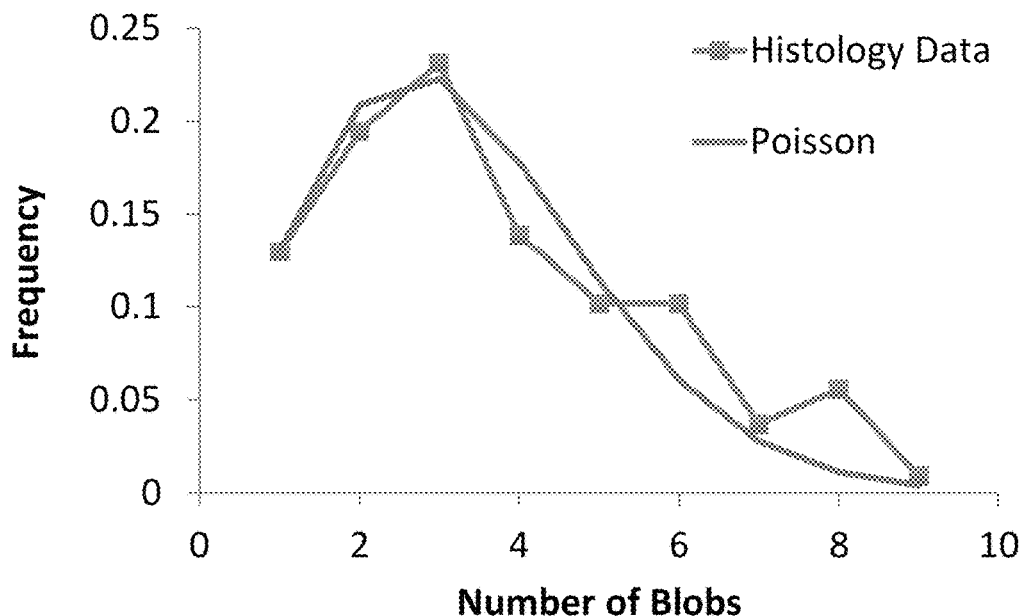
FIG. 14 depicts an example frequency distribution of total number of blobs per histological slide for a plurality of histological slides, according to the present disclosure.

As noted above, one can also model a number of blobs per cross section (or the number of each class), e.g., $\eta$ without regard to analyte class and $\eta_i$ counting number in each analyte class. FIG. 14 depicts frequency distribution of the total number of blobs for each histology slide. A poison regression is applied as an overly. Note that the analytic chart of FIG. 14 depicts the number of blobs per cross section N without regard to analyte class (number of blobs of each analyte type is represented by B).

Summarizing the forgoing sections, in example embodiments, the overall vessel wall composition model may include the following:
Per-pixel analyte prior pmf
  $P(A(x)=a_i)=\rho_i$
Individual blob descriptors
  $B_1=(\alpha_r, \beta_r, \beta_t, \gamma_r, \gamma_t, \delta_r, \delta_t, \tau_T)$
  $B_1 \sim N(\mu_1, \Sigma_1)$
Pairwise blob descriptors
  $C_2=(\alpha_{rr}, \alpha_{tt}, \beta_{rr}, \beta_{tt}, \varepsilon_{rr}, \varepsilon_{tt}, \tau_{TT})$
  $C_2 \sim N(\mu_2, \tau_2)$
Number of blobs
  $\eta \sim Poisson(\lambda_\eta)$ wherein:

$$P(A(x) = a_i) = \rho_i$$

$$f(A^b) = f(B_1^b)$$

$$f(A) = P(\eta) \cdot \left(\prod_{b \neq c} f(C_2^{bc})\right) \cdot \prod_b f(A^b)$$

Figure 12:
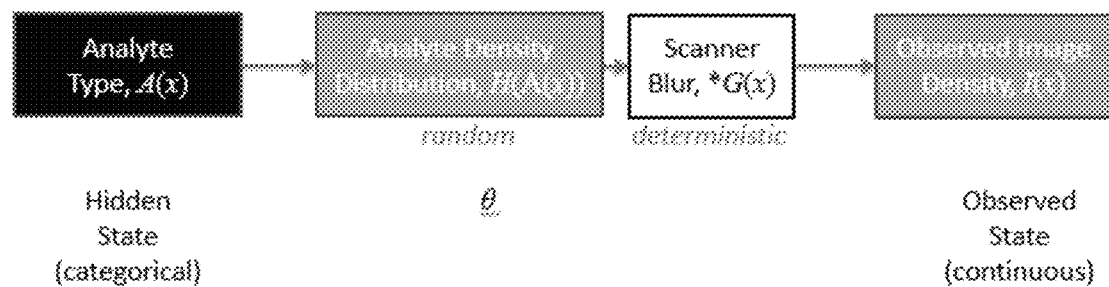
FIG. 12 depicts an exemplary model for imaging data correlating between a hidden ground truth state and an observed state, according to the present disclosure.

As noted above, an imaging model may serve as the likelihood (e.g., P(I\A)) for the Bayesian analytic model. A maximum likelihood estimate may then be determined. In example embodiments, this may be done considering each pixel in isolation (e.g., without regard to the prior probability of the structure in the model). Estimated analyte maps are typically smooth only because images are smooth (which is why no prior smoothing is typically performed). Independent pixel-by-pixel analysis can be done, e.g., at least up to the point of accounting for scanner PSF. The imaging model is utilized to account for imperfect imaging data. For example, imaging small components of plaque adds independent noise on top of pixel values. Moreover, the partial volume effect and scanner PSF are well known as applying to small objects. Thus, given a model (e.g., level set representation of analyte regions), simulating CT by Gaussian blurring with PSF is easy and fast. The imaging model described herein may also be applied to determine (or estimate) the distribution of true (not blurred) densities of different analytes. Notably this cannot come from typical imaging studies since these will have blurred image intensities. In some embodiments, wide variances could be used to represent the uncertainty. Alternatively, distribution parameters could be optimized from training set but the objective function would have to be based on downstream readings (of analyte areas), e.g., unless aligned histology data is available. FIG. 12 depicts the exemplary model for imaging data (e.g., correlating between a hidden (categorical) state (A(x)) and an observed (continuous) state (I(x)) whereby random (e.g., analyte density distribution (H(A(x))) and deterministic (e.g., scanner blur*G(x)) noise factors are accounted for. θ are the parameters of H (proportion & HU mean/variance of each analyte). θ=($\tau_I, \mu_I, \sigma_I, \ldots, \tau_N, \mu_N, \sigma_N$) for N different analyte classes assuming normal distributions. Note that θ are patient specific and will be estimated in an expectation maximization (EM) fashion, e.g., wherein analyte labels are the latent variables and the image is observed data.

E-step: determine membership probabilities given current parameters

M-step: maximize likelihood of parameters given membership probabilities

Figure 13:
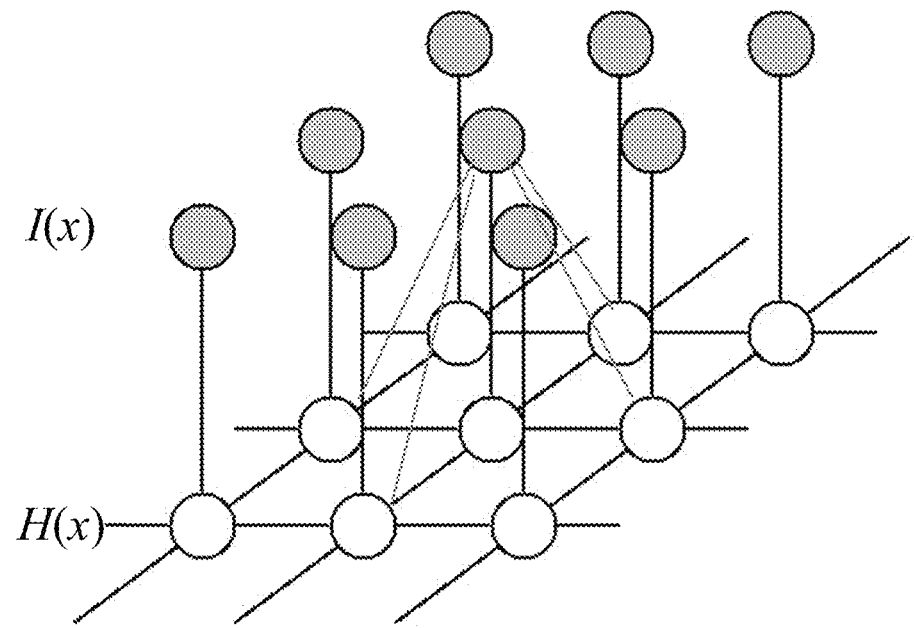
FIG. 13 depicts a diagram of an example Markov model/Viterbi algorithm for relating an observed state to a hidden state in an image model, according to the present disclosure.

FIG. 13 depicts a diagram of an example Markov model/Viterbi algorithm for relating an observed state to a hidden state in an image model. In particular, the diagram depicts an observed state (gray) (observed image intensity, I(x)) and a hidden state (white) (pure analyte intensity, H(A(x))) which can be modeled either with empirical histogram or with Gaussian or boxcar probability distribution function. PSF of imaging system is modeled as Gaussian, G(x). Thus, $$I(x) = G(x) * H(A(x))$$

It is noted that a Viterbi-like algorithm could apply here but convolution would replace emission probabilities H could be modeled as Gaussian or uniform.

As noted above, one portion of the inference procedure is based upon expectation maximization (EM). In a typical application of EM, data points are modeled as belonging to one of several classes, which is unknown. Each data point has a feature vector and for each class, this feature vector may be modeled with a parametric distribution such as a multidimensional Gaussian, represented by a mean vector and a covariance matrix. In the context of the model presented herein, a straightforward EM implementation would work as follows:

$$L(\theta; I) = \prod_{x=1}^{N_{pixels}} \sum_{a=1}^{N_{analytes}} \tau_a G(I(x); \mu_a, \sigma_a) \text{ where } G \text{ is Gaussian function}$$

$$L(\theta; I, A) = p(I, A \mid \theta)$$

$$= \prod_{x=1}^{N_{pixels}} \sum_{a=1}^{N_{analytes}} \delta_{a,A(x)} \tau_a G(I(x); \mu_a, \sigma_a)$$

where $\delta$ is Kronecker delta $$= \exp\left\{\sum_{x=1}^{N_{pixels}} \sum_{a=1}^{N_{analytes}} \delta_{a,A(x)} \left[\ln \tau_a - \frac{\ln(2\pi\sigma_a^2)}{2} - \frac{(I(x) - \mu_a)^2}{2\sigma_a^2}\right]\right\}$$

$$T_{j,x}^{(t)} := P(A(x) = j \mid I = I(x); \theta^{(t)}) =$$

$$\frac{\tau_j^{(t)} G(I(x); \mu_j^{(t)}, \sigma_j^{(t)})}{\sum_{a=1}^{N_{analytes}} \tau_a^{(t)} G(I(x); \mu_a^{(t)}, \sigma_a^{(t)})} \text{ (membership probabilities)}$$

$$Q(\theta \mid \theta^{(t)}) = E[\ln L(\theta; I, A)]$$

$$= E\left[\ln \prod_{x=1}^{N_{pixels}} L(\theta; I(x), A(x))\right]$$

$$= \sum_{x=1}^{N_{pixels}} E[\ln L(\theta; I(x), A(x))]$$

$$= \sum_{a=1}^{N_{analytes}} \sum_{x=1}^{N_{pixels}} T_{a,x}^{(t)} \left[\ln \tau_a - 1 \frac{\ln(2\pi\sigma_a^2)}{2} - \frac{(I(x) - \mu_a)^2}{2\sigma_a^2}\right]$$

$$\tau^{(t+1)} = \operatorname*{argmax}_{\tau} \left\{\sum_{a=1}^{N_{analytes}} \left(\left[\sum_{x=1}^{N_{pixels}} T_{a,x}^{(t)}\right] \ln \tau_a\right)\right\}$$

$$\tau_j^{(t+1)} = \frac{1}{N_{pixels}} \sum_{x=1}^{N_{pixels}} T_{j,x}^{(t)}$$

$$(\mu_j^{(t+1)}, \sigma_j^{(t+1)}) =$$

$$\operatorname*{argmax}_{\mu,\sigma} \left\{\sum_{a=1}^{N_{analytes}} \left(\left[\sum_{x=1}^{N_{pixels}} T_{a,x}^{(t)}\right]\left[-1\frac{\ln(2\pi\sigma_a^2)}{2} - \frac{(I(x) - \mu_a)^2}{2\sigma_a^2}\right]\right)\right\}$$

$$\mu_j^{(t+1)} = \frac{\sum_{x=1}^{N_{pixels}} T_{j,I(x)}^{(t)} I(x)}{\sum_{x=1}^{N_{pixels}} T_{j,I(x)}^{(t)}} \quad \sigma_j^{(t+1)} = \frac{\sum_{x=1}^{N_{pixels}} T_{j,I(x)}^{(t)}(I(x) - \mu_j^{(t+1)})^2}{\sum_{x=1}^{N_{pixels}} T_{j,I(x)}^{(t)}}$$

The main problem with this simple model is that it doesn't code any higher order structure to the pixels. There is no prior probability associated with more realistic arrangements of pixels. Only tau determines the proportion of analyte classes. Thus, once can use the tau variable to insert in the blob prior probability model, in particular at the step of updating membership probabilities.

Thus, a modified Bayesian inference procedure may be applied with a much more sophisticated Bayesian prior. In the basic EM implementation, there is no real prior distribution. The variable tau represents the a priori relative proportion of each class but even this variable is unspecified and estimated during the inference procedure. Thus, there is no a priori belief about the distribution of classes in the basic EM model. In our model, the model prior is represented by the multi-scale analyte model. Tau becomes a function of position (and other variables), not just a global proportion.

$$L(\theta; I, A) = f(I, A \mid \theta) = f(A) f(I \mid A, \theta) =$$

$$f(A) \prod_{x=1}^{N_{pixels}} G(I(x); \mu_{A(x)}, \sigma_{A(x)})$$

$$= f(A) \exp \left\{ \sum_{x=1}^{N_{pixels}} -\frac{\ln(2\pi\sigma_a^2)}{2} - \frac{(I(x) - \mu_a)^2}{2\sigma_a^2} \right\}$$

$$Q(\theta \mid \theta^{(t)}) = E[\ln L(\theta; I, A)]$$

$$= E \left[ \ln f(A) + \sum_{x=1}^{N_{pixels}} -\frac{\ln(2\pi\sigma_a^2)}{2} - \frac{(I(x) - \mu_a)^2}{2\sigma_a^2} \right]$$

$$= E[\ln f(A)] +$$

$$\sum_{a=1}^{N_{analytes}} \sum_{x=1}^{N_{pixels}} T_{a,x}^{(t)} \left[ -1 \frac{\ln(2\pi\sigma_a^2)}{2} - \frac{(I(x) - \mu_a)^2}{2\sigma_a^2} \right]$$

$$(\mu_j^{(t+1)}, \sigma_j^{(t+1)}) =$$

$$\operatorname*{argmax}_{\mu, \sigma} \left\{ \sum_{a=1}^{N_{analytes}} \left( \left[ \sum_{x=1}^{N_{pixels}} T_{a,x}^{(t)} \right] \left[ -1 \frac{\ln(2\pi\sigma_a^2)}{2} - \frac{(I(x) - \mu_a)^2}{2\sigma_a^2} \right] \right) \right\}$$

$$\mu_j^{(t+1)} = \frac{\sum_{x=1}^{N_{pixels}} T_{j,I(x)}^{(t)} I(x)}{\sum_{x=1}^{N_{pixels}} T_{j,I(x)}^{(t)}} \quad \sigma_j^{(t+1)} = \frac{\sum_{x=1}^{N_{pixels}} T_{j,I(x)}^{(t)} (I(x) - \mu_j^{(t+1)})^2}{\sum_{x=1}^{N_{pixels}} T_{j,I(x)}^{(t)}}$$

The membership probability function is defined as follows:

$$f(I, A \mid \theta) = f(A) f(I \mid A, \theta) = f(A) \prod_{x=1}^{N_{pixels}} G(I(x); \mu_{A(x)}, \sigma_{A(x)})$$

$$f(A \mid I, \theta) = \frac{1}{Z} f(A) f(I \mid A, \theta)$$

$$P\left(A(x) = j \mid I(x) = i, \theta\right) = \frac{1}{Z} P(A(x) = j) f(I(x) = i \mid A(x) = j, \theta)$$

$$T_{j,x}^{(t)} := P(A(x)^{(t)} = j \mid I(x) = i, \theta)$$

$$T_{j,x}^{(t)} := \frac{P(A(x)^{(t)} = j) G(I(x); \mu_j^{(t)}, \sigma_j^{(t)})}{\sum_{a=1}^{N_{analytes}} P(A(x)^{(t)} = a) G(I(x); \mu_a^{(t)}, \sigma_a^{(t)})}$$

(membership probabilities)

-continued $$T_{j,x}^{(t)} := \frac{1}{Z} E_{models} [P(A(x) = j) P(I(x) = i \mid A(x) = j, \theta)]$$

$$:= \frac{1}{Z} \sum_{\alpha \in models} P(A = \alpha) P(A(x) = j) P(I(x) = i \mid A(x) = j, \theta)$$

$$:= \frac{1}{Z} \sum_{\alpha \in models} P(N) \prod f(C_c) \prod f(B_b) P(A(x) = j) P(I(x) = i \mid A(x) = j, \theta)$$

The inference algorithm is as follows. At each step of iteration, the membership probability map is initialized to zero so that all classes have zero probability. Then for all possible model configurations, the membership probability map may be added to as follows:

$$T_{j,x}^{(t)} \mathrel{+}= P(N^{(t)}) \Pi f(C_c^{(t)}) \Pi f(B_b^{9,t}) P(A(x)^{(t)}=j) P(I(x)=i \mid A(x)^{(t)}=j, \theta)$$

Finally, the probability vector may be normalized at each pixel in the membership probability map to restore the completeness assumption. Advantageously one can iterate over all model configurations. This is done by sequentially considering values for N from 0 to a relatively low value, for instance 9, at which point extremely few sections have ever been observed to have as many blobs. For each value of N, one can examine different putative blob configurations. The putative blobs may be thresholded to a small number (N) based on their individual blob probabilities. Then, all of the permutations of N blobs are considered. Thus, one can simultaneously considering all of the most likely blob configurations and weighting each model by its prior probability. This procedure is obviously an approximate inference scheme since the full space of multi-scale model configurations may not be considered. One can assume, however, that by considering the most likely (in terms of both N and blobs), a good approximation is achieved. This procedure also assumes that the weighted average of the most likely configurations provides a good estimate at each individual pixel. Another alternative is to perform a constrained search of model configurations and select the highest likelihood model as the MAP (maximum a posteriori) estimate.

Further exemplary statistical models (e.g., the posterior P(A\I)) are also described herein. In a CT angiography the following information may be available:
Intensity
  CT Hounsfield units or MR intensities
  Possibly other imaging features
Position relative to anatomy
  Where in the plaque a pixel is
Neighboring pixels
  E.g., for smoothing contours through level sets
Posterior probability may be computed as:

$$P(A \mid I) \propto P(I \mid A) \cdot P(A)$$

Thus, the following image information may influence analyte probability, $A_i(x)$
  I(x) is observed image intensity (possibly a vector)
  T(x) is observed relative wall thickness from image segmentation
  F(x) are CT image features
  S(x) are features of vessel wall shape (e.g., luminal bulge)
  In some embodiments a Metropolis-Hastings like approach may be utilized. In other embodiments a maximum a posteriori approach may be applied.

The following are example algorithmic possibility for a statistical analysis model. In some embodiments, the model may utilize Belief propagation (AKA max sum, max product, sum product messaging). Thus, for example a Viterbi (HMM) type approach may be utilized, e.g., wherein, hidden states are the analyte assignments, A, observed states are the image intensities, I. This approach may advantageously find a MAP estimate may be argmax P(A|I). In some embodiments a soft output Viterbi algorithm (SOVA) may be utilized. Note that reliability of each decision may be indicated by difference between chosen (survivor) path and discarded path. Thus, this could indicate reliability of each pixel analyte classification. In further example embodiments a forward/backward Baum-Welch (HMM) approach may be utilized. For example, one can compute most likely state at any point in time but not the most likely sequence (see Viterbi).

Another possible technique is the Metropolis-Hastings (MCMC) approach, e.g., wherein one repeatedly samples A and weights by likelihood and prior. In some embodiments, a simple MRF version for sampling may be utilized. Note that it may be particularly advantageous to sample the posterior directly. In example embodiments, one can build up per-pixel histograms of analyte class.

Other algorithm possibilities include applying a Gibbs Sampler, Variational Bayes (similar to EM), Mean field approximation, a Kalman filter, or other techniques.

As noted above, in some embodiments an Expectation Maximization (EM) posterior approach may be utilized. Under this approach, observed data X is the imaging values, unknown parameters θ are due to the analyte map (but not including analyte probabilities) and latent variable Z is the analyte probability vector. One key feature of this approach is that it enables iterating between estimating class membership (Z) and model parameters (θ) since they each depend on each other. However, since the analyte map separates out analyte probabilities, the approach may be modified such that the current class membership doesn't have to influence the model parameters (since these are learned this during a training step). Thus, EM basically learning the model parameters as it iterates through the current data. Advantageously, exemplary implementation of the EM approach iteratively compute maximum likelihood but assumes a flat prior.

Techniques are also provided herein for representing longitudinal covariance. Due to wide spacing of histology slices (e.g., 4 mm), sampling may not faithfully capture the longitudinal variation in analytes. However, 3D image analysis is typically performed and presumably there is some true longitudinal covariance. The problem is that histological information typically isn't provided for longitudinal covariance. Nonetheless the exemplary statistical models disclosed herein may reflect a slow variation in longitudinal direction.

Figure 15:
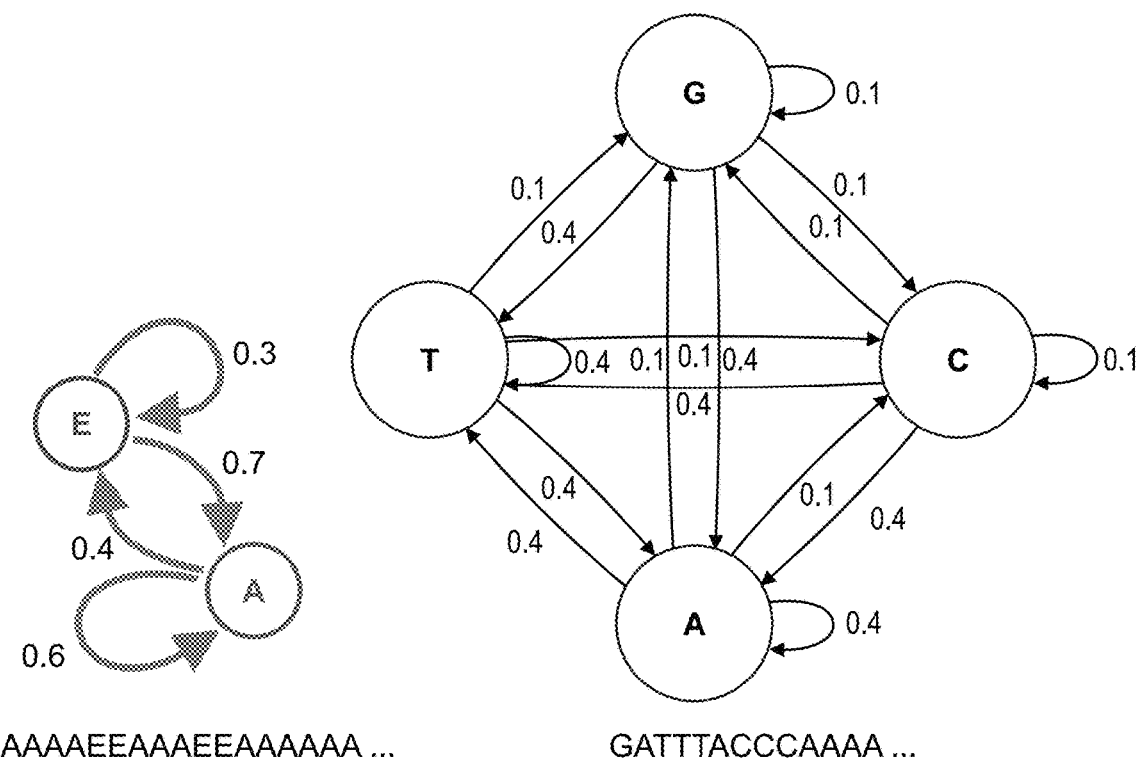
FIG. 15 depicts exemplary implantation of a 1D Markov chain, according to the present disclosure.
Figure 16:
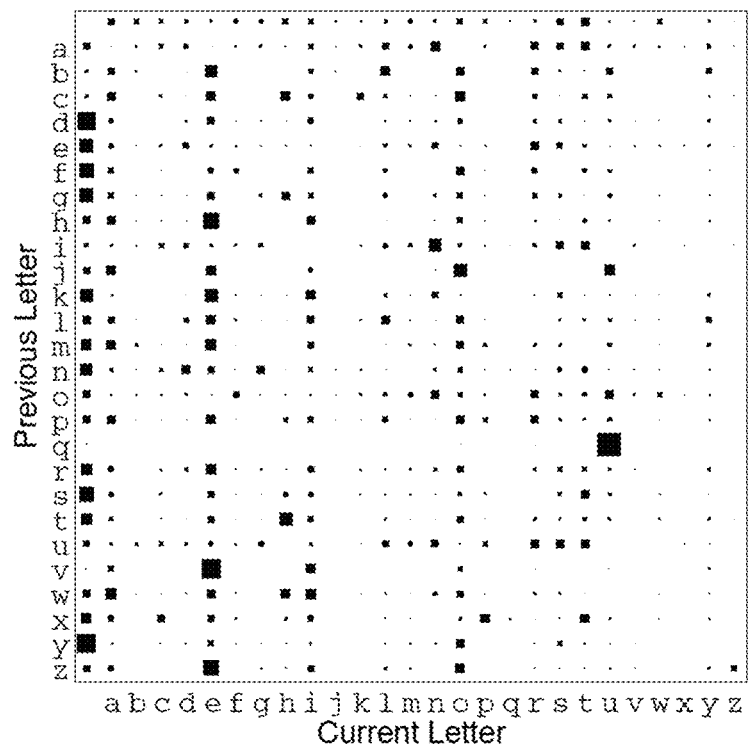
FIG. 16 depicts an example first order Markov chain for a text probability table, according to the present disclosure.

In some embodiments, a Markov model/chain may be applied. FIG. 15 depicts exemplary implantation of a 1D Markov chain for Text/DNA. Conventionally, when applied to images in MRF Markov chains are typical as low order as possible. A higher order chain may be advantageous, however, due to conditional independence (Markov property). Otherwise the data may be too scrambled to be of value. This is demonstrated by the 1D sampling of an exemplary Markov chain as applied to text:

Uniform probability sampling output:
earryjnvanrjakroyvnbqkrxtgashqtzifzstqaqwgktlfgidmxxaxmmhzmgbya mjgxnlyattvcrwpsszwfhimovkvgknlgddounmytnxpvdescbgksyfdhwqdrj jmcovoyodzkcofmlycehpcqpuflje xkcykcwbdaifculiluyqerxfwlmpvtlyqkv 0-order Markov chain output:
ooyusdii eltgotoroo tih ohnnattti gyagditghreay nm roefnnasos r naa euuecocrrfca ayas el s yba anoropnn laeo piileo hssiod idlif beeghec ebnniioouhuehinely neiis cnitcwasohs ooglpyocp h trog l $1^{st}$ order Markov chain output:
icke inginatenc blof ade and j alorghe y at helmin by hem owery fa st sin r d n cke s t w anks hinioro e orin en s ar whes ore jot j whede chrve blan ted sesourethegebe inaberens s ichath fle watt o $2^{nd}$ order Markov chain output:
he ton th a s my caroodif flows an the er ity thayertione wil ha m othenre re creara quichow mushing whe so mosing bloack abeenem used she sighembs inglis day p wer wharon the graiddid wor thad k $3^{rd}$ order Markov chain output:
es in angull o shoppinjust stees ther a kercourats allech is hote ternal liked be weavy because in coy mrs hand room him rolio and ceran in that he mound a dishine when what to bitcho way forgot p FIG. 16 depicts an example first order Markov chain for a text probability table. Note that such tables are exponentially sized in terms of order:

D=order of Markov chain
N=number of letters
Size=$N^D$

Thus, higher order leads to problems with dimensionality. Advantageously histology samples have a very high resolution. However, since histology samples are not statistically independent, this may lead to overfitting as later described in greater detail. In general, the more conditional dependence that is modeled, the more predictive the model can be.

Figure 17:
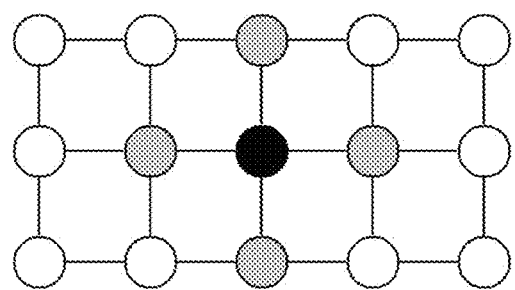
FIG. 17 depicts conditional dependence of a first pixel based on its neighboring pixels, according to the present disclosure.

In example embodiments, a 2D Markov random field (MRF) may be used for pixel values instead of a 1D sequence such as for letters. FIG. 17 depicts conditional dependence of a first pixel (black) based on its neighboring pixels (gray). In example embodiments cliques may make use symmetry to reduce the number of dependencies in half. In some embodiments, the values of pixels could be simple image intensities or could be probability values for classification problems. Problems exist with typical MRF use. Conventional MRF almost always is limited to the nearest neighbor pixels providing conditional dependence which greatly reduces the specificity of the probability space represented; usually just black/white blobs for very general purpose segmentation/filtering; extremely short range dependencies. However, whereas pixels are highly discretized a blob just missing one pixel and falling in the next may completely change the probability distribution. Thus, a real image structure is much more continuous than is typically accounted for using MRF.

For this reasons the systems and methods of the present disclosure may advantageously utilize an inference procedure, e.g., a Bayes type rule of Posterior α Likelihood×Prior (P(A/I) α P(I/A)×P(A)). Using a crossword type analogy, the inference procedure implemented by the systems and methods of the subject application is a bit like trying to OCR a crossword puzzle from a noisy scan. Knowledge (even imperfect knowledge of several squares may help inform an unknown square in the crossword puzzle. Efficiently is improved even more by considering both vertical and horizontal direction simultaneously. In example embodiments, the inference procedure may be heuristic. For example, one can initialize with uninformed prior, then, solve the easier ones first, which gives you clues about the harder ones which are solved later. Thus, relatively easy to detect biological properties such as dense calcium may inform the existence of other harder to detect analytes such as lipids. Each step of the inference procedure may narrow the probability distributions for unsolved pixels.

As noted above a high order Markov chain is preferable to obtain usable data. The disadvantage of utilizing a higher order Markov approach is that there may not be enough data to inform the inference process. In example embodiments, this issue may be addressed by utilizing density estimation methods such as Parzen windowing or utilizing kriging techniques.

To form an inference procedure, one may initialize with unconditional prior probabilities of analytes and then use a highest level of evidence to start narrowing down probabilities. For example, in some embodiments, an uncertain width may be associate with each analyte probability estimate. In other embodiments, closeness to 1/N may represent such uncertainty.

Notably, the term "Markov" is used loosely herein since the proposed Markov implementations are not memoryless but rather are explicitly trying to model long range (spatial) dependencies.

Because the CT resolution is low compared to histology and plaque anatomy, in some embodiments it may be preferable to utilize a continuous space (time) Markov model rather than discrete space (time). This may work well with the level set representation of probability maps since they naturally work well with sub-pixel interpolation. Discrete analyte states makes the model a discrete space model. However, if one represents continuous probabilities rather than analyte presence/absence, then it becomes a continuous space model.

Turning to lung based applications, table 4 below depicts exemplary biological properties/analytes which may utilized with respect to a hierarchical analytics framework for such applications.

TABLE 5

| Biologically-objective measurands Supported by lung based applications | | | |
|---|---|---|---|
| Category | Description | Readings | Units/Categories |
| Size | The size of the lesion | Volume (lesion, solid portion, ground-glass portion) | mm^3 |
| | | Longest diameter and perpendicular (lesion, solid portion, ground-glass portion) | mm |
| Shape/Margin | Overall shape of the lesion and descriptions of its border which may indicate certain cancers or diseases (possibly including fibrotic scarring) | Shape | sphericity (unitless: round = 1, oval ~0.5, line = 0)/lobulated-irregular/cavitary, speculation, notch/cut |
| | | Margin | Tumor margin scale (HU) Tumor margin window (HU/mm) |
| | | Topology | Euler Number |
| Solidity | Mean development of cell types or lack thereof that make up the lesion (differentiation, organization) | Volume % solid of Lesion (C/T ratio) | % |
| | | Volume % ground-glass of Lesion | % |
| | | Solid density | g/ml |
| | | Ground glass density | g/ml |
| | | Mass of solid | g |
| | | Mass of ground glass | g |
| Heterogeneity | Covariance and development of cell types or lack thereof that make up the lesion (differentiation, organization) | SD (variation of solid density) | g/ml |
| | | SD (variation of ground glass) | g/ml |
| | | Pattern | Nonsolid or ground-glass opacity (pure GGN)/perifissural/part-solid (mixed GGN)/solid |
| | | Solid portion pattern | Radial intensity distribution $1^{st}$ and $2^{nd}$ order statistics (Central/central with ring/diffuse/peripheral) |
| | | Spatial coherence (texture, "clumpiness", localized heterogeneity) | NSM (non-spatial methods); SGLM (spatial gray-level methods) e.g., Haralick; fractal analysis (FA): Lacunarity, average local variance, variance of local variance, average of local average; filters & transforms (F&T) e.g., Gabor |
| Invasive Potential | Measure of Lesion's invasive extent or potential extent | Pleural contact length (AKA arch distance) | mm |
| | | Pleural contact length-to-maximum lesion diameter | unitless |
| | | Pleural Involvement | Displacement from expected location |

TABLE 5-continued

Biologically-objective measurands Supported by lung based applications

| Category | Description | Readings | Units/Categories |
|---|---|---|---|
| | | Lobe Location | Upper/middle/lower lobe // right/left |
| | | Lobe centrality | unitless (1 = lobe center, 0 = lobe boundary) |
| | | Airway Involvement/air bronchogram | category |
| | | Vascular changes | Dilated/rigid/convergent/tortuous |
| Calcification | Response to injurious agent (dystrophic) or caused by deranged metabolism (metastatic) | Volume<br>Volume % of Lesion<br>Distribution<br>Pattern | mm^3<br>%<br>Central/peripheral/diffuse<br>amorphous/punctuate/reticular/popcorn/laminated |
| Cell Metabolism | Measures of cell metabolism | Uptake<br>Glycolytc volume | SUV (unitless), % ID/g |
| <each non-categorical measurand above> | Change assessed between as few as 2 but arbitrarily many timepoints | Pairwise arithmetic difference<br>Pairwise ratio<br>Pairwise doubling time<br>Polynomial fit coefficients<br>Non-arithmetic change assessment with registration, e.g., vascular changes | In units of measurand<br><br>unitless<br>days/weeks/months |
| <each non-categorical measurand above> | Assessed over multiple targets according to response criteria, e.g., RECIST, WHO, etc. | Total Tumor Burden<br>Tumor Number<br>Multilobar<br>Lymph Node status<br>Metastasis<br>Response | mm^3<br>unitless<br>True/false<br>category<br>category<br>category |

In particular, systems may be configured to detect lung lesions. Thus, an exemplary system may be configured for whole lung segmentation. In some embodiments, this may involve use of minimum curvature evolution to solve juxtapleural lesion problems. In some embodiments, the system may implement lung component analysis (vessel, fissure, bronchi, lesion etc.). Advantageously a Hessian filter may be utilized to facilitate lung component analysis. In some embodiments lung component analysis may further include pleural involvement, e.g., as a function of fissure geometry. In further embodiments, attachment to anatomic structures may also be considered. In addition to lung component analysis, separate analysis of ground glass vs. solid stated may also be applied. This may include determination of geometric features, such as volume, diameter, sphericity, image features, such as density and mass, and fractal analysis.

Fractal analysis may be used to infer lepidic growth patterns. In order to perform fractal analysis on very small regions of interest, our method adaptively modifies the support for convolution kernels to limit them to the region of interest (i.e., lung nodule). Intersecting vessels/bronchi as well as non-lesion feature may be masked out for the purposes of fractal analysis. This is done by applying IIR Gaussian filters over masked local neighborhoods and normalizing with IIR blurred binary masking. In some embodiments, fractal analysis may further include determining lacunarity (based on variance of the local mean). This may be applied with respect to lung lesions, subparts of lesions. In example embodiments, IIR Gaussian filters or circular neighborhoods may be applied. In some embodiments IIR may be utilized to compute variance. Average of local variance (AVL) may also be computed, e.g., as applied to lung lesions. Likewise, a variance of local variance may be calculated.

In example embodiments, both lesion structure and composition may be calculated. Advantageously calculating lesion structure may utilize full volumetry of thin sections thereby improving on calculating size measurement change. Measurements such as sub-solid and ground glass opacity (GGO) volume may also be determined as part of assessing lesion structure. Turning to lesion composition, tissue characteristics such as consolidation, invasion, proximity and perfusion may be calculated e.g., thereby reducing false positive rate relative to conventional analytics.

Figure 18:
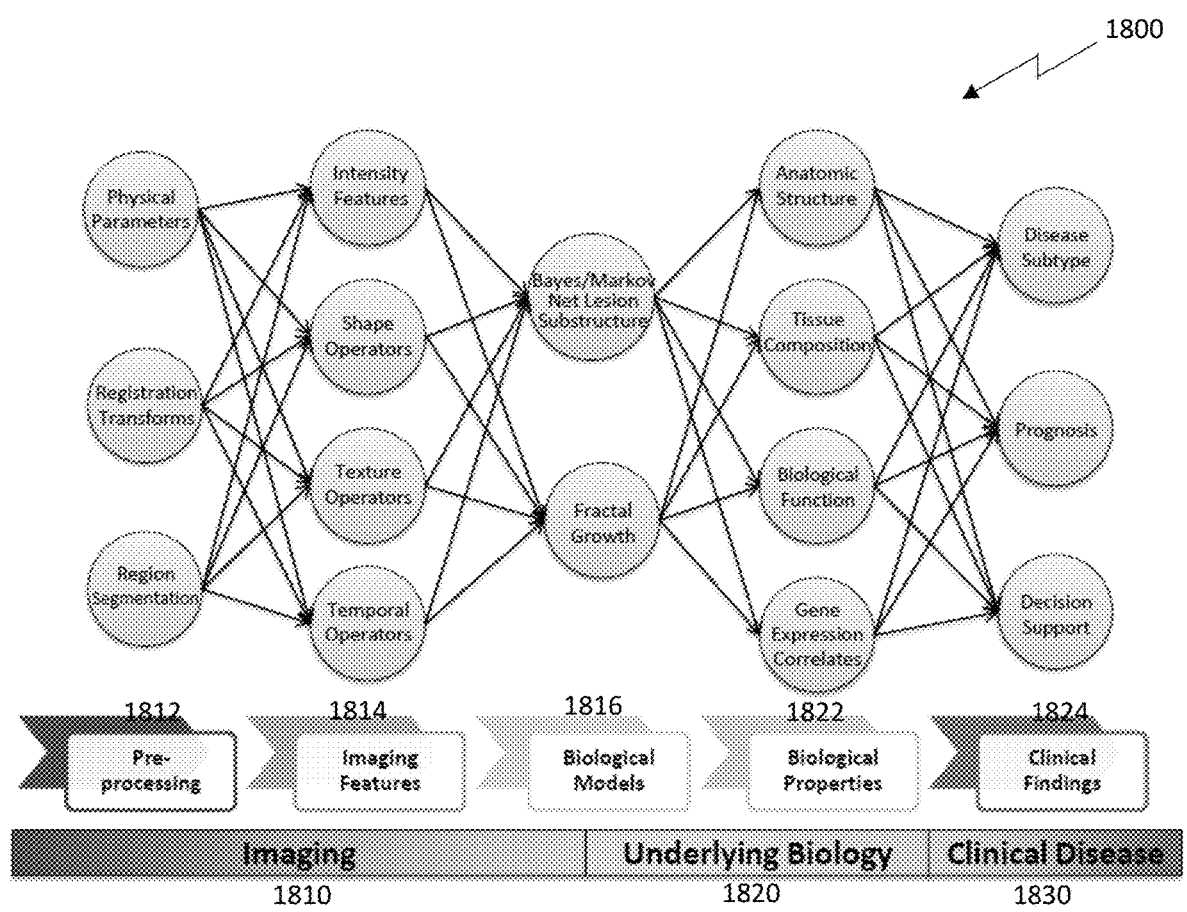
FIG. 18 depicts a further exemplary hierarchical analytics framework according to the present disclosure.

With reference now to FIG. 18, a further exemplary hierarchical analytics framework 1800 for the systems of the present disclosure is depicted. FIG. 18 may be understood as an elaboration of FIG. 1 elucidating greater detail with respect to exemplary intermediate processing layers of the hierarchical inference system. Advantageously the hierarchical inferences still flow from imaging data 1810 to underlying biological information 1820 to clinical disease 1800. Notably, however, the framework 1800 includes multiple levels of data points for processing imaging data in order to determine biological properties/analytes. At a preprocessing level 1812, physical parameters, registrations transformations and region segmentations may be determined. This preprocessed imaging information may then be utilized to extract imaging features at the next level of data points 1814 such as intensity features, shape, texture, temporal characteristics, and the like. Extracted image features may next utilized at level 1816 to fit one or more biological models to the imaged anatomy. Example models may include a Bayes/Markov net lesion substructure, a fractal growth model, or other models such as described herein. The biological model may advantageously act as a bridge for correlating imaging features to underlying biological properties/analytes at level 1822. Example biological properties/analytes include anatomic structure, tissue composition, biological function, gene expression correlates, and the like.

Finally, at level 1832 the biological properties/analytes may be utilized to determine clinical findings related to the pathology including, e.g., related to disease subtype, prognosis, decision support and the like.

Figure 19:
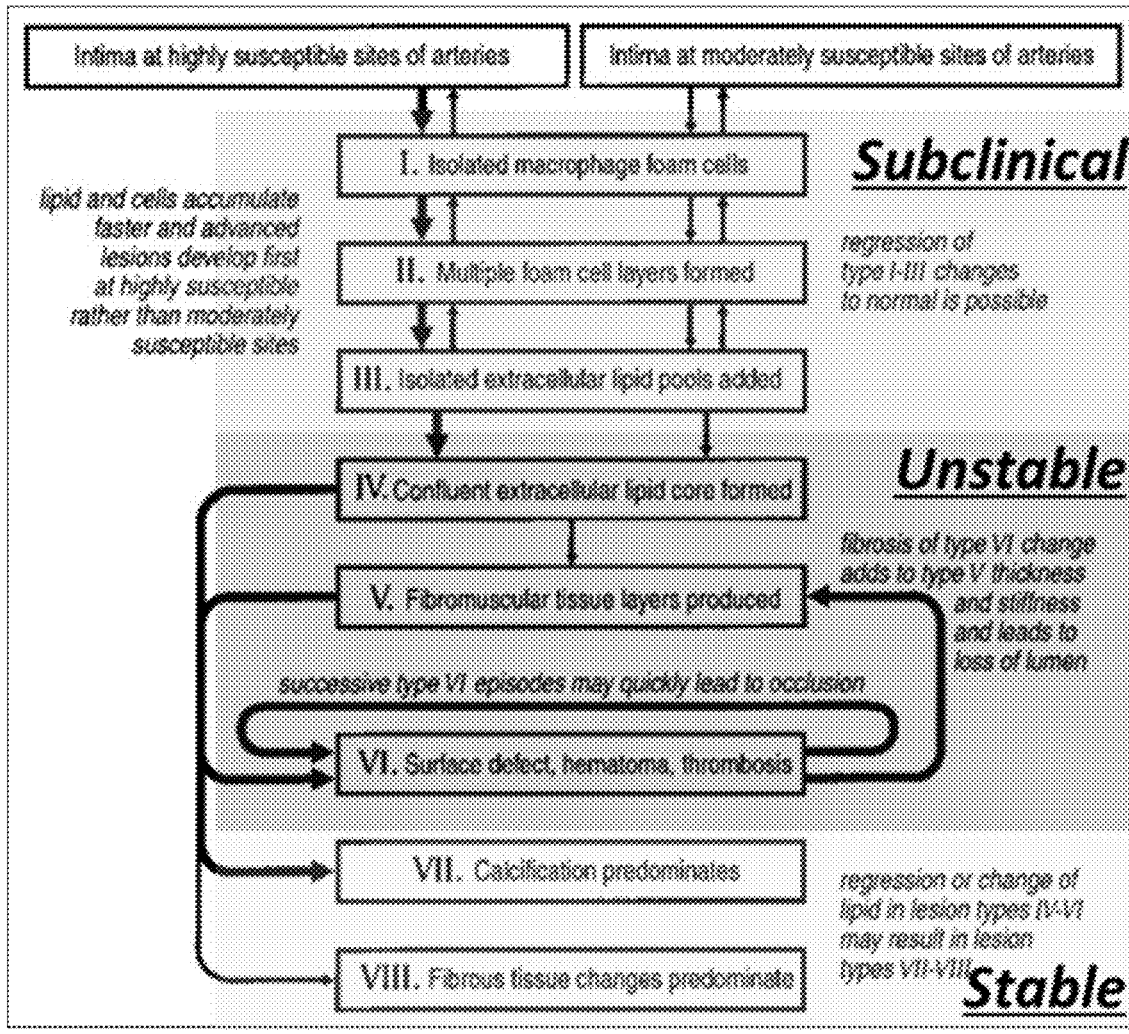
FIG. 19 depicts an example application of phenotyping purpose in directing vascular therapy, according to the present disclosure. The depicted example uses the Stary plaque typing system adopted by the AHA as an underlay with in vivo determined types shown in color overlays.

FIG. 19 is an example application of phenotyping purpose in directing vascular therapy, using the Stary plaque typing system adopted by the AHA as an underlay with in vivo determined types shown in color overlays. The left panel shows an example that labels according to the likely dynamic behavior of the plaque lesion based on its physical characteristics, and the right panel illustrates an example which uses the classification result for directing patient treatment. An example mapping is ['I','II','III','IV','V', 'VI','VII','VIII'] yielding class_map=[Subclinical, Subclinical, Subclinical, Subclinical, Unstable, Unstable, Stable, Stable]. This method is not tied to Stary, e.g., the Virmani system ['Calcified nodule', 'CTO', 'FA', 'FCP', 'Healed Plaque Rupture', 'PIT', 'IPH', 'Rupture', 'TCFA', 'ULC'] has been used with class_map=[Stable, Stable, Stable, Stable, Stable, Stable, Unstable, Unstable, Unstable, Unstable], and other typing systems may yield similarly high performance. In example embodiments, the systems and methods of the present disclosure may merge disparate typing systems, the class map may be changed, or other variations. For FFR phenotypes, values such as normal or abnormal may be used, and/or numbers may be used, to facilitate comparison with physical FFR for example.

Figure 20:
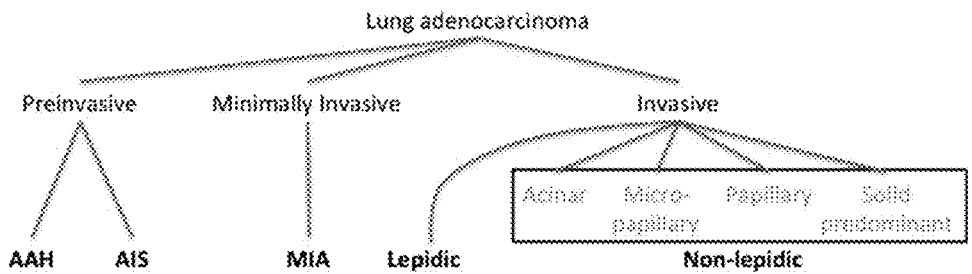
FIG. 20 depicts an example application of phenotyping for lung cancer, according to the present disclosure.

FIG. 20 is example for a different disease, e.g., lung cancer. In this example, the subtypes of masses are determined so as to direct the most likely beneficial treatment for the patient based on the manifest phenotype.

CNNs are expected to perform better than readings-vector classification because CNNs contain filters which extract spatial context which isn't included in (only) analyte area measurements. It may be practical to use a CNN despite the reduced training set because 1) there are relatively few classes corresponding to significantly different treatment alternatives (rather than being fully granular as might be done in research assays necessitating ex vivo tissue), e.g. three phenotypes for the classification problem, three risk levels for the outcome prediction/risk stratification problem, so the problem is generally easier.
2) the processing of analyte regions into false color regions, e.g., by level sets or other algorithm classes, performs a substantial portion of the image interpretation by generating the segmentations and presenting the classifier with a simplified, but considerably enriched data set. Measurable pipeline stages reduce the dimensionality of the data (reducing the complexity of the problem that the CNN must solve) while also providing verifiable intermediate values which can increase confidence in the overall pipeline.
3) re-formatting the data using a normalized coordinate system removes noise variation due to variables that do not have a substantial impact on the classification, e.g., vessel size in the plaque phenotyping example.

To test this idea a pipeline was built consisting of three stages:
1) semantic segmentation to identify which regions of the biomass fall into certain classes
2) spatial unwrapping to convert the vein/artery cross section into a rectangle, and
3) a trained CNN to read the annotated rectangles and identify which class (stable or unstable) it pertains to.

Without loss of generality, example systems and methods described herein may apply spatial unwrapping (for example, training and testing CNNs with (unwrapped dataset) and without (donut dataset) spatial unwrapping). Unwrapping was observed to improve the validation accuracy Semantic Segmentation and Spatial Unwrapping:

First, the image volume is preprocessed. This may include target initialization, normalization, and other pre-processing such as deblurring or restoring to form a region of interest containing a physiological target that is to be phenotyped. Said region is a volume composed of cross sections through that volume. Body site is either automatically determined or is provided explicitly by user. Targets for body sites that are tubular in nature are accompanied with a centerline. Centerlines, when present, can branch. Branches can be labelled either automatically or by user. Generalizations on centerline concept may be represented for anatomy that is not tubular but which benefit by some structural directionality, e.g., regions of a tumor. In any case, a centroid is determined for each cross section in the volume. For tubular structures this will be the center of the channel, e.g., the lumen of a vessel. For lesions this will be the center of mass of the tumor.

Figure 21:
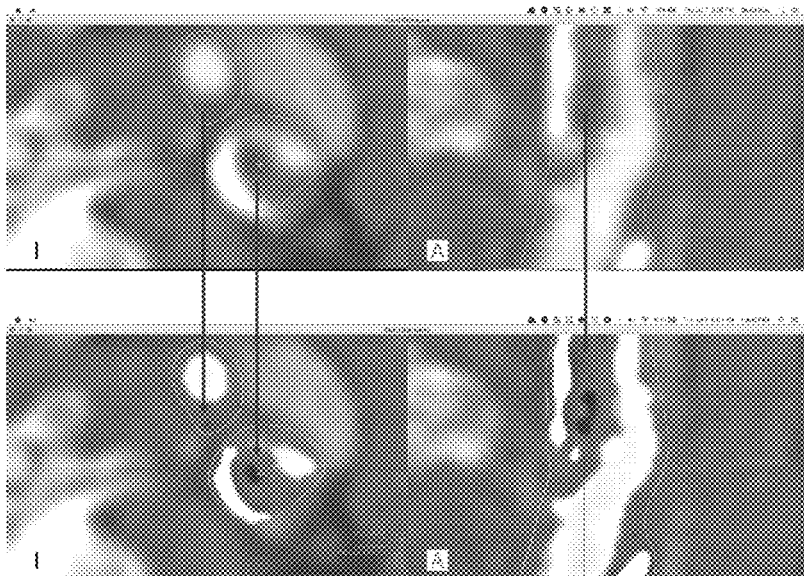
FIG. 21 illustrates an exemplary image pre-processing step of deblurring or restoring, according to the present disclosure. The deblurring or restoring uses a patient-specific point spread determination algorithm to mitigate artifacts or image limitations that result from the image formation process that may decrease the ability to determine characteristics predictive of the phenotype. The deblurred or restored (processed) images depicted (bottom) derive from CT imaging of a plaque (top) and are a result of iteratively fitting a physical model of the scanner point spread function with regularizing assumptions about the true latent density of different regions of the image.

FIG. 21 is representative of an exemplary image pre-processing step, in this case deblurring or restoring using a patient-specific point spread determination algorithm to mitigate artifacts or image limitations that result from the image formation process that may decrease the ability to determine characteristics predictive of the phenotype. The figure demonstrates a portion of the radiology analysis application analysis of a plaque from CT. Shown here are the deblurred or restored images that are a result of iteratively fitting a physical model of the scanner point spread function with regularizing assumptions about the true latent density of different regions of the image. This figure is included so as to illustrate that a variety of image processing operations may be performed so as to aid in the ability to perform quantitative steps, and in no way to indicate that this method is needed for the specific invention in this disclosure but rather being exemplary of steps which may be taken to improve overall performance.

Figure 36:
FIG. 36 depicts exemplary 3D segmentations of lumen, vessel wall, and plaque components (LRNC and calcification) for two patients presenting with chest pain and similar risk factors and degree of stenosis, according to the present disclosure. To the left: 68-year-old man with NSTEMI at follow-up. To the right: 65-year-old man with no event at follow-up. The systems and methods of the present disclosure correctly predicted their respective outcomes.
Figure 37:
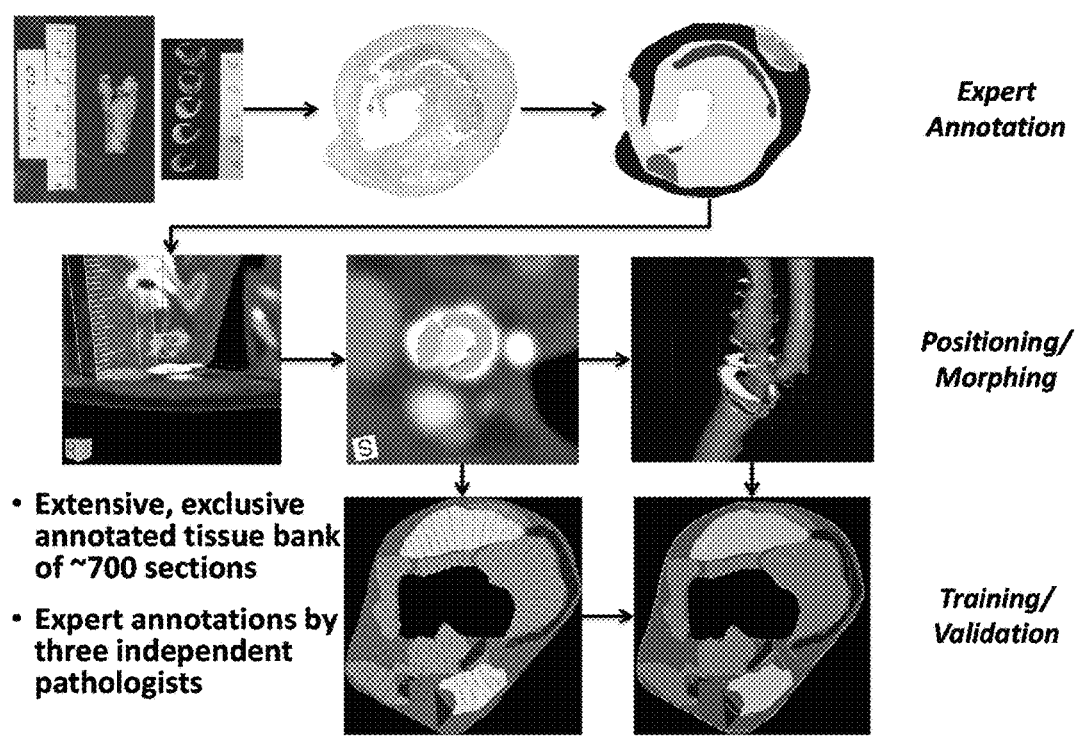
FIG. 37 depicts example histology processing steps for objective validation of tissue composition, according to the present disclosure.
Figure 38:
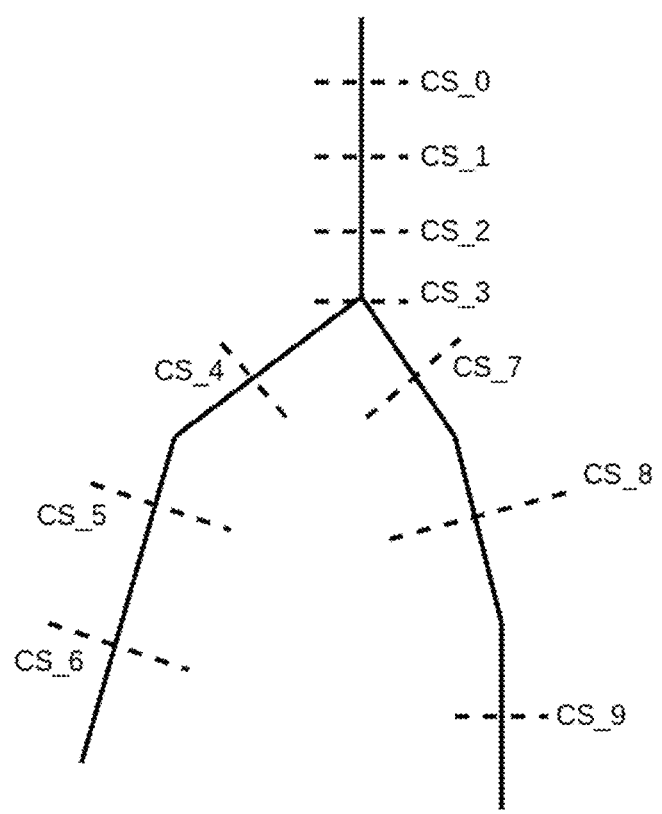
FIG. 38 is a schematic depiction of the multiple cross-sections that may be processed to provide a dynamic analysis across the entire scanned vessel tree, illustrating the relationships between cross-sections and where the processing of one depends on its neighbors, according to the present disclosure.

The (optionally deblurred or restored) image is represented in a Cartesian data set where x is used to represent how far from centroid, y represents a rotational theta, and z represents the cross section. One such Cartesian set will be formed per branch or region. When multiple sets are used, a "null" value will be used for overlapping regions, that is, each physical voxel will be represented only once across the sets, in such a way as to geometrically fit together. Each data set will be paired with an additional data set with sub-regions labelled by objectively verifiable tissue composition (see, e.g., FIG. 36). Example labels for vascular tissue can be lumen, calcification, LRNC, etc. Example labels for lesions could be necrotic, neovascularized, etc. These labels can be validated objectively, e.g. by histology (see, e.g., FIG. 37). Paired data sets will used as input to a training step to build a convolutional neural network. Two levels of analysis are supported, one at an individual cross-section level, optionally where the output varies continuously across adjacent cross-sections, and a second at the volume level (where individual cross-sections may be thought of as still frames, and the vessel tree traversal could be considered as analogous to movies).

Exemplary CNN Design:

AlexNet is a CNN, which competed in the ImageNet Large Scale Visual Recognition Challenge in 2012. The network achieved a top-5 error of 15.3%. AlexNet was designed by the SuperVision group, consisting of Alex Krizhevsky, Geoffrey Hinton, and Ilya Sutskever at U Toronto at the time. AlexNet was trained from scratch to classify an independent set of images (not used in training and validation steps during the network training). For the unwrapped data an AlexNet style network with 400×200 pixel input was used, and the donut network is AlexNet style with 280×280 pixel input (roughly the same resolution but different aspect ratio). All of the convolutional filter values were initialized with weights taken from AlexNet trained on the ImageNet dataset. While the ImageNet dataset is a natural image dataset, this simply serves as an effective method of weight initialization. Once training begins, all weights are adjusted to better fit the new task. Most of the training schedule was taken directly from the open source AlexNet implementation, but some adjustment was needed. Specifically, the base learning rate was reduced to 0.001 (solver.prototxt) and the batch size was reduced to 32 (train val.prototxt) for both the AlexNet-donut and AlexNet-unwrapped networks. All models were trained to 10,000 iterations and were compared to snapshots when trained till just 2,000 iterations. While a more in depth study on overfitting could be done, it was generally found that both training and validation error decreased between 2 k and 10 k iterations.

Alternative featurizers (prefixes) could include:
ResNet—https://arxiv.org/abs/1512.03385
GoogLeNet—https://www.cs.unc.edu/~wliu/papers/GoogLeNet.pdf
ResNext—https://arxiv.org/abs/1611.05431
ShuffleNet V2—https://arxiv.org/abs/1807.11164
MobileNet V2—https://arxiv.org/abs/1801.04381

Run-time optimizations such as frame-to-frame redundancy between cross-sections (sometimes referred to as "temporal" redundancy, but in our case, being a form of inter-cross-section redundancy) could be leveraged to save on computation (e.g., http://arxiv.org/abs/1803.06312). Many optimizations for training or inference may be implemented.

In example test implementations, AlexNet was trained to classify an independent set of images between two categories of clinical significance, e.g., 'unstable' plaques and 'stable' plaques, based on histology ground truth plaque types of V and VI, while the latter includes plaque types VII and VIII following the industry de-facto standard plaque classification nomenclature accepted by the American Heart Association (AHA), and on a related but distinct typing system by Virmani Without loss of generality, in illustrated examples, both total accuracy and a confusion matrix were be utilized to assess performance. This formalism was based on the notion of computing four possibilities in a binary classification system: true positives, true negatives, false positives and false negatives. In example embodiments, other outcome variables can be used, however, for example, one can utilize sensitivity and specificity as outcome variables, or the F1 score (the harmonic mean of precision and sensitivity). Alternatively, an AUC characteristic can be computed for a binary classifier. Furthermore, classifiers need not be binary based. For example, in some embodiments, classifiers may sort based on more than two possible states.

Dataset Augmentation:
Physician annotated data is expensive, so it is desirable to artificially increase medical datasets (e.g., for use in training and/or validation). Two different augmentation techniques were used in example embodiments described herein. Donuts were horizontally flipped randomly, as well as rotated to a random angle from 0 to 360. The resulting rotated donut was then cropped to the range in which the donut was present, and then padded with black pixels to fill the image to have a square aspect ratio. The result was then scaled to the 280×280 size and saved to a PNG.

The unwrapped dataset was augmented by randomly horizontally flipping, and then "scrolled" by a random number of pixels in the range from 0 to the width of the image. The result was then scaled to the 400×200 size and saved to a PNG.

Both datasets were increased by a factor of 15, meaning that the total number of images after augmentation is 15 times the original number. Class normalization was implemented, meaning that the final dataset has roughly the same number of images pertaining to each class. This is important as the original number of images for each class might be different, thus biasing the classifier to the class with the larger number of images in the training set.

Without loss off generality, each radiologist who performed the annotations can use an arbitrary number of tissue types.

Figure 22:
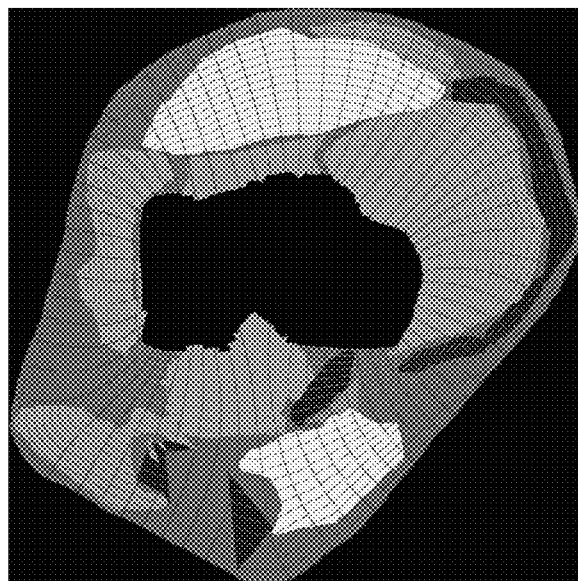
FIG. 22 depicts an exemplary application demonstrating an enriched dataset for atherosclerotic plaque phenotype, according to the present disclosure.

FIG. 22 illustrates an exemplary application that used to demonstrate aspects of the present invention, in this case being for classification of atherosclerotic plaque phenotype classification (using specific subject data by way of example). Different colors represent different tissue analyte types with dark gray showing the otherwise normal wall. The figure illustrates the result of ground truth annotation of tissue characteristics that are indicative of plaque phenotype as well as the spatial context of how they present in a cross section taken orthogonal to the axis of the vessel. It also illustrates a coordinate system that has been developed in order to provide a common basis for analysis of a large number of histological cross sections. Grid lines added to demonstrate coordinate system (tangential vs. radial distance) and overlaid on top of color-coded pathologist annotations. An important aspect of this is that data sets of this kind may be used efficiently in deep learning approaches because they simplify the information using a relatively simpler false color image in place of a higher-resolution full image but without losing spatial context, e.g., to have a formal representation for such presentations as "napkin ring sign", juxtaluminal calcium, thin (or thick) caps (spacing between LRNC and lumen), etc.

Figure 23:
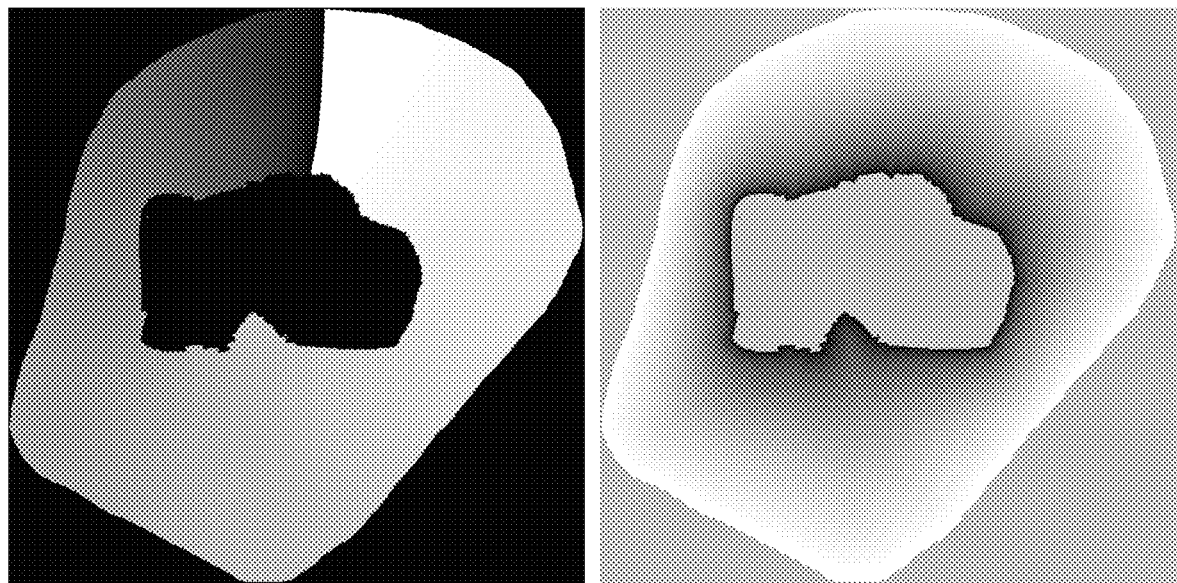
FIG. 23 illustrates tangential and radial direction variable internally represented using unit phasors and phasor angle (shown coded in grey scale) which exemplifies the use of normalized axes for tubular structures relevant to the vascular and other pathophysiology associated with such structures (e.g., the gastro-intestinal tract), according to the present disclosure.

FIG. 23 illustrates tangential and radial direction variable internally represented using unit phasors and here, phasor angle shown coded in gray scale, which exemplifies the use of normalized axes for tubular structures relevant to the vascular and other pathophysiology associated with such structures (e.g., the gastro-intestinal tract). Note that the vertical bar from black to white is a purely arbitrary boundary due to the gray scale encoding, and the normalized radial distance has a value of 0 at the luminal boundary and value of 1 at the outer boundary.

Figure 24:
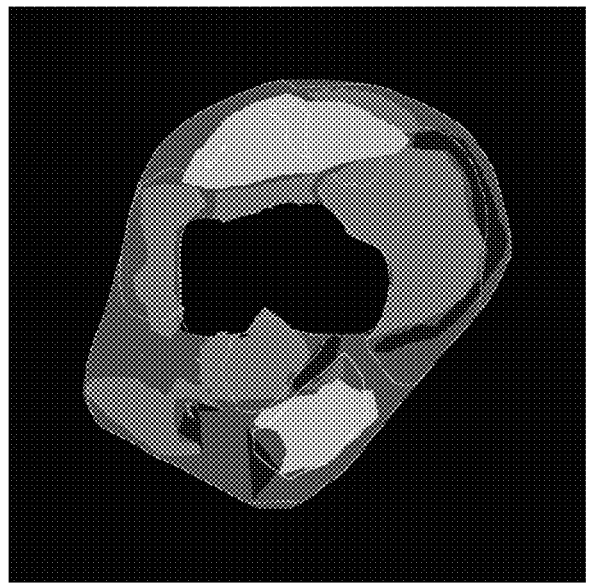
FIG. 24 illustrates an exemplary overlay of radiology analysis application generated annotations from CTA (outlined regions) on top of pathologist generated annotations from histology (solid regions), according to the present disclosure.

FIG. 24 illustrates an exemplary overlay of radiology analysis application generated annotations from CTA (unfilled color contours) on top of pathologist generated annotations from histology (solid color regions). An example aspect of the systems and methods presented herein is that the contours form in vivo non-invasive imaging can be used with the classification scheme so as to determine phenotype non-invasively, where the classifier is trained on known ground truth. Specifically, filling in the contours which are shown unfilled in this figure (so as to not obscure the relationship with the ex vivo annotation for this specific section which is provided to show the correspondence) creates input data for the classifier.

Figure 25:
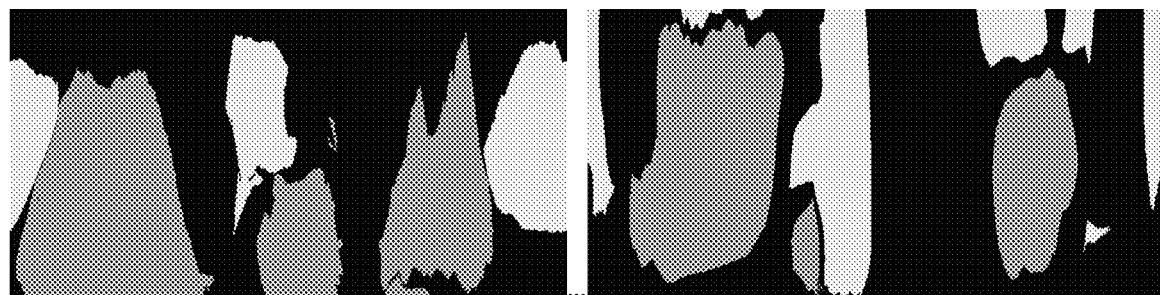
FIG. 25 demonstrates a further step of data enrichment, specifically, utilizing the normalized coordinate system to avoid non-relevant variation associated with the wall thickness and radial presentation, according to the present disclosure. Specifically, the "donut" is "unwrapped" while retaining the pathologist annotations.

FIG. 25 demonstrates a further step of data enrichment, specifically, utilizing the normalized coordinate system to avoid non-relevant variation associated with the wall thickness and radial presentation. Specifically, the "donut" is "unwrapped" while retaining the pathologist annotations. The left panel illustrates pathologist region annotations of a histological slice of a plaque after morphing to convert the cut open "C" shape back into the in vivo "O" shape of the intact vessel wall. Horizontal axis is the tangential direction around the wall. Vertical axis is the normalized radial direction (bottom is luminal surface, top is outer surface). Also note that the finer granularity of the pathologist annotations has been collapsed to match the granularity intended for extraction by the in vivo radiology analysis application (e.g., LRNC, CALC, IPH). The right panel illustrates the comparable unwrapped radiology analysis application annotations. Axes and colors are the same as the pathologist annotations.

Figure 26:
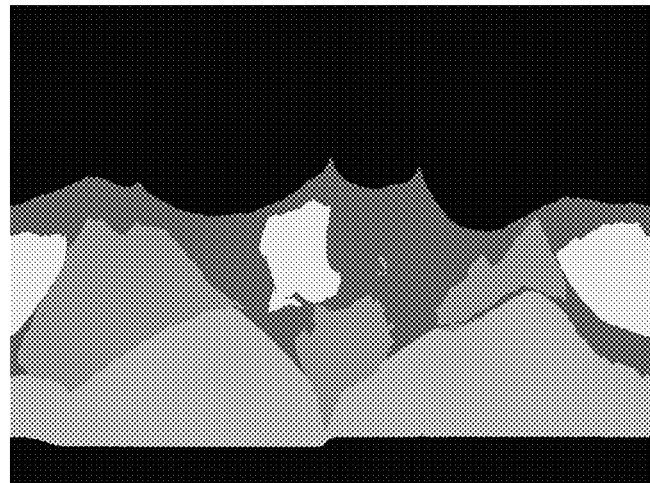
FIG. 26 represents a further step of data enrichment relevant to plaque phenotyping, according to the present disclosure. Working from the unwrapped formalism, luminal irregularity (for example from ulceration or thrombus) and local varying wall thickening is represented.

FIG. 26 represents the next refinement relevant to the plaque phenotyping example. Working from the unwrapped formalism, luminal irregularity (as results, for example from ulceration or thrombus) and local varying wall thickening are represented. The light grey at bottom represents the lumen (added in this step so as to represent that luminal surface irregularity) and the black used in the prior step is now replaced with dark grey, to represent the varying wall thickening. Black now represents area outside of the wall entirely.

Figure 27:
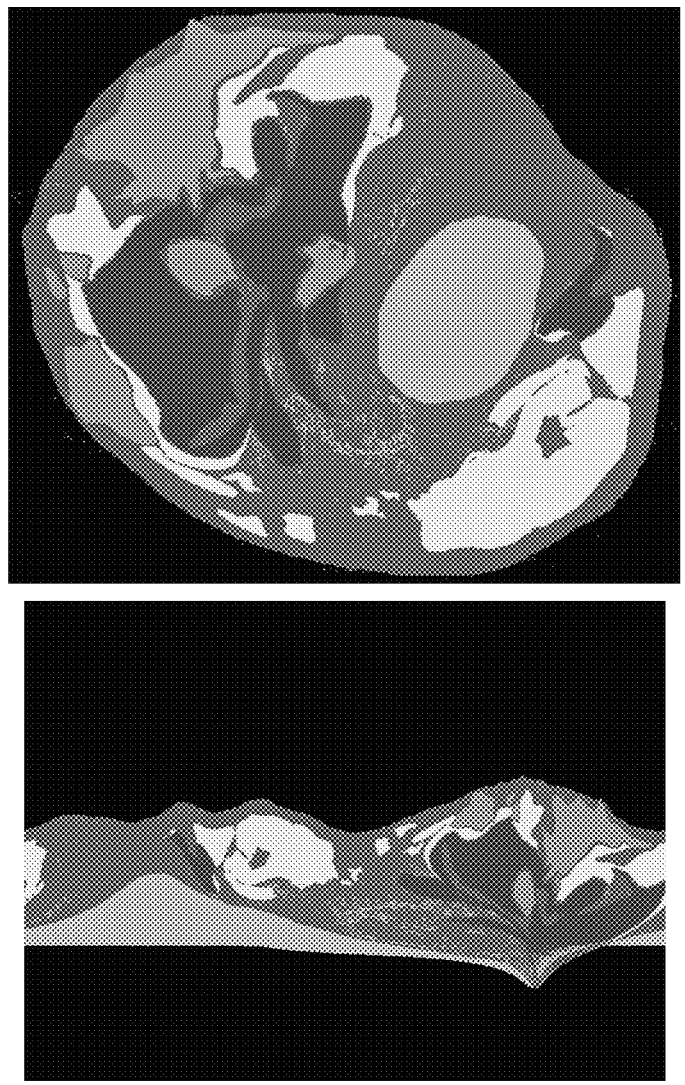
FIG. 27 represents data enriched imaging (in both wrapped and unwrapped forms) including intra-plaque hemorrhage and/or other morphology, according to the present disclosure.

FIG. 27 represents an additional example, so as to include, for example, intra-plaque hemorrhage and/or other morphology aspects as needed (using specific subject data by way of example). The left panel shows the donut representation and the right panel the unwrapped with the luminal surface and localized wall thickening represented.

Example CNNs tested included CNNs based on AlexNet and Inception frameworks.

AlexNet Results:

In example embodiments tested, the convolutional filter values were initialized with weights taken from AlexNet trained on the ImageNet (cite here) dataset. While the ImageNet dataset is a natural image dataset, this simply serves as an effective method of weight initialization. Once training begins, all weights are adjusted to better fit the new task.

Most of the training schedule was taken directly from the open source AlexNet implementation, but some adjustment was needed. Specifically, the base learning rate was reduced to 0.001 (solver.prototxt) and the batch size was reduced to 32 (train val.prototxt) for both the alexnet-donut and alexnet-unwrapped networks.

All models were trained to 10,000 iterations and were compared to snapshots when trained till just 2,000 iterations. While a more in depth study on overfitting could be done, it was generally found that both training and validation error decreased between 2 k and 10 k iterations.

A brand new AlexNet network model was trained from scratch for 4 (four) different combinations of ground-truth results of two leading pathologists, two different ways of processing images (see above), as well as unwrapped images and donut images. The results are listed in FIG. 28. Each dataset variation had its training data augmented by 15x with class normalization enabled. A network was trained on this augmented data and then was tested on the corresponding un-augmented validation data corresponding to that variation. For the unwrapped data an AlexNet style network with 400×200 pixel input was used, and the donut network is AlexNet style with 280×280 pixel input (roughly the same resolution but different aspect ratio). Note that in test embodiments the dimensions of the conventional layers as well as the fully connected layers were changed. Thus, the network in the AlexNet test embodiments can be described as a five convolutional layer, three fully connected layer network. Without loss of generality, here are some high-level conclusions that are illustrated from these results:

1) With the exception of the WN_RV dataset, it does indeed seem to be that the unwrapped data is easier for the data to analyze as it receives higher validation accuracy across the board
2) The non-normalized data is demonstrated to be more representative as anticipated.
3) In regards to the WN_RV dataset, the original idea was to pool WN and RV truth data to see the compatibility of the typing systems and the degree to which sets may be merged. In doing so, significant differences were observed in the WN vs RV data. The original intention of the WN_RV experiments was to pool training data from multiple pathologists to see if the information contributed to efficacy. Instead degradation rather than improvement was observed. This was determined to be because of variations in color scheme which impeded such pooling of data. Thus, one can consider normalizing the color scheme to enable pooling.

Exemplary Alternative Network: Inception:

Transfer-learning re-training of an Inception v3 CNN was started with the Aug. 8 2016 version of the network uploaded on the TensorFlow site for public use. The network was trained for 10,000 steps. Training and Validation sets were normalized in number of images via image augmentation so both sub-sets amounted to the same number of annotated images. All other network parameters were taken to be at their default values.

Pre-trained CNNs can be used to classify imaging features using the output from the last convolution layer, which is a numeric tensor with dimensionality of 2048×2 in the case of the Google Inception v3 CNN. We then train an SVM classifier to recognize the object. This process is normally performed on the Inception model after a transfer-learning and Fine-Tuning steps in which the model initially trained on the ImageNet 2014 dataset has its last, softmax layer removed and re-trained to recognize the new categories of images.

Alternative Embodiments

FIG. 29 provides an alternative example, for phenotyping potentially cancerous lung lesions. The left-most panel indicates the outlines of a segmented lesion, with pre-processing to separate out into solid vs. semi-solid ("ground glass") sub regions. The middle panels indicate its location in the lung, and the right-most panel shows it with false color overlay. In this case, the 3-dimensional nature of the lesion is likely considered significant, so instead of processing 2-D cross-sections separately, techniques such as video interpretation from computer vision may be applied for the classifier input data set. In fact, processing multiple cross-sections sequentially, as if in a "movie" sequence along a centerline, can generalize these methods for tubular structures.

Another generalization is where the false colors are not selected from a discrete palette but instead have continuous values at pixel or voxel locations. Using the lung example, FIG. 30 shows a set of features, sometimes described as so-called "radiomics" features that can be calculated for each voxel. Such a set of values may exist in arbitrary number of pre-processed overlays and be fed into the phenotype classifier.

Other alternative embodiments include using change data, for example as collected from multiple timepoints, rather than (only) data from a single timepoint. For example, if the amount or nature of a negative cell type increased, it may be said to be a "progressor" phenotype, vs. a "regressor" phenotype for decreases. The regressor might be, for example, due to response to a drug. Alternatively, if the rate of change for, say, LRNC is rapid, this may imply a different phenotype. The extension of the example to use delta values or rates of change is obvious to one skilled in the art.

As an additional alternative embodiment, non-spatial information, such as which are derived from other assays (e.g., lab results), or demographics/risk factors, or other measurements taken from the radiological image, may be fed into the final layers of the CNN to combine the spatial information with non-spatial information. Also, localized information such as use of a pressure wire with readings at one or more certain locations along a vessel from a reference such as a bifurcation or ostia, by inference of full 3D coordinates at imaging may be determined.

Whereas the focus of these examples has been on phenotype classification, similar approaches may be applied to the problem of outcome prediction, as a further embodiment of this invention.

Example Implementations

Figure 34:
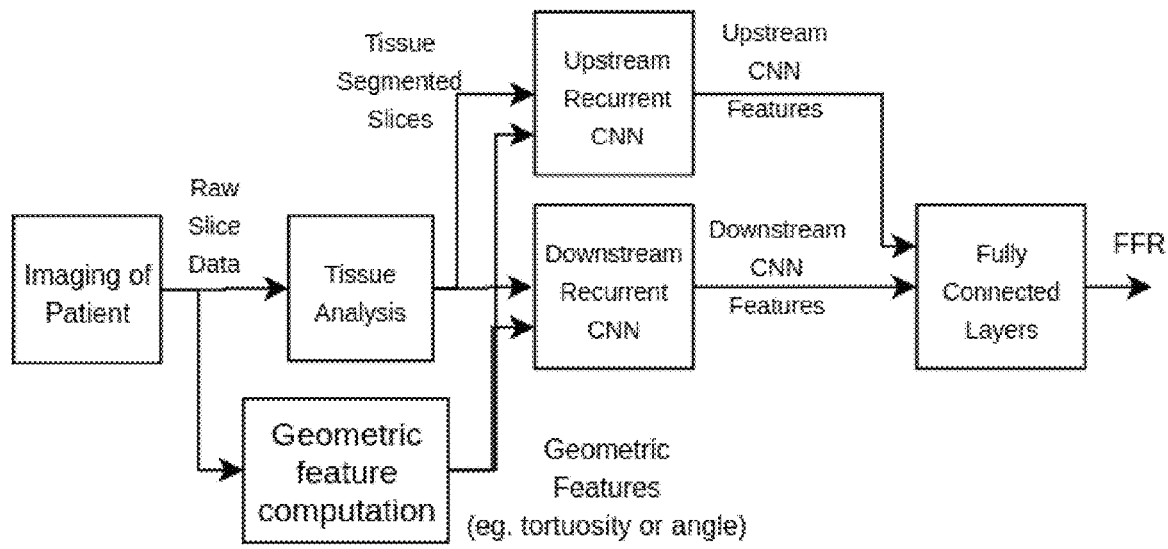
FIG. 34 is a block diagram of example data analysis according to the present disclosure. Images are collected of the patient, the raw slice data is used in a set of algorithms to measure biological properties that may be objectively validated, these are in turn formed as enriched data sets to feed one of more CNNs, in this example where results are forward and back-propagated using recurrent CNNs to implement constraints or creates continuous conditions (such as a monotonically decreasing fractional flow reserve from proximal to distal throughout the vessel tree, or constant HRP value in a focal lesion, or other constraints).
Figure 35:
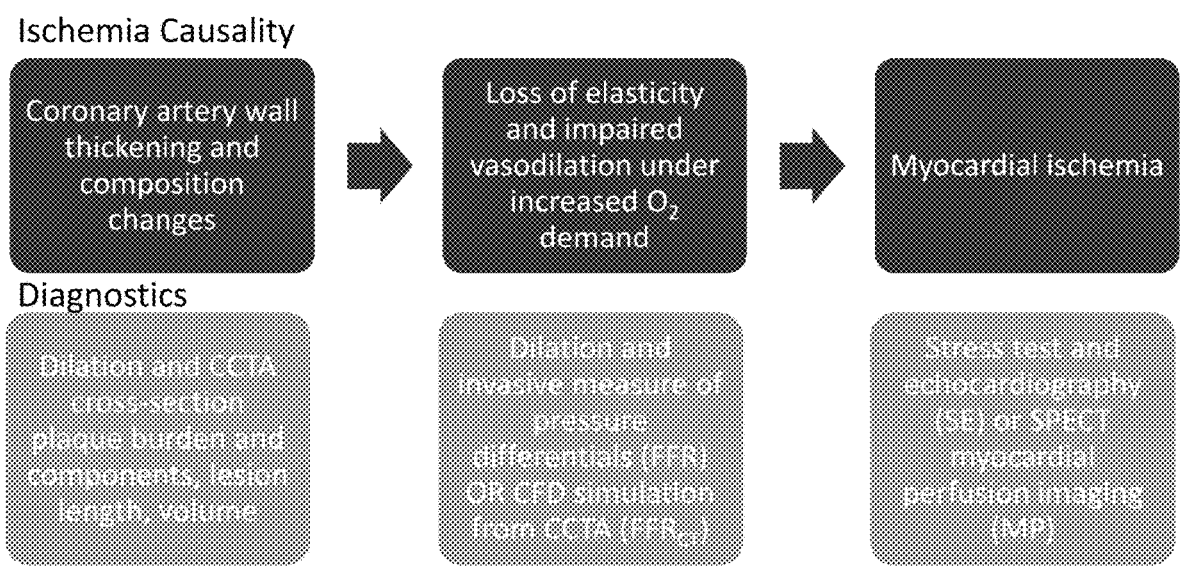
FIG. 35 illustrates causality of coronary ischemia and available diagnostics, according to the present disclosure.

Systems and methods of the present disclosure may advantageously comprise a pipeline consisting of multiple stages. FIG. 34 provides a further example implementation of a hierarchical analytics framework. Biological properties are identified and quantified by semantic segmentation to identify biological properties singly or in combination, in the example application lipid-rich necrotic core, cap thickness, stenosis, dilation, remodeling ratio, tortuosity (e.g., entrance and exit angles), calcification, IPH, and/or ulceration, which is represented numerically as well as in enriched data sets with spatial unwrapping to convert the vein/artery cross-section into a rectangle, and then medical conditions (example e.g., ischemia-causing fractional flow reserve FFR, high-risk phenotype HRP, and/or risk stratification time to event (TTE) using trained CNN(s) to read the enriched data sets to identify and characterize the condition. Images are collected of the patient, the raw slice data is used in a set of algorithms to measure biological properties that may be objectively validated, these are in turn formed as enriched data sets to feed one of more CNNs, in this example where results are forward and back-propagated using recurrent CNNs to implement constraints or creates continuous conditions (such as a monotonically decreasing fractional flow reserve from proximal to distal throughout the vessel tree, or constant HRP value in a focal lesion, or other constraints). Ground truth data for HRP may exist as expert pathologist determined plaque types at given cross-sections, having been determined ex vivo. Ground truth data for FFR may be from physical pressure wire, with one or more measured values, and network training for locations along the centerline proximal of a given measurement being constrained to be greater than or equal to the measured value, locations distal being constrained to be less than or equal, and when two measurements on the same centerline are known, that the values between the two measured values be constrained within the interval.

These properties and/or conditions may be assessed at a given point in time and/or change across time (longitudinal). Without loss of generality, other embodiments performing similar steps, either in plaque phenotyping or in other applications, would be embodiments of the invention.

In example implementations, biological properties can include one or more of the following:
Angiogenesis
Neovascularization
Inflammation
Calcification
Lipid-deposits
Necrosis
Hemorrhage
Ulceration
Rigidity
Density
Stenosis
Dilation
Remodeling Ratio
Tortuosity
Flow (e.g., of blood in channel)
Pressure (e.g., of blood in channel or one tissue pressing against another)
Cell types (e.g., macrophages)
Cell alignment (e.g., of smooth muscle cells)
Shear stress (e.g., of blood in channel)
Analysis can include determining one or more of quantity, degree and/or character for each of the aforementioned biological properties.

Figure 31:
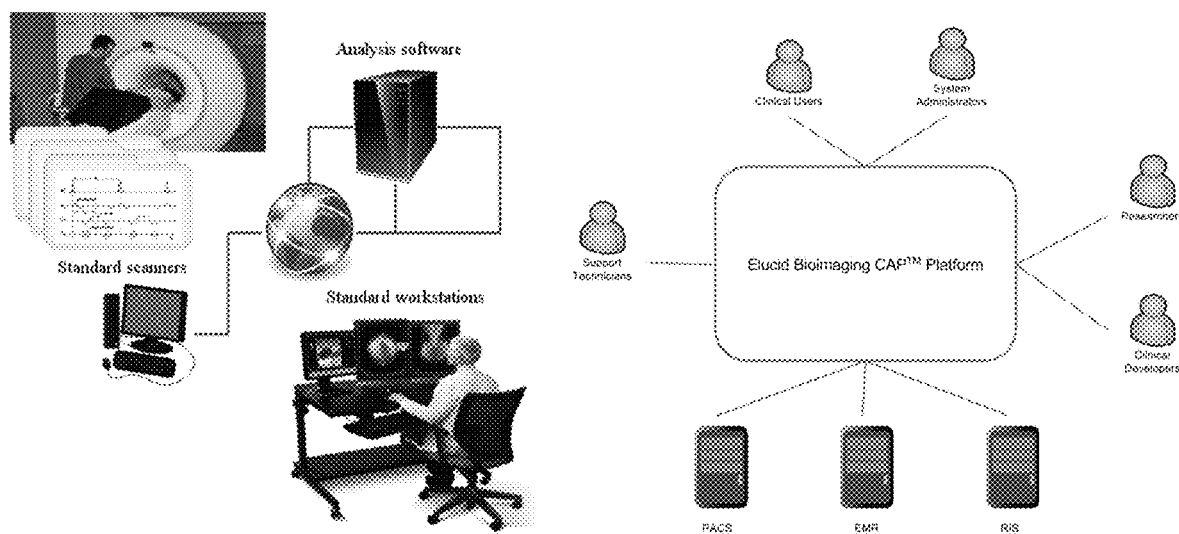
FIG. 31 illustrates a high-level view of one example approach to user interaction with a computer-aided phenotyping system, according to the present disclosure.

Conditions that can be determined based on the biological properties may include one or more of:
Perfusion/ischemia (as limited) (e.g., of brain or heart tissue)
Perfusion/infarction (as cut off) (e.g., of brain or heart tissue)
Oxygenation
Metabolism
Flow reserve (ability to perfuse) e.g., FFR(+) vs. (−) and/or continuous number
Malignancy
Encroachment
High-risk plaque e.g., HRP(+) vs. (−) and/or labelled phenotype
Risk stratification (whether as probability of event, or time to event) (e.g., MACCE, mentioned explicitly)
Validation in the form of truth bases can include the following:
Biopsy
Expert tissue annotations form excised tissue (e.g., endarterectomy or autopsy)
Expert phenotype annotations on excised tissue (e.g., endarterectomy or autopsy)
Physical pressure wire
Other imaging modalities
Physiological monitoring (e.g., ECG, SaO2, etc.)
Genomic and/or proteomic and/or metabolomics and/or transcriptomic assay
Clinical outcomes
Analysis can be both at a given point in time as well as longitudinal (i.e., change across time)
Exemplary System Architecture:
FIG. 31 illustrates a high-level view of the users and other systems that interact with an analytics platform, as per the systems and methods of the present disclosure. Stakeholders of this view include System Administrators, Support Technicians, which have Interoperability, Security, Failover & Disaster Recovery, Regulatory concerns.

Figure 32:
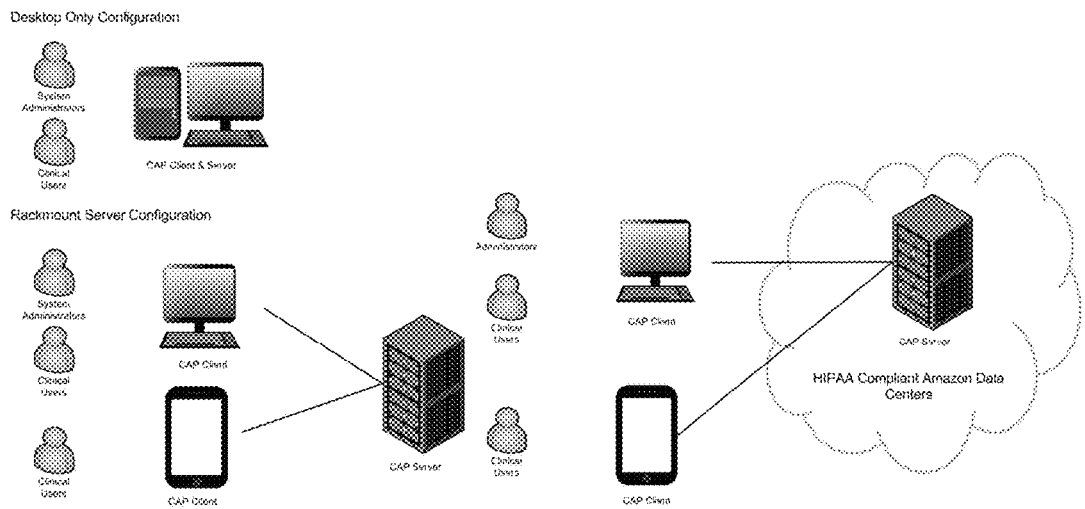
FIG. 32 illustrates example system architectures, according to the present disclosure.

The platform can be deployed in two main configurations; on-premises, or remote server (FIG. 32). The platform deployment may be a stand-alone configuration (Left Upper), on-premises server configuration (Left Lower), or remote server configuration (Right). The on-premises deployment configuration can have two sub-configurations; desktop only or rackmount. In the remote configuration, the platform may be deployed on a HIPAA compliant data center. Clients access that API server over a secure HTTP connection. Clients can be desktop or tablet browsers. No hardware except for the computers running the web browsers is deployed on the customer site. The deployed server may be on a public cloud or an extension of the customer's private network using a VPN.

Figure 33:
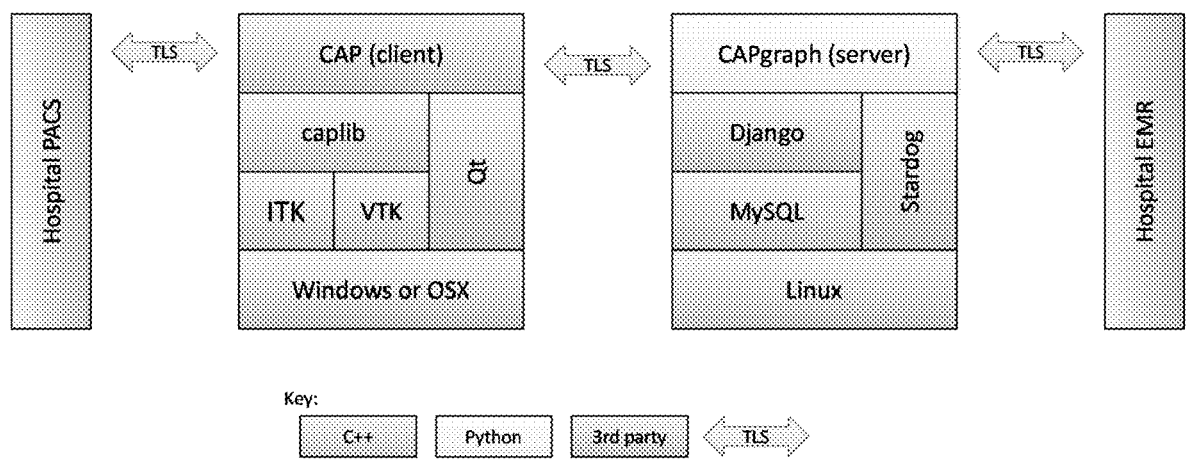
FIG. 33 illustrates components of example system architectures, according to the present disclosure.

An exemplary embodiment is comprised of a client and a server. For example, FIG. 33 illustrates a client as a C++ application and the server as a Python application. These components interact using HTML 5.0, CSS 5.0 and JavaScript. Wherever possible open standards are used for interfaces including but not limited to; HTTP(S), REST, DICOM, SPARQL, and JSON. Third party libraries are also used as shown in this view which shows the primary pieces of the technology stack. Many variations and different approaches may be understood by people skilled in the art.

Various embodiments of the above-described systems and methods may be implemented in digital electronic circuitry, in computer hardware, firmware, and/or software. The implementation can be as a computer program product (i.e., a computer program tangibly embodied in an information carrier). The implementation can, for example, be in a machine-readable storage device and/or in a propagated signal, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, Bluetooth, code-division multiple access (CDMA) network, time division multiple access (TDMA) network, global system for mobile communications (GSM) network), and/or other circuit-based networks.

The computing device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a World Wide Web browser (e.g., Microsoft® Internet Explorer® available from Microsoft Corporation, Mozilla® Firefox available from Mozilla Corporation). The mobile computing device includes, for example, a Blackberry®, iPAD®, iPhone® or other smartphone device.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

Although the present disclosure has been described herein with reference to particular embodiments, the present disclosure is not intended to be limited to the particulars disclosed herein; rather, the present disclosure extends to all variations and generalizations thereof that would be apparent to a person of ordinary skill in the art including those within the broadest scope of the appended claims.

The invention claimed is:

1. A method for computer aided phenotyping of a pathology using an enriched radiological dataset, the method comprising:
receiving a radiological dataset for a patient, wherein the radiological dataset is obtained non-invasively;
enriching the dataset by performing analyte measurement and/or classification of one or more of: (i) anatomic structure, (ii) shape or geometry or (iii) tissue characteristic, type, or character, with objective validation for a set of analytes relevant to a pathology, wherein the analyte measurement and/or classification of anatomic structure, shape, or geometry and/or tissue characteristic, type, or character includes semantic segmentation to identify and classify regions of interest in the radiological dataset, wherein the regions of interest are identified with respect to cross-sections of a pathology-specific structure in the radiological dataset; and
using a machine learned classification approach based on known ground truths to process the enriched dataset and determine a phenotype for the pathology.

2. The method of claim 1, wherein enriching the dataset further includes spatial transformations of the dataset to accentuate biologically-significant spatial context.

3. The method of claim 1, wherein enriching the dataset includes both (i) semantic segmentation to identify and classify regions of interest in cross-sections of a pathology-specific structure in the radiological dataset to produce an annotated dataset and (ii) spatially transforming the annotated dataset with respect to the cross-sections of a pathology-specific structure to produce a pathology-appropriate transformed dataset.

4. The method of claim 1, wherein an image volume in the radiological dataset is preprocessed to form a region of interest containing a physiological target, lesion, and/or set of lesions that is to be analyzed.

5. The method of claim 4, wherein the region of interest and/or the physiological target, lesion, and/or set of lesions are at least one of (i) automatically determined from the radiological dataset or (ii) identified by a user from the radiological dataset.

6. The method of claim 4, wherein the region of interest includes one or more cross sections, each composed of projections through that volume.

7. The method of claim 4, wherein the pre-processing the image volume includes deblurring or restoring using a patient-specific point spread determination algorithm to mitigate artifacts or image limitations that result from the image formation process.

8. The method of claim 1, wherein the machine learned classification approach is use of a trained convolutional neural network (CNN), wherein the CNN is based on a refactoring of AlexNET, Inception, CaffeNet, or other open source or commercially available framework.

9. The method of claim 1, wherein the dataset is enriched by visually using different colors to represent different analyte sub-regions.

10. The method of claim 1, wherein dataset enrichment includes ground truth annotation of analyte sub-regions as well as providing a spatial context of how such analytes sub-regions present in cross-section.

11. The method of claim 10, wherein the spatial context provides a common basis for analysis of enhanced dataset relative to histological cross-sections.

12. The method of claim 10, wherein the spatial context includes providing a coordinate system based on polar coordinates relative to a centroid of each cross-section.

13. The method of claim 1, wherein dataset enrichment includes ground truth annotation of analyte sub-regions using ex vivo classification independent of or in conjunction with image-based classification based on a common spatial context between the radiological dataset and ex vivo data.

14. The method of claim 13, wherein enriched dataset is visualized using different colors to represent different analyte sub-regions, wherein colors for visualizing the enhanced dataset are selected to correspond to colors utilized in the ex vivo data.

15. The method of claim 13, wherein the enriched dataset includes a visual overlay of ex-vivo data over the radiological data.

16. The method of claim 1, wherein the radiological dataset includes computed tomography (CT), dual energy computed tomography (DECT), spectral computed tomography (spectral CT), computed tomography angiography (CTA), cardiac computed tomography angiography (CCTA), magnetic resonance imaging (MRI), multi-contrast magnetic resonance imaging (multi-contrast MRI), ultrasound (US), positron emission tomography (PET), intra-vascular ultrasound (IVUS), optical coherence tomography (OCT), near-infrared radiation spectroscopy (NIRS), and/or single-photon emission tomography (SPECT) diagnostic images.

17. The method of claim 16, wherein enriching the dataset includes using image deblurring or restoring is used to identify lesions of interest and extract pathology composition quantitatively.

18. The method of claim 16, wherein enriching the dataset includes spatially transforming cross-sectional segmented images into an 'pathology-appropriate transformed' reference frame.

19. The method of claim 1, further comprising using a machine learned classification approach based on known ground truths to process the enriched dataset and determine a predictive outcome related to the pathology.

* * * * *

UNITED STATES PATENT AND TRADEMARK OFFICE
CERTIFICATE OF CORRECTION

Page 1 of 1

PATENT NO. : 11,094,058 B2
APPLICATION NO. : 16/203418
DATED : August 17, 2021
INVENTOR(S) : Andrew J. Buckler et al.

It is certified that error appears in the above-identified patent and that said Letters Patent is hereby corrected as shown below:

In the Specification

In Column 1, Line 21, please insert the following:
--GOVERNMENT RIGHTS IN THE INVENTION
This invention was in part made with government support under National Science Foundation SBIR Award 1248316 and National Institute of Health SBIR Award R44 HL 126224-01A1. The government may have certain rights in the invention.--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*